(12) United States Patent
Türck et al.

(10) Patent No.: US 6,660,524 B1
(45) Date of Patent: Dec. 9, 2003

(54) CONTROL OF GENE EXPRESSION IN EUKARYOTES

(75) Inventors: Jutta Anna Türck, Cambridge (GB); John Anthony Charles Archer, Cambridge (GB)

(73) Assignee: Advanced Technologies (Cambridge) Limited, London (GB)

(*) Notice: Subject to any disclaimer, the term of this patent is extended or adjusted under 35 U.S.C. 154(b) by 0 days.

(21) Appl. No.: 09/469,211

(22) Filed: Dec. 22, 1999

(51) Int. Cl.⁷ .............................. C12N 5/04; C12N 15/63

(52) U.S. Cl. ..................................... 435/419; 435/320.1
(58) Field of Search ................................ 435/419, 69.1, 435/243, 468, 325, 320.1, 375; 536/23.1, 24.1; 800/278, 295

(56) References Cited

U.S. PATENT DOCUMENTS

| 5,659,122 A | | 8/1997 | Austin |
| 5,723,765 A | * | 3/1998 | Oliver et al. |
| 5,789,156 A | * | 8/1998 | Bujard et al. |
| 5,989,910 A | * | 11/1999 | Mermod et al. |
| 6,114,600 A | * | 9/2000 | Ow et al. |
| 6,130,368 A | * | 10/2000 | Londesborough et al. |

FOREIGN PATENT DOCUMENTS

| WO | WO 93/19189 | 9/1993 |
| WO | WO 93/21334 | 10/1993 |
| WO | WO 96/04393 | 2/1996 |
| WO | WO 96/27673 | 9/1996 |
| WO | WO 97/20056 | 6/1997 |
| WO | WO99/00517 | 1/1999 |

OTHER PUBLICATIONS

Powell et al (1998) Antonie van Leewenhock 74:175–188.*
Giese et al (1996) Mol Gen Genet 252:429–436.*
Aoyama and Chua, 1997, "A Glucocorticoid–Mediated Transcriptional Induction System in Transgenic Plants", Plant J. 11:605–612.
Bechtold et al., 1993, "In planta Agrobacterium–Mediated Gene Transfer by Infiltration of Adult Arabidopsis thaliana Plants", C.R. Acad. Sci. Paris/Life Sciences 316:1194–1199.
Boutry et al., 1987, "Targeting of Bacterial Chloramphenicol Acetyltransferase to Mitochondria in Transgenic Plants", Nature, 328:340–342.
Caddick et al., 1998, "An Ethanol Inducible Gene Switch for Plants Used to Manipulate Carbon Metabolism", Nature Biotechnology 16:177–180.
Clough and Bent, 1998, "Floral Dip: A Simplified Method for Agrobacterium–Mediated Transformation of Arabidopsis thaliana", Plant J. 16:735–743.
Felenbok, 1991, "The Ethanol Utilization Regulon of Aspergillus nidulans: the alcA–alcR System as a Tool for the Expression of Recombinant Proteins", J. Biotechnol. 17:11–18.

Fillinger and Felenbok, 1996, "A Newly Identified Gene Cluster in Aspergillus nidulans Comprises Five Novel Genes Localized in the alc Region that are Controlled both by the Specific Transactivator AlcR and the General Carbon–Catabolite Repressor CreA", Mol. Microbiol. 20:475–488.
Frohberg et al., 1991, "Characterization of the Interaction of Plant Transcription Factors Using a Bacterial Repressor Protein", Proc. Natl. Acad. Sci. USA 88:10470–10474.
Gallie et al., 1987, "A Comparison of Eukaryotic Viral 5'–Leader Sequences as Enhancers of mRNA Expression in vivo", Nucl. Acids Res. 15:8693–8711.
Gatz et al., 1992, "Stringent Repression and Homogeneous De–Repression by Tetracycline of a Modified CaMV 35S Promoter in Intact Transgenic Tobacco Plants", Plant J. 2:397–404.
Gatz et al., 1991, "Regulation of a Modified CaMV 35S Promoter by the Tn10–Encoded Tet Repressor in Transgenic Tobacco", Mol. Gen. Genet. 227:229–237.
Gatz and Quail, 1988, "Tn 10–Encoded tet Repressor Can Regulate an Operator–Containing Plant Promoter", Proc. Natl. Acad. Sci. USA 85:1394–1397.
Goff et al., 1990, "Transactivation of Anthocyanin Biosynthetic Genes Following Transfer of B Regulatory Genes into Maize Tissues", EMBO J. 9:2517–2522.
Gossen et al., 1995, "Transcriptional Activation by Tetracyclines in Mammalian Cells", Science 268:1766–1769.
Hanna–Rose and Hansen, 1996, "Active Repression Mechanisms of Eukaryotic Transcription Repressors", TIG 12:229–234.
Haydon and Guest, 1991, "A New Family of Bacterial Regulatory Proteins", FEMS Microbiol. Lett. 79:291–296.
Hedley et al., 1993, "cDNA Cloning and Expression of a Potato (Solanum tuberosum) Invertase", Plant Mol. Biol. 22:917–922.
Horsch et al., 1985, "A Simple and General Method for Transferring Genes into Plants", Science 227:1229–1231.
Iturriaga et al., 1989, "Endoplasmic Reticulum Targeting and Glycosylation of Hybrid Proteins in Transgenic Tobacco", Plant Cell 1:381–390.

(List continued on next page.)

Primary Examiner—Terry McKelvey
(74) Attorney, Agent, or Firm—Pennie & Edmonds LLP

(57) ABSTRACT

A chemically inducible gene expression system is described. A chimeric gene having a first sequence comprising a promoter and a regulator polypeptide is linked with a second sequence comprising a promoter and a coding or non-coding sequence. Expression of the target gene of the second sequence is controlled by the regulator polypeptide which is acted upon by an inducer. The inducer is a chemical compound, such as OHP, which acts upon the OHP responsive regulator polypeptide, which can be obtained from Rhodococcus sp. V49. Various domain regions and complementary response elements are also described.

35 Claims, 28 Drawing Sheets

OTHER PUBLICATIONS

Jefferson, 1987, "Assaying Chimeric Genes in Plants: the GUS Gene Fusion System", Plant Mol. Biol. Reporter 5:387–405.

Jobling and Gehrke, 1987, "Enhanced Translation of Chimaeric Messenger RNAs Containing a Plant Viral Untranslated Leader Sequence", Nature 325:622–625.

Kapilla et al., 1997, "An Agrobacterium–Mediated Transient Gene Expression System for Intact Leaves", Plant Sci. 122:101–108.

Klein et al., 1987, "High–Velocity Microprojectiles for Delivering Nucleic Acids into Living Cells", Nature 327:70–73.

Knight and Gray, 1995, "The N–Terminal Hydrophobic Region of the Mature Phosphate Translocator is Sufficient for Targeting to the Chloroplast Inner Envelope Membrane", Plant Cell 7:1421–1432.

Kulmburg et al., 1992, "Specific Binding Sites for the Activator Protein, ALCR, in the alcR Promoter of the Ethanol Regulon of *Asperigillus nidulans*", J. Biol. Chem. 267:21146–21153.

Lloyd et al., 1994, "Epidermal Cell Fate Determination in Arabidopsis: Patterns Defined by a Steroid–Inducible Regulator", Science 266:436–439.

Lüscher and Eisenman, 1990, "New Light of Myc and Myb. Part I. Myc", Genes Dev. 4:2235–2241.

McKenzie et al., 1998, "Controlled Cytokinin Production in Transgenic Tobacco Using a Copper–Inducible Promoter", Plant Physiol. 116:969–977.

Meijer et al., 1997, "Transcriptional Repression by Oshox1, a Novel Homedomain Leucine Zipper Protein from Rice", Plant J. 11:263–276.

Mett et al., 1993, "Copper–Controllable Gene Expression System for Whole Plants", Proc. Natl. Acad. Sci. USA 90:4567–4571.

Moore et al., 1998, "A transcription activation system for regulated gene expression in transgenic plants", Proc. Natl. Acad. Sci. USA, 90:376–381.

Paz–Ares et al., 1987, "The Regulatory c1 Locus of *Zea mays* Encodes a Protein with Homology to myb Proto–Oncogene Products and with Structural Similarities to Transcriptional Activators", EMBO J. 6:3553–3558.

Picard et al., 1988, "A Moveable and Regulable Inactivation Function within the Steroid Binding Domain of the Glucocorticoid Receptor", Cell 54:1073–1080.

Potrykus et al., 1985, "Molecular and General Genetics of a Hybrid Foreign Gene Introduced into Tobacco by Direct Gene Transfer", Mol. Gen. Genet 199:169–177.

Powell et al., 1998, "Molecular characterization of a Rhodococcus ohp operon", Antoine Van Leeuwenhoek, vol. 74, No. 1–3, pp. 175–188.

Raikhel, 1992, "Nuclear Targeting in Plants", Plant Physiol. 100:1627–1632.

Reich et al., 1986, "Efficient Transformation of Alfalfa Protoplasts by the Intranuclear Microinjection of Ti Plasmids", Bio/Technology 4:1001–1004.

Rensink et al., 1998, "Domains of a Transit Sequence required for in vivo Import in Arabidopsis Chloroplasts", Plant Physiol. 118:691–699.

Röder et al., 1994, "Efficiency of the Tetracyline–Dependent Gene Expression System: Complete Suppression and Efficient Induction of the rolB Phenotype in Transgenic Plants", Mol. Gen. Genet. 243:32–38.

Rossi et al., 1993, "Efficient and Sensitive Assay for T–DNA–Dependent Transient Gene Expression", Plant Mol. Biol. Reporter 11:220–229.

Roth et al., 1991, "C1 and R–Dependent Expression of the Maize Bz1 Gene requires Sequences with Homology to Mammalian myb and myc Binding Sites", Plant Cell 3:317–325.

Salter et al., 1998, "Characterisation of the Ethanol–Inducible alc Gene Expression System for Transgenic Plants", Plant J. 16:127–132.

Schena et al., 1991, "A Steroid–Inducible Gene Expression System for Plant Cells", Proc. Natl. Acad. Sci. USA 88:10421–10425.

Skuzeski et al., 1990, "Analysis of Leaky Viral Translation Termination Codons in vivo by Transient Expression of Improved β–Glucuronidase Vectors", Plant Mol. Biol. 15:65–79.

Sommer et al., 1998, "Specific Induction of Secondary Product Formation in Transgenic Plant Cell Cultures using an Inducible Promoter", Plant Cell Reports 17:891–896.

Tuerck and Fromm, 1994, "Elements of the Maize A1 Promoter Required for Transactivation by the Anthocyanin B/C1 or Phlobaphene P Regulatory Genes", Plant Cell 6:1655–1663.

Twell et al., 1989, "Transient Expression of Chimeric Genes Delivered into Pollen by Microprojectile Bombardment", Plant Physiol. 91:1270–1274.

Vancaneyt et al., 1990, "Construction of an Intron–Containing Marker Gene: Splicing of the Intron in Transgenic Plants and Its Use in Monitoring Early Events in Agrobacterium––Mediated Plant Transformation", Mol. Gen. Genet. 220:245–250.

van Engelen et al., 1995, "pBINPLUS: An Improved Plant Transformation Vector Based on pBIN19", Transgenic Res. 4:288–290.

Varagona et al., 1992, "Nuclear Localization Signal(s) Required for Nuclear Targeting of the Maize Regulatory Protein Opaque–2", Plant Cell 4:1213–1227.

Vieira and Messing, 1982, "The pUC Plasmids, an M13mp7–Derived System for Insertion Mutagenesis and Sequencing with Synthetic Universal Primers", Gene 19:259–268.

Weinmann et al., 1994, "A Chimeric Transactivator Allows Tetracycline–Responsive Gene Expression in Whole Plants", Plant J. 5:559–569.

Wilde et al., 1992, "Control of Gene Expression in Tobacco Cells Using a Bacterial Operator–Repressor System", EMBO J. 11:1251–1259.

* cited by examiner

CONTROL OF GENE EXPRESSION IN EUKARYOTES

1. INTRODUCTION

This invention relates to an inducible gene expression system, particularly but not exclusively eukaryotes, such as plants, for example.

2. BACKGROUND TO THE INVENTION

Manipulation of plants to improve certain characteristics requires the control of expression of foreign or endogenous genes in plant tissues. Such manipulation relies on the availability of mechanisms to control gene expression as required. It is therefore advantageous to have the choice of a variety of different promoters so that the most suitable promoter may be used. A range of promoters is known to be operative within plants.

Within the promoter there are several defined domains which are necessary for the function of the promoter. The first of these domains is located immediately upstream of the structural gene and forms the core promoter region, about 70 base pairs immediately upstream of the genes. This region contains the CAAT and TATA boxes and represents a transcription initiation sequence which defines the transcription start site for the gene. A series of regulatory sequences upstream of the core promoter sequence constitute the remainder of the promoter. The regulatory sequences determine the expression levels, the spatial and temporal pattern of expression and possible expression under inductive conditions.

The control of expression of heterologous genes in plant cells is important for the successful genetic manipulation of plants to alter and/or improve phenotypic characteristics. Promoters and/or regulatory sequences from bacteria, viruses, fungi and plants have been used to control gene expression in plants. In some cases it will be desirable to control the time and/or extent of the expression of introduced genetic material in plants, plant cells or tissue. The ability to regulate the expression of transgenes provides several important advantages: (1) regulation of expression of gene(s) that might interfere with the transformation and regeneration process (Roeder et al., 1994, McKenzie et al., 1998), (2) reversible control of gene expression at a specific time (e.g. manipulation of carbon metabolism by Caddick et al., 1998 and secondary product formation by Sommer et al., 1998), (3) control of growth and development (e.g. flowering, plant fertility, cell wall formation), (4) control of genes that respond to environmental signals (e.g. attack by pathogens, such as, for example, nematodes, arachnids or aphids), (5) expression of selectable marker genes and (6) expression of recombinase proteins at specific time points. Each of these applications can use the inducible gene expression system and novel sequences of the present invention.

2.1 Known Regulatable Gene Expression Systems in Plants

A few plant genes are known to be induced by a variety of internal and external factors including plant hormones, heat/cold shock, chemicals, pathogens, lack of oxygen and light. Few of these systems have been described in detail.

Ideally a chemically inducible activating promoter in a 5' regulatory region should have low background activity in the absence of an inducer and demonstrate high expression in the presence of an inducer. A chemically inducible repressing promoter in a 5' regulatory region should have low background activity in the presence of an inducer and demonstrate high expression in the absence of an inducer. The activator/repressor should also only allow control of the transgene. This renders the use of most endogenous promoters unsuitable and favors the use of those better characterized regulatory elements of model organisms distant in evolution, such as yeast, E. coli, Drosophila or mammalian cells, that respond to signals that are usually not encountered in higher plants. These characteristic regulatory elements are, however, less advantageous in their operation than the system proposed in the present invention.

On this basis, two different concepts of gene control can be realized, namely promoter-repressing systems and promoter-activating systems.

2.2 Promoter-repressing Systems

The repression principle is based on the sterical interference of a protein with the proteins important for transcription. It is a common mechanism in bacteria, for example LexA, Lac and Tet, but occurs much less frequently in higher eukaryotes. Two bacterial repressor/operator systems (Lac and Tet) have been used to control the activity of promoters transcribed by RNA polymerase II. Gatz and Quail (1988) taught the use of the Tn10-encoded Tet repressor/operator with a cauliflower mosaic virus 35S promoter in a transient plant expression system. Frohberg et al., (1991) and Gatz et al., (1991, 1992) characterised the effect of placing Tet operator sequences at different positions in a CaMV 35S promoter. U.S. Pat. No. 5,723,765 and International Patent Application, Publication No. WO 96/04393 disclosed use of the Tet repressor system for the inducible expression of the Cre recombinase in transgenic plants. Wilde et al., (1992) used the Lac repressor/operator system for the inducible expression from a chlorophyll a/b binding protein promoter in protoplasts of stably transformed plants.

2.3 Promoter-activating Systems

A second approach for the construction of a chemically inducible system is to use transcriptional activators from higher eukaryotes. The mammalian glucocorticoid receptor (GR), which activates eukaryotic expression only in the presence of steroids has been used by Picard et al., (1988) in *Schizosaccharomyces pombe*. Schena et al., (1991) have shown that transcription from a target promoter containing GR-binding sites was strictly dependent on the addition of steroids in transiently transformed tobacco cells. Lloyd et al., (1994) have used a fusion of the steroid receptor protein with the maize transcription factor R to complement an Arabidopsis mutant in a steroid inducible fashion. Aoyama and Chua (1997) disclosed use of a chimeric transcription factor consisting of the DNA-binding domain of the yeast transcription factor Gal4, the transactivating domain of the herpes viral protein Vp16 and the receptor domain of the rat glucocorticoid receptor to induce the expression of a reporter gene in transgenic plants through the application of steroids.

International Patent Application, Publication No. WO 96/27673 describes the use of a steroid receptor system in transgenic plants using chimeric GR receptors with Vp16 and C1 transcriptional activation domains and Gal4 DNA binding domains.

Another eukaryotic ligand-dependent activator is Ace1, a copper-dependent transcriptional activator from yeast. Mett et al., (1993) have shown that Ace1 regulates the expression of a suitable target promoter (CaMV 35S-90 bp promoter containing the Ace1 binding site) in transgenic plants. McKenzie et al., (1998) used a similar system (Ace1 binding sites with a CaMV 35S-40 bp promoter) to investigate copper-inducible activation of the ipt gene in transgenic tobacco.

AlcR is the specific activator of the *Aspergillus nidulans* ethanol-utilisation pathway, mediating the induction of its own transcription and that of the structural genes alcA and aldA. AlcR is a DNA binding protein that recognises specific binding sites in structural gene promoters (Kulmburg et al., 1992, Fillinger & Felenbok 1996). Felenbok (1991) used the AlcA-AlcR system for the expression of recombinant proteins in Aspergilli. The ethanol inducible gene switch was used by Caddick et al., (1998) to manipulate carbon metabolism in transgenic plants and also by Salter et al (1998) to examine the induction of a chloramphenicol acetyltransferase (CAT) reporter construct by ethanol. This system has also been used in International Patent Application, Publication No. WO 93/21334 for the inducible activation of a chimeric alcA/CaMV 35S promoter in transgenic plants.

2.4 Fusion Proteins

A third strategy is based on the construction of fusion proteins between transcriptional transactivation domains and bacterial repressor proteins such as the Lac and the Tet repressor. Weinmann et al (1994) used a tetracycline controlled transactivator (the virus protein 16 (Vp 16) activation domain fused to the Tet repressor protein) to switch off expression of a GUS transgene in transgenic plants in the presence of the inducer.

2.5 Mutant Repressor Proteins

A fourth strategy is based on the creation of mutant repressor proteins that bind to DNA only in the presence of the inducer. Gossen et al., (1995) have developed a reverse Tet repressor protein that binds to DNA only in the presence of the inducer and used this system successfully in mammalian cells.

Very recently, in International Patent Application No. PCT/GB98/01893 work was carried out at Rhodococcus sp. V49 in respect of biosensor materials and methods of uses thereof. Rhodococcus sp. V49 (formerly *Nocardia corallina*) ATCC 19070 is a non-acid fast, gram-positive rod-shaped soil bacterium. It can use a range of monoaromatic compounds, including 3-(2-hydroxyphenyl)propionic acid (orthohydroxyphenylpropionic acid, OHP) and 2-hydroxy cinnamic acid as the sole carbon source. It is also able to grow on n-hexadecane, benzene and toluene. The international patent application, the subject matter of which is to be deemed incorporated herein, discloses the nucleotide sequence of the 7.5 kb OHP operon from Rhodococcus sp. V49.

The polypeptide encoded by the ohpR gene shows a strong sequence similarity throughout its length to a number of bacterial transcriptional regulators from the GntR family (Haydon & Guest 1991). The strong sequence similarity indicates that ohpR encodes a prokaryotic transcriptional regulator.

International Patent Application No. PCT/GB98/01893 discloses the use of genetically manipulated mycolic acid bacteria cells solely as sensors for analytes in environmental samples. The potential other uses and modifications of the novel nucleotide sequences described in the present invention are nowhere contemplated in PCT/GB98/01893.

3. SUMMARY OF THE INVENTION

The present invention provides a method of controlling eukaryotic gene expression comprising transforming a eukaryotic cell with an inducible gene expression system, the gene expression system comprising a first nucleotide sequence comprising a 5' regulatory region operably linked to a nucleic acid sequence which encodes a regulator polypeptide and an untranslated 3' termination sequence, and a second nucleotide sequence comprising a 5' regulatory region operably linked to a nucleic acid sequence which is a coding or non-coding sequence, the expression of the nucleic acid sequence of the second nucleotide sequence being controlled by the regulator polypeptide of the first nucleotide sequence using an inducer, the inducer thereby causing modulation of expression of the nucleic acid sequence of the second nucleotide sequence, and the nucleotide sequence of the regulator polypeptide and/or the 5' regulatory region, or parts thereof, of the second nucleotide sequence being isolated from a prokaryote source.

The present invention also provides a chimeric gene comprising a first nucleotide sequence comprising a 5' regulatory region operably linked to a nucleic acid sequence which encodes a regulator polypeptide and an untranslated 3' termination sequence, and a second nucleotide sequence comprising a 5' regulatory region operably linked to a nucleic acid sequence which is a coding or non-coding sequence, the expression of the nucleic acid sequence of the second nucleotide sequence being controlled by the regulator polypeptide of the first nucleotide sequence using an inducer, the inducer thereby causing modulation of expression of the nucleic acid sequence of the second nucleotide sequence, and the nucleotide sequence of the regulator polypeptide and/or the 5' regulatory region or parts thereof of the second nucleotide sequence being isolated from a prokaryote source.

Advantageously, the regulator polypeptide comprises one or more domains, which domains may be a ligand binding domain, a nucleic acid binding domain, a transactivation domain, a targeting domain, a silencing/repressing domain or a dimerization domain. The regulator sequence may thus comprise a chimeric gene of different sequences.

3.1 Definitions

In order to provide a clear and consistent understanding of the specification and terms used herein, the following definitions are provided:

3.1.1 Regulatable Gene

A gene containing at least one regulatable nucleic acid sequence and at least one associated coding or non-coding nucleic acid sequence. The genes may be of natural, synthetic or partially natural/partially synthetic origin.

3.1.2 Inducer

An elemental or molecular species which controls, for example, initiates, terminates, increases or reduces, by direct or indirect action, the activity of a regulatable nucleic acid sequence in a system in which the inducer is not normally found in an active form in an amount sufficient to effect regulation of transcription, to the degree and at the time desired, of transcribable nucleic acid sequence associated with the regulatable nucleic acid sequence.

This terminology embraces situations in which no or very little inducer is present at the time transcription is desired or in which some inducer is present but increased or decreased regulation is required to effect more or less transcription as desired. Thus, if the system containing the regulatable nucleic acid sequence is, for example, a transgenic plant, an inducer is a species not naturally found in the plant in an amount sufficient to effect regulation/modulation, and thus transcription of an associated gene, to the desired degree at the time desired.

By "direct action" it is intended that the inducer action results from the direct interaction between the inducer and the nucleic acid sequence. By "indirect action" it is meant that the inducer action results from the direct interaction between the inducer and some other endogenous or exogenous component in the system, the ultimate results of that direct interaction being activation or suppression of the activity of the nucleic acid sequence. By "active form" it is intended that the inducer be in a form required to effect control.

3.1.3 Regulator Polypeptide

This term as used herein refers to polypeptides which modulate the expression of a target gene (the nucleic acid sequence of the second nucleotide sequence of the present invention) in response to an inducer. The regulator polypeptide may comprise one or more of a ligand binding domain, a nucleic acid binding domain, a transactivation domain, a targeting domain, a silencing/repressing domain or a dimerization domain.

3.1.4 Chimeric Sequence or Gene

A nucleic acid sequence containing at least two parts, e.g. parts derived from naturally occurring nucleic acid sequences which are not associated in their naturally occurring states, or containing at least one part that is of synthetic origin and not found in nature.

3.1.5 Coding Sequence

A nucleic acid sequence which, when transcribed and translated, results in the formation of a polypeptide.

3.1.6 Non-coding Sequence

A nucleic acid sequence which is not transcribed and translated, resulting in the formation of a polypeptide when associated with a particular coding nucleic acid sequence. Thus, for example, a sequence that is non-coding when associated with one coding sequence may actually be coding when associated with another coding or non-coding sequence.

3.1.7 Plant Tissue

Any tissue of a plant in planta or in culture. This term includes, but is not limited to, whole plants, plant cells, plant organs, plant seeds, protoplasts, callus, cell culture and any groups of plant cells organized into structural and/or functional units. The use of this term in conjunction with, or in the absence of, any specific type of plant tissue as listed above or otherwise embraced by this definition is not intended to be exclusive of any other type of plant tissue.

3.1.8 Modulation

The increasing or decreasing of the level of expression of a gene or the level of transcription of a nucleic acid sequence. The definition is not intended to embrace any particular mechanism.

4. DESCRIPTION OF THE FIGURES

In order that the invention may be easily understood and readily carried into effect, reference will now be made, by way of example, to the following diagrammatic drawings, wherein.

Figure 6:
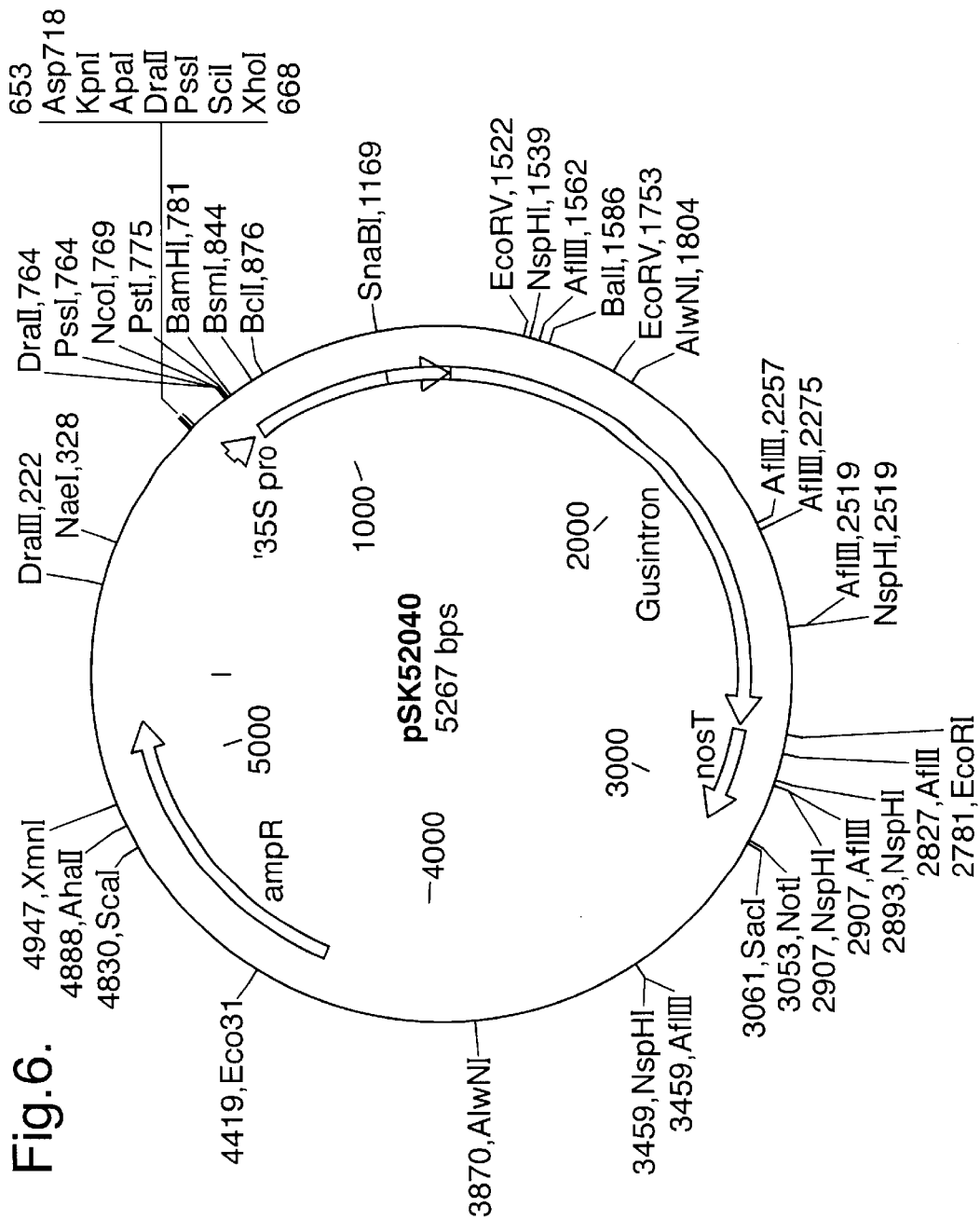
Figure 7:
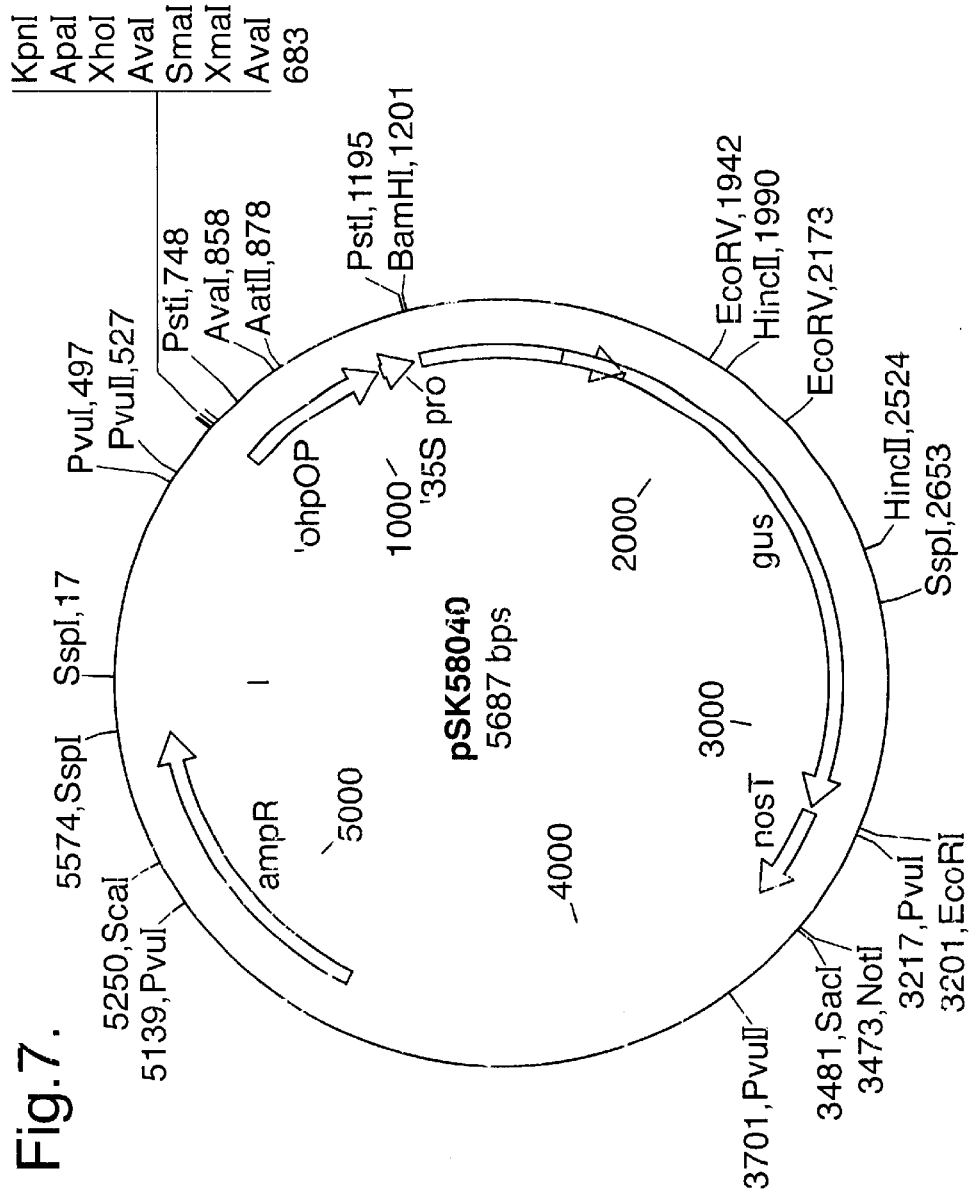
Figure 8:
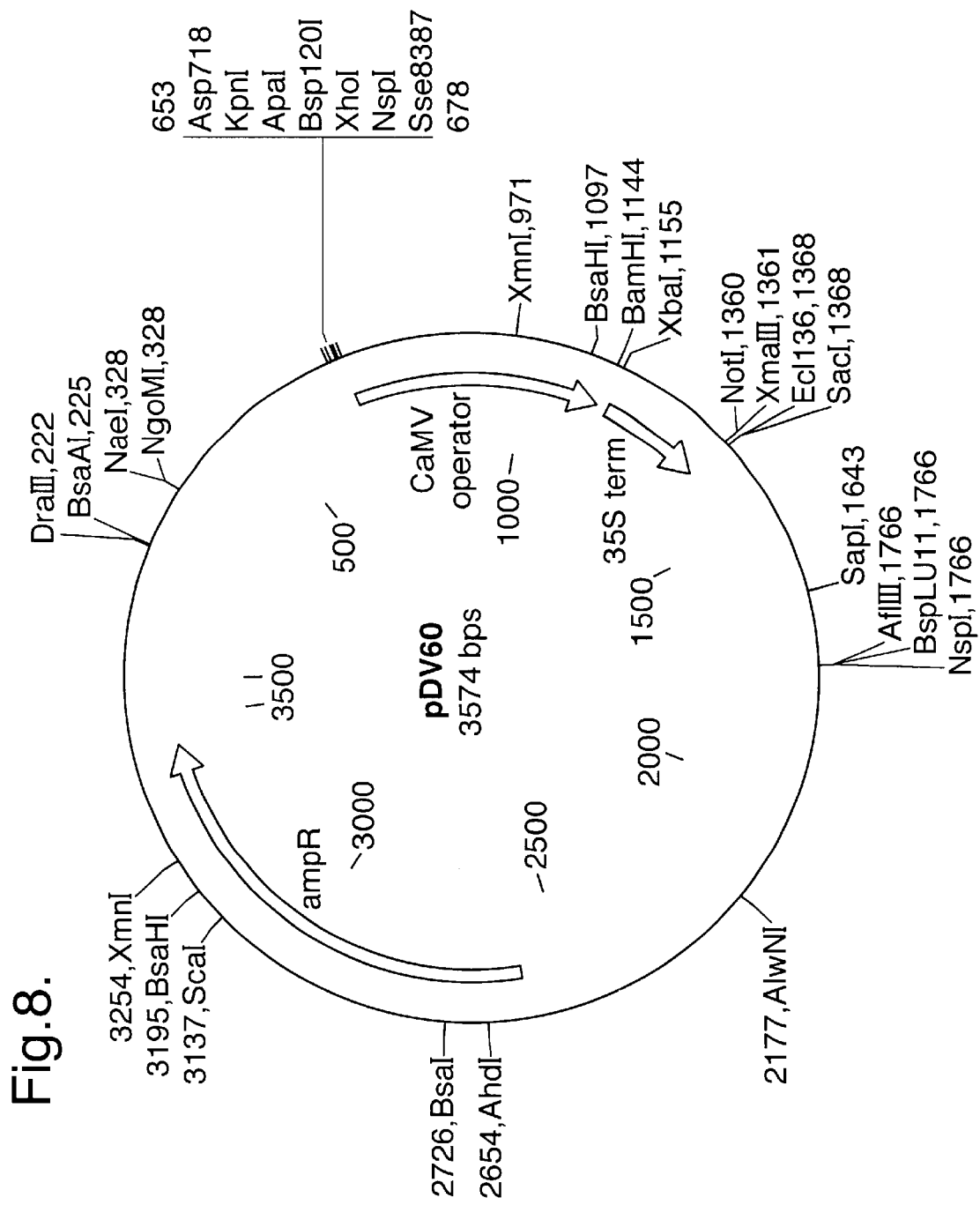
Figure 9:
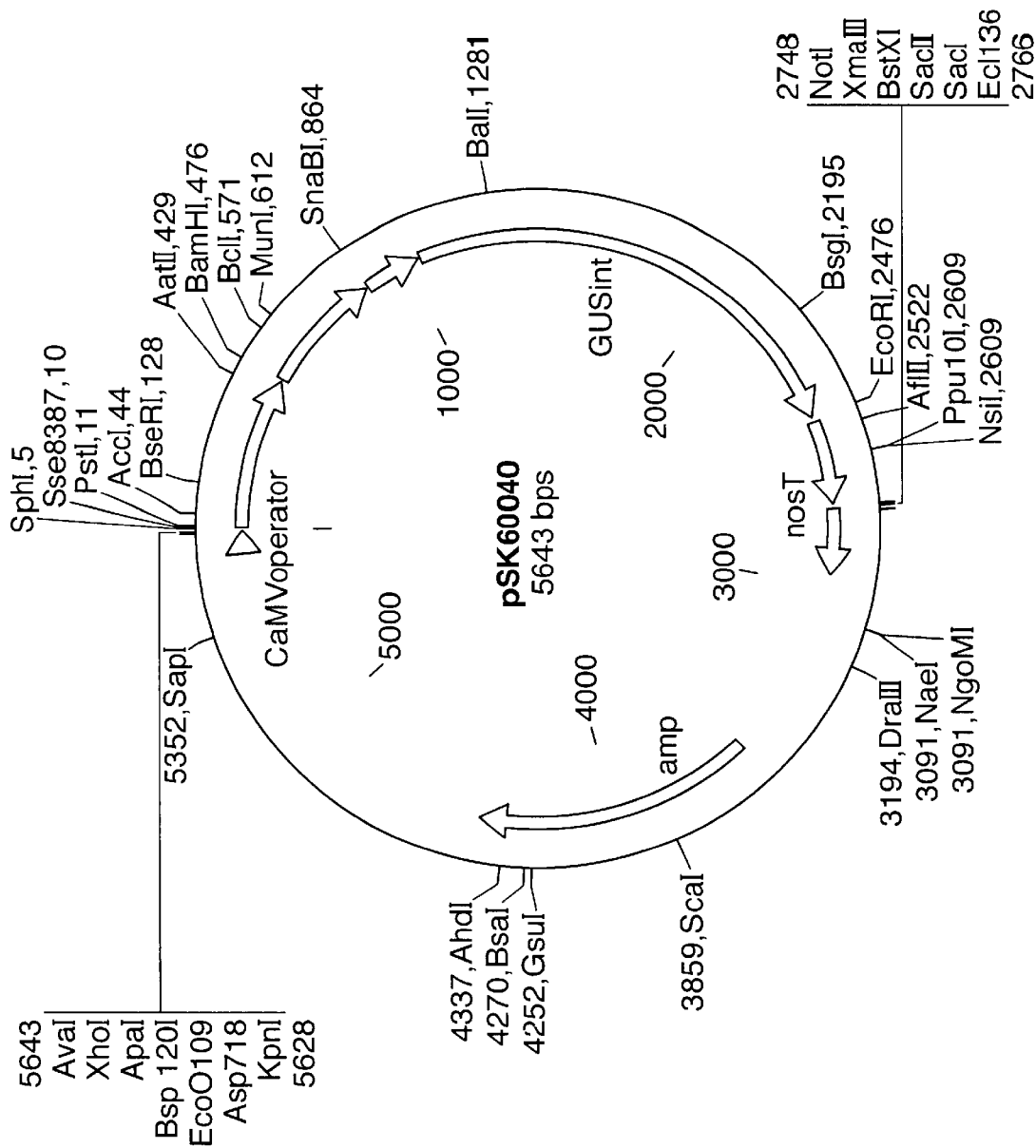
Figure 10:
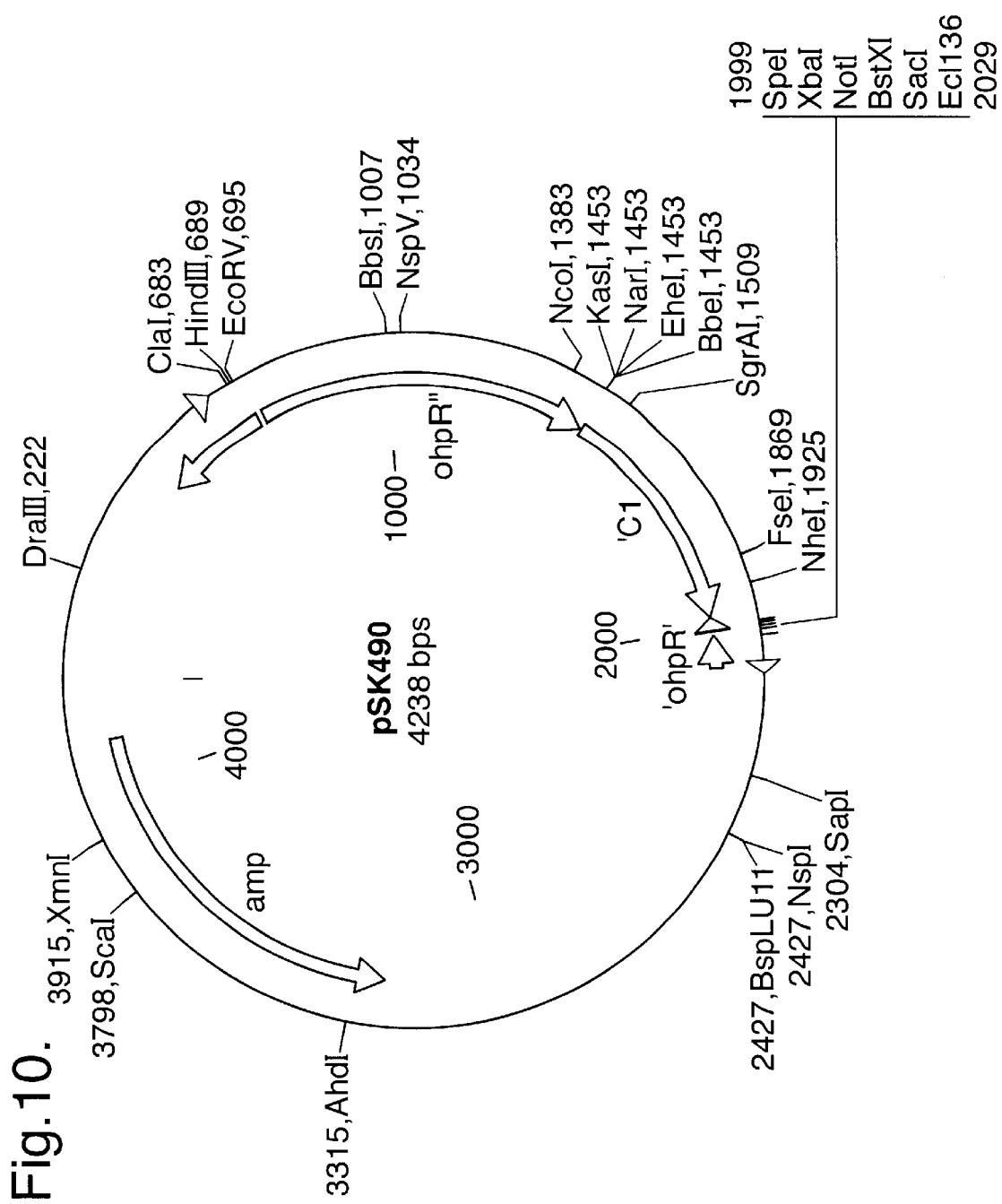
Figure 11:
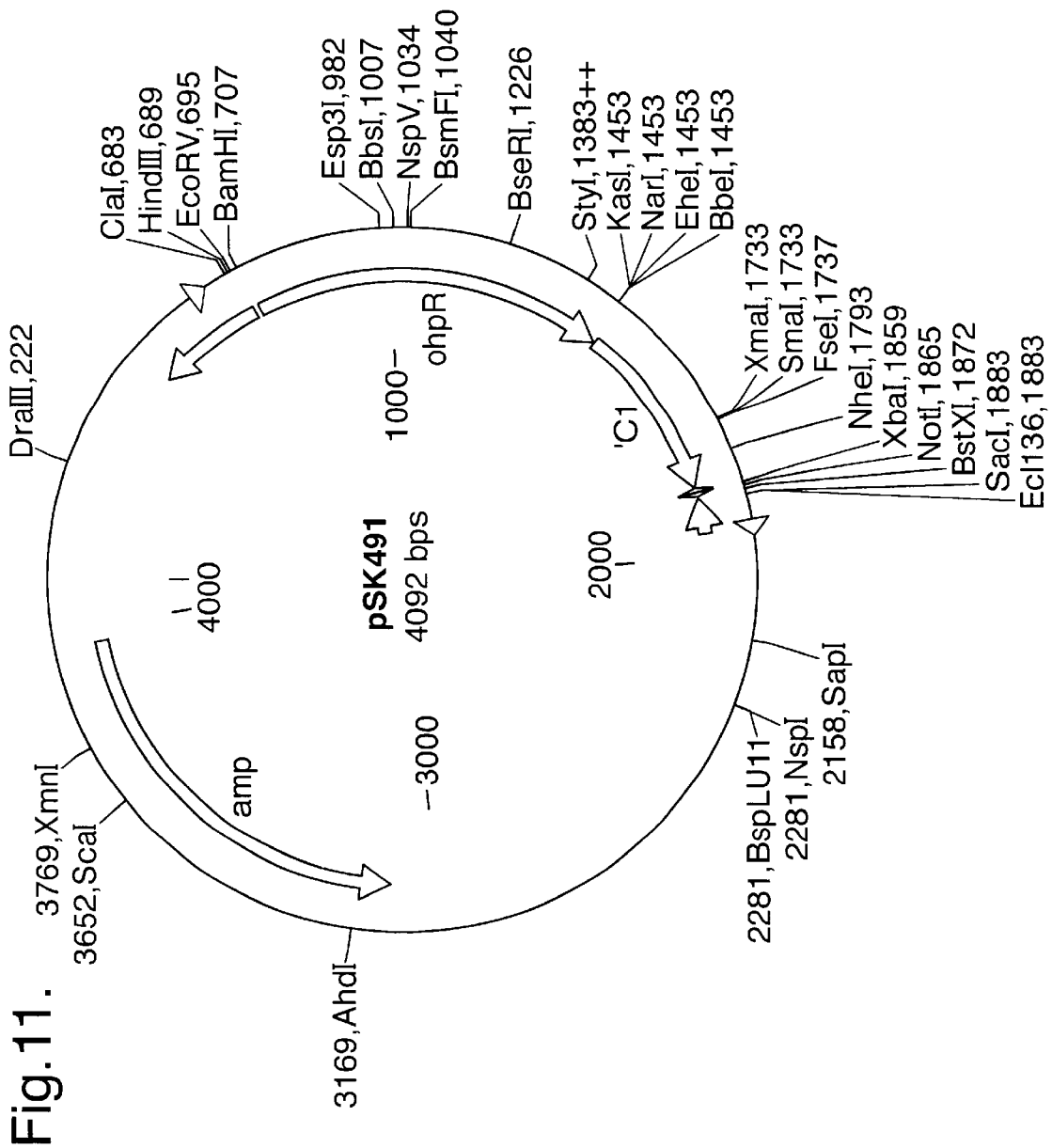

FIG. 6 shows a schematic diagram of the plasmid pSK58040 as used in the present invention. The plasmid contains the ohp operator from nucleotide 1036 to nucleotide 1449 of SEQ ID NO: 1 inserted in plasmid pSK52040 into the XhoI site upstream of the CaMV 35S-90 bp core promoter. Downstream of the CaMV 35S core promoter are located a GUS intron and a nos terminator;

FIG. 7 shows a schematic diagram of plasmid pDV35S1 as used in the present invention. The plasmid contains the CaMV 35S promoter and the CaMV 35S terminator in pBluescript;

FIG. 8 shows a schematic diagram of plasmid pDV60 as used in the present invention. The plasmid contains the chimeric promoter of SEQ ID NO: 19, and the CaMV 35S terminator in pBluescript. The chimeric promoter in Seq. ID. 19 contains a 36 bp region of the ohp operon (from nucleotide 1225 to nucleotide 1260 of SEQ ID NO: 1) inserted into the CaMV35S promoter at nucleotide—21;

FIG. 9 shows a schematic diagram of plasmid pSK60040 as used in the present invention. The plasmid contains the chimeric promoter described in FIG. 8 above (Seq. ID. 19), a GUS intron (Vancanneyt et al., 1990) and a nos terminator in pBluescript;

FIG. 10 shows a schematic diagram of plasmid pSK-490 as used in the present invention. The plasmid contains the chimeric regulator being a translational fusion between the ohpR coding sequence (nucleotide 295 to nucleotide 1035 of SEQ ID NO: 1) and part of the C1 cDNA (from the NarI at nucleotide 536 to the end of the coding region at nucleotide 839, amino acids 179 to 279 of the C1 protein) inserted into pBluescript between the HindIII and Not I sites;

FIG. 11 shows a schematic diagram of plasmid pSK491 as used in the present invention. The plasmid contains the chimeric regulator being a translational fusion between the ohpR coding sequence (nucleotide 295 to nucleotide 1035 of SEQ ID NO: 1) and part of the C1 cDNA (from the PstI site at nucleotide 674 to the end of the coding region at nucleotide 839, amino acids 219 to 279 of the C1 protein) inserted into pBluescript between the HindIII and Not I sites.

Figure 12:
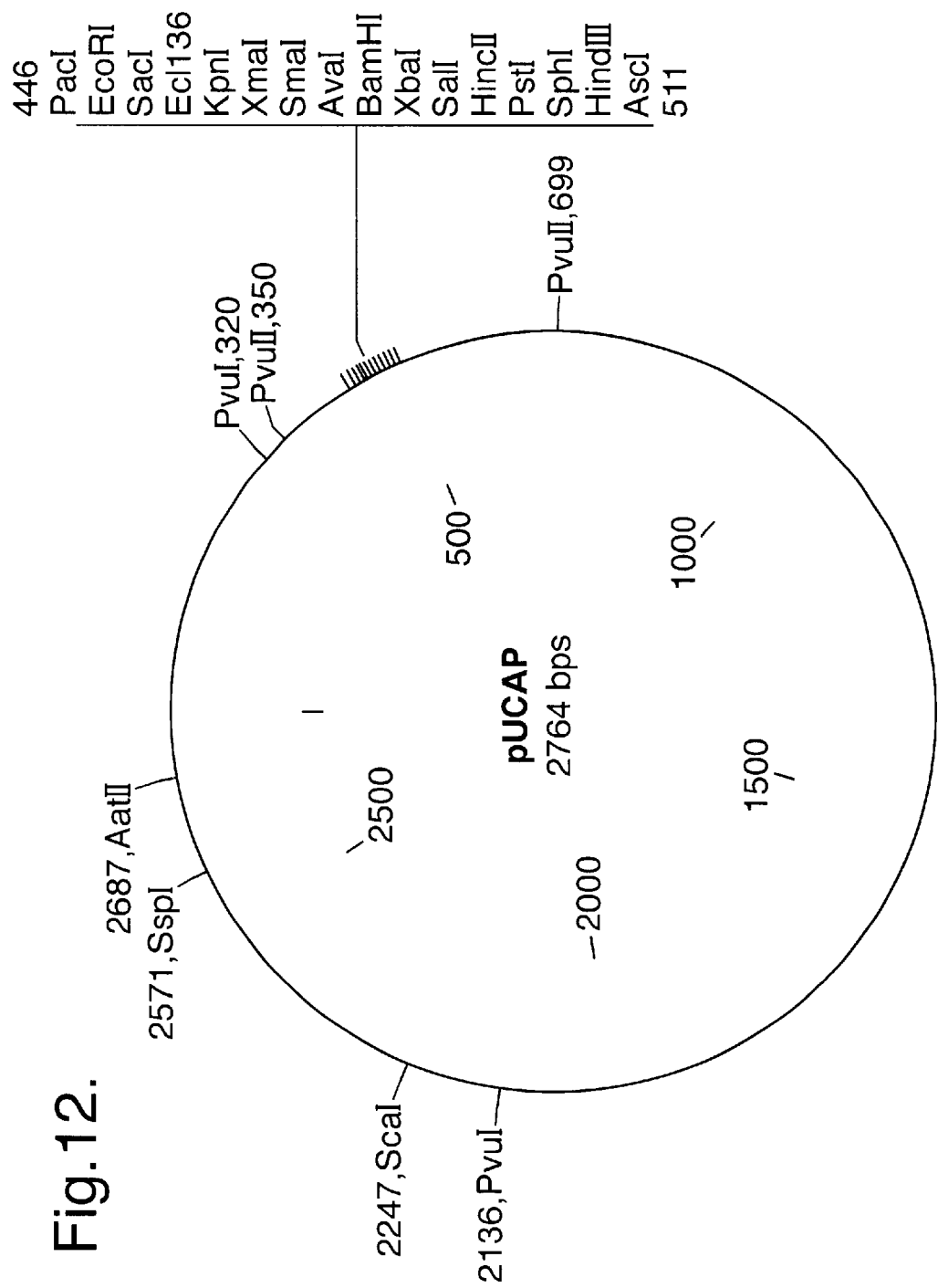
Figure 13:
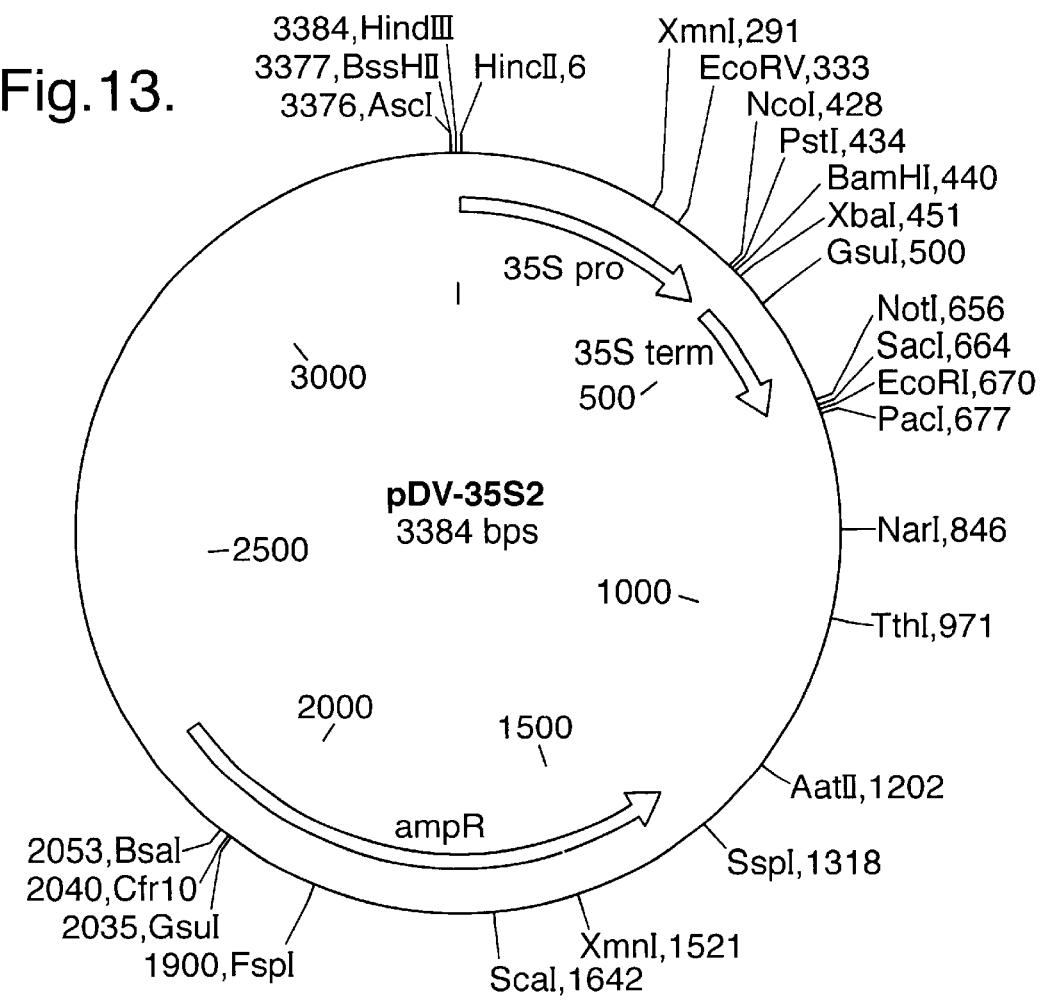
Figure 14:
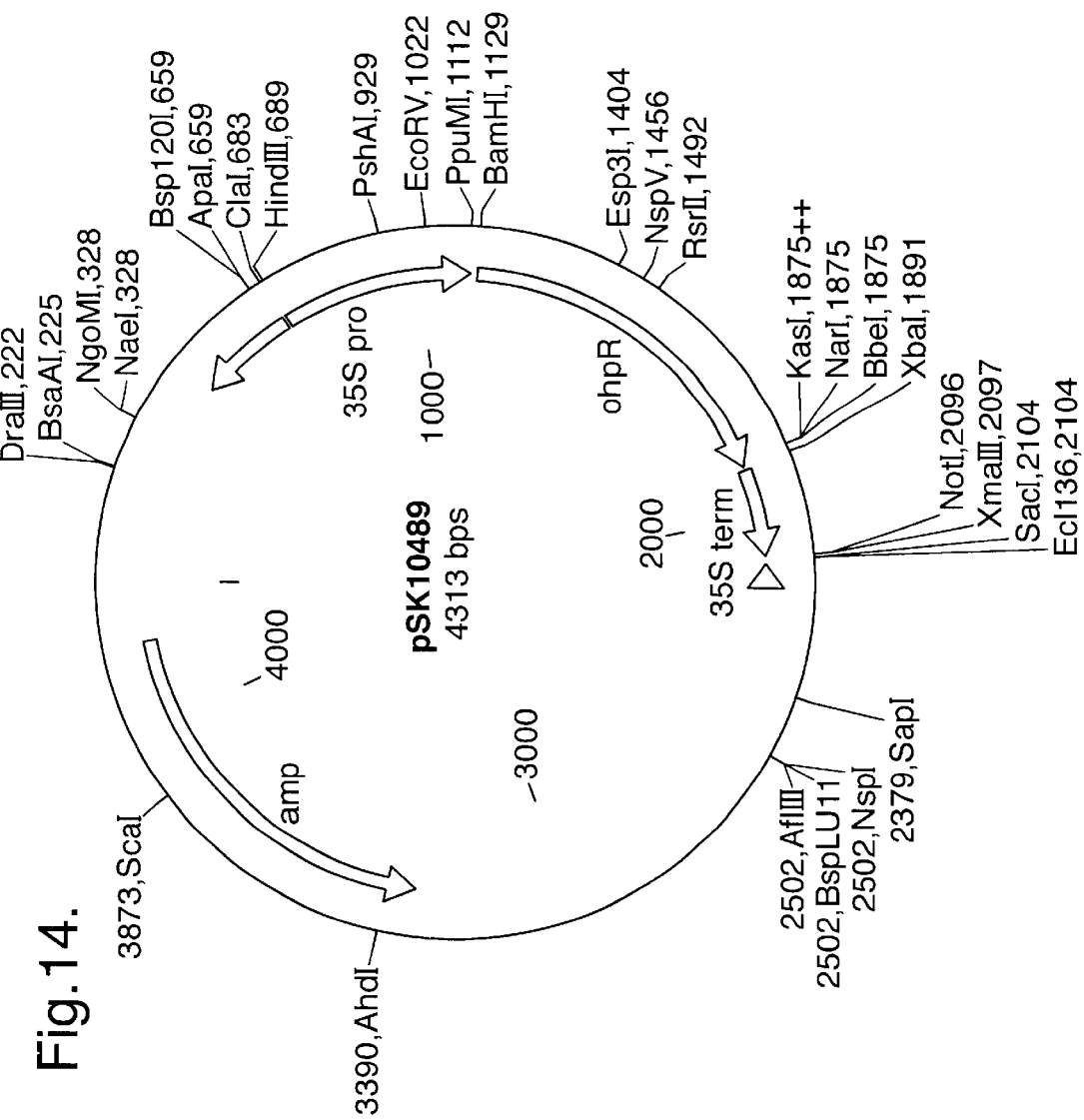
Figure 15:
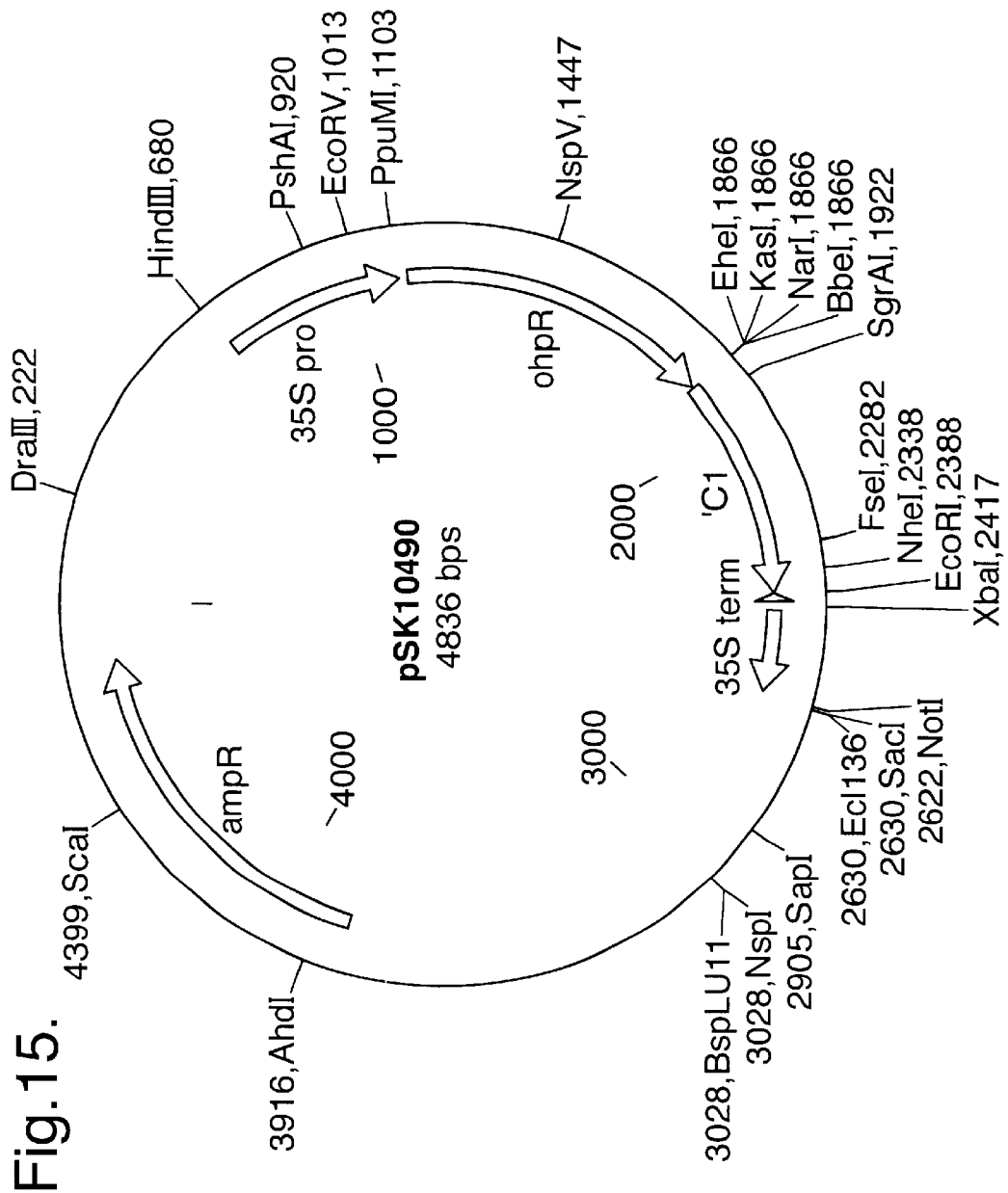
Figure 16:
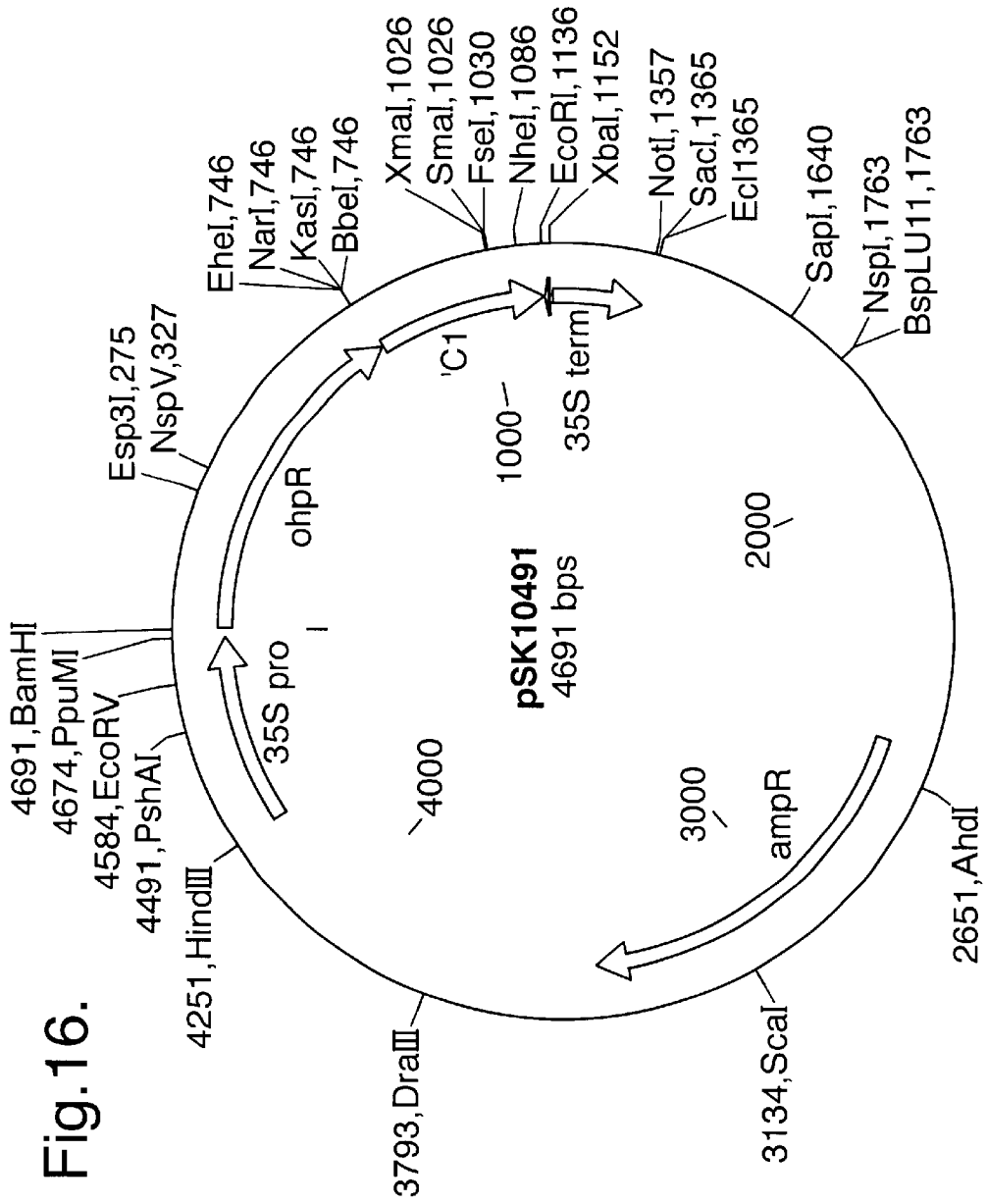
Figure 17:
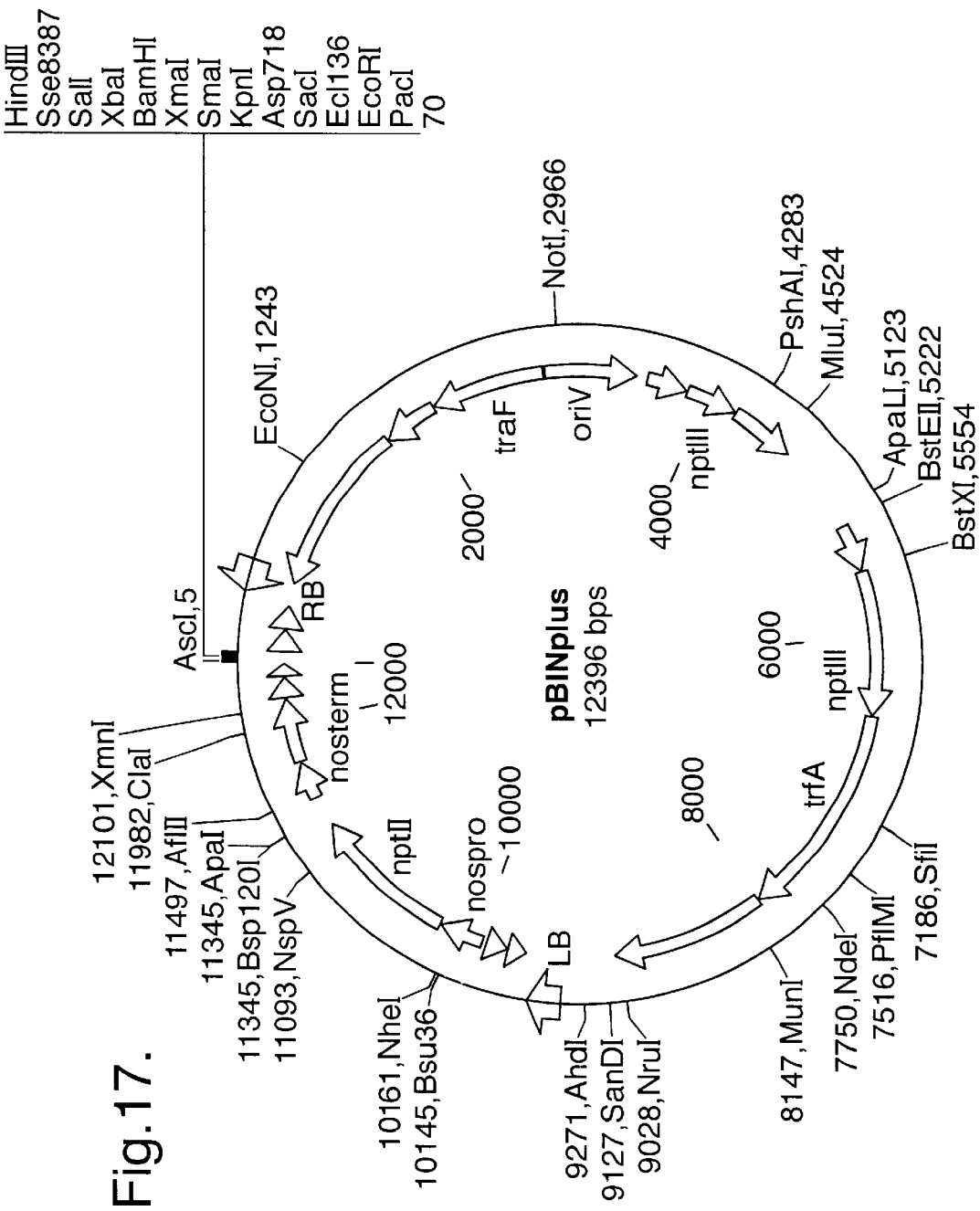
Figure 18:
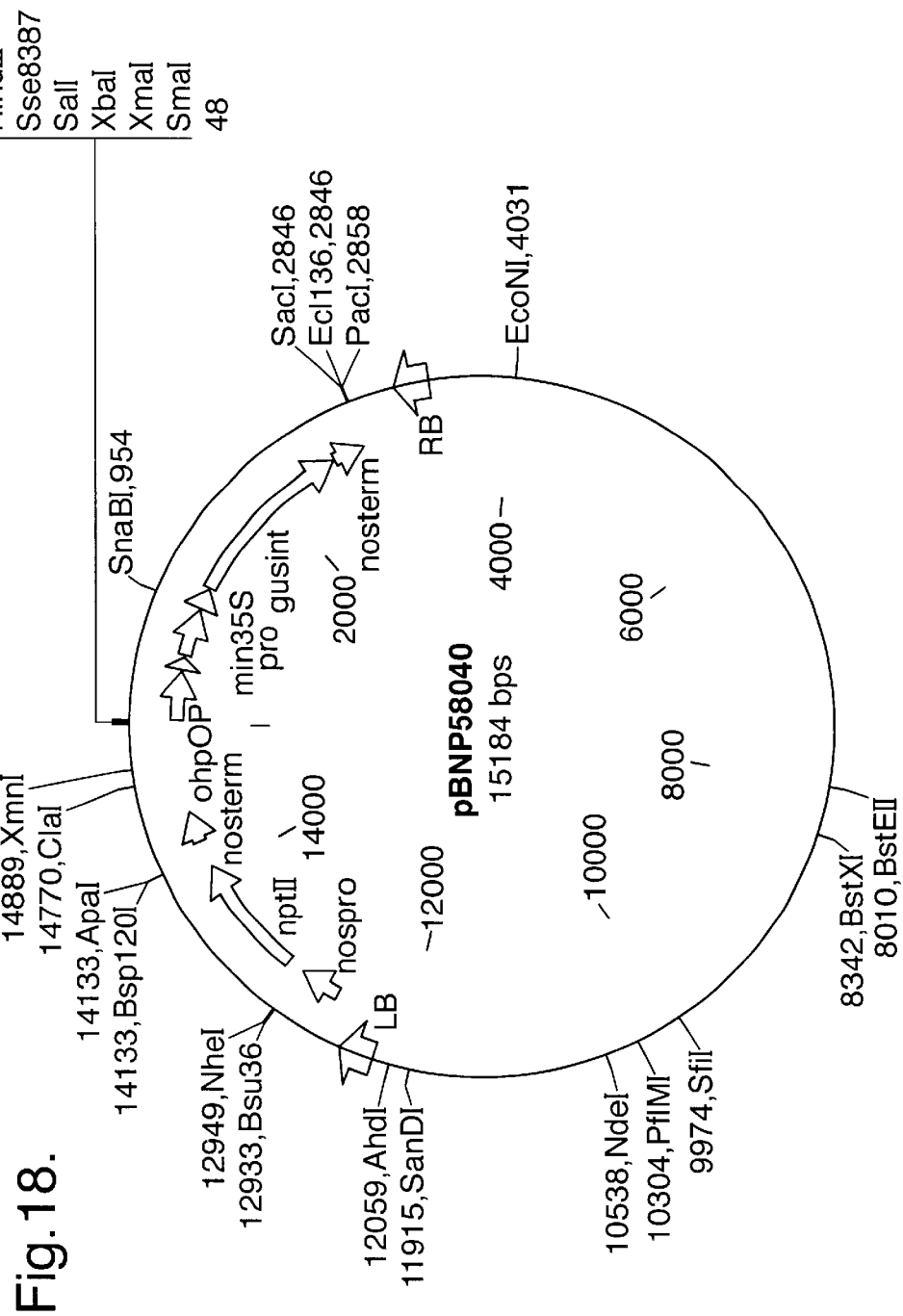
Figure 19:
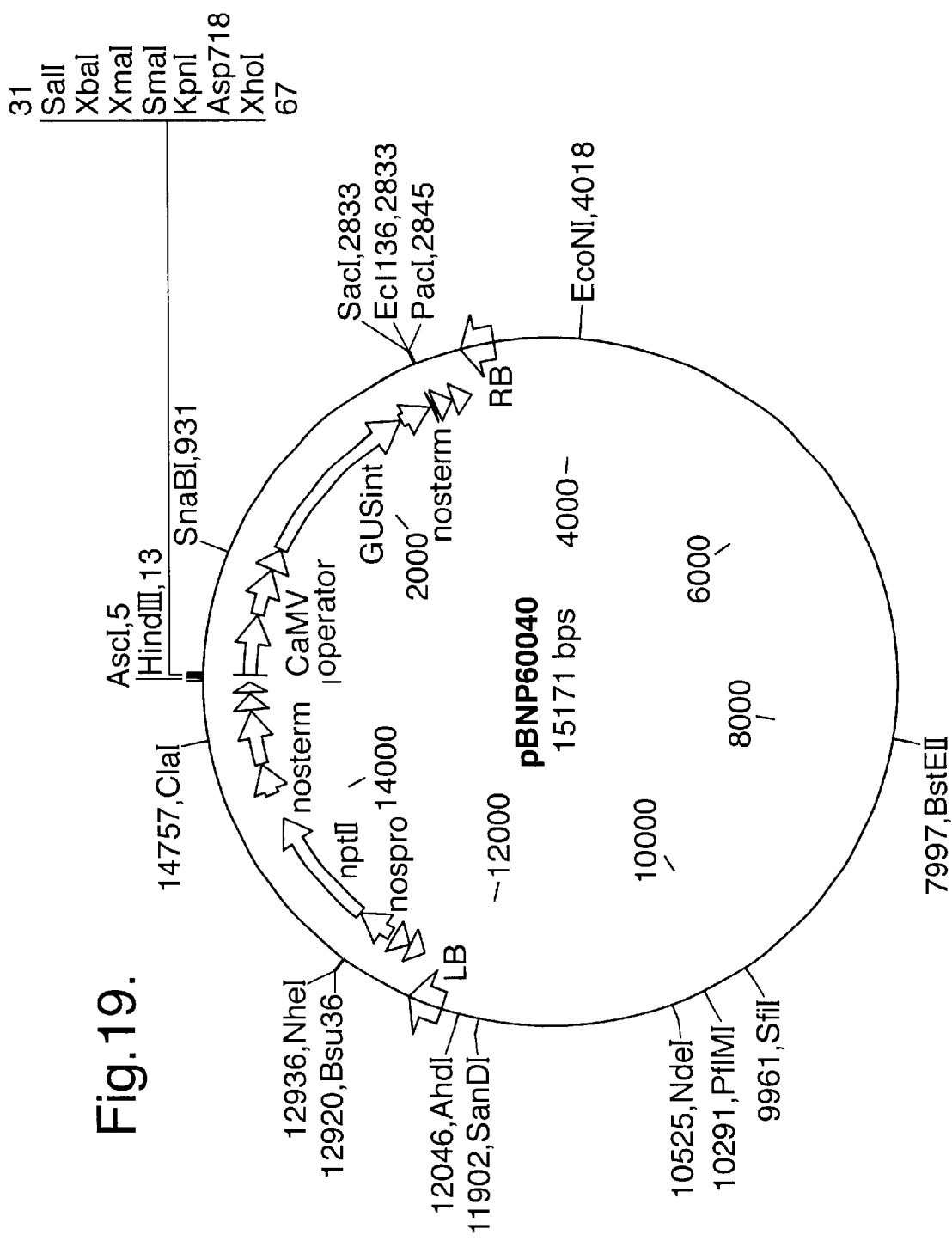
Figure 20:
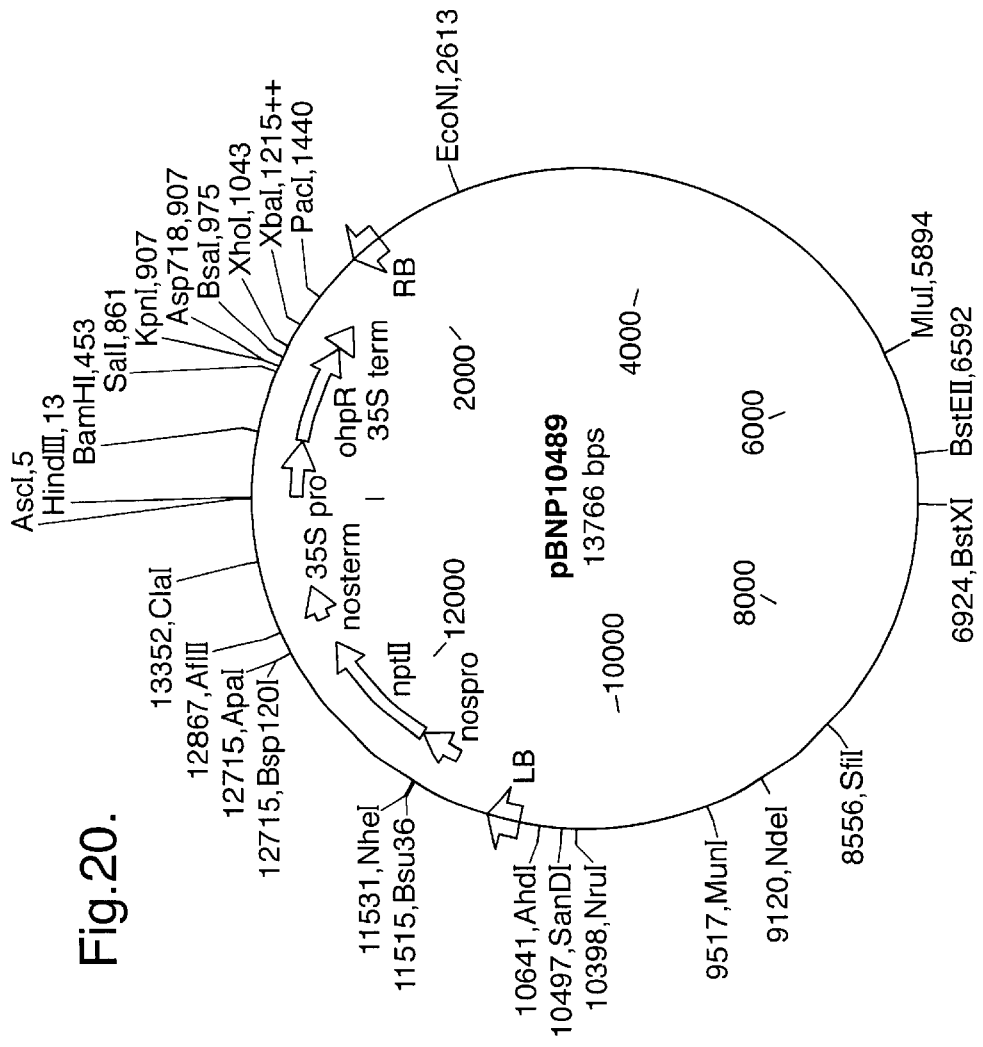
Figure 21:
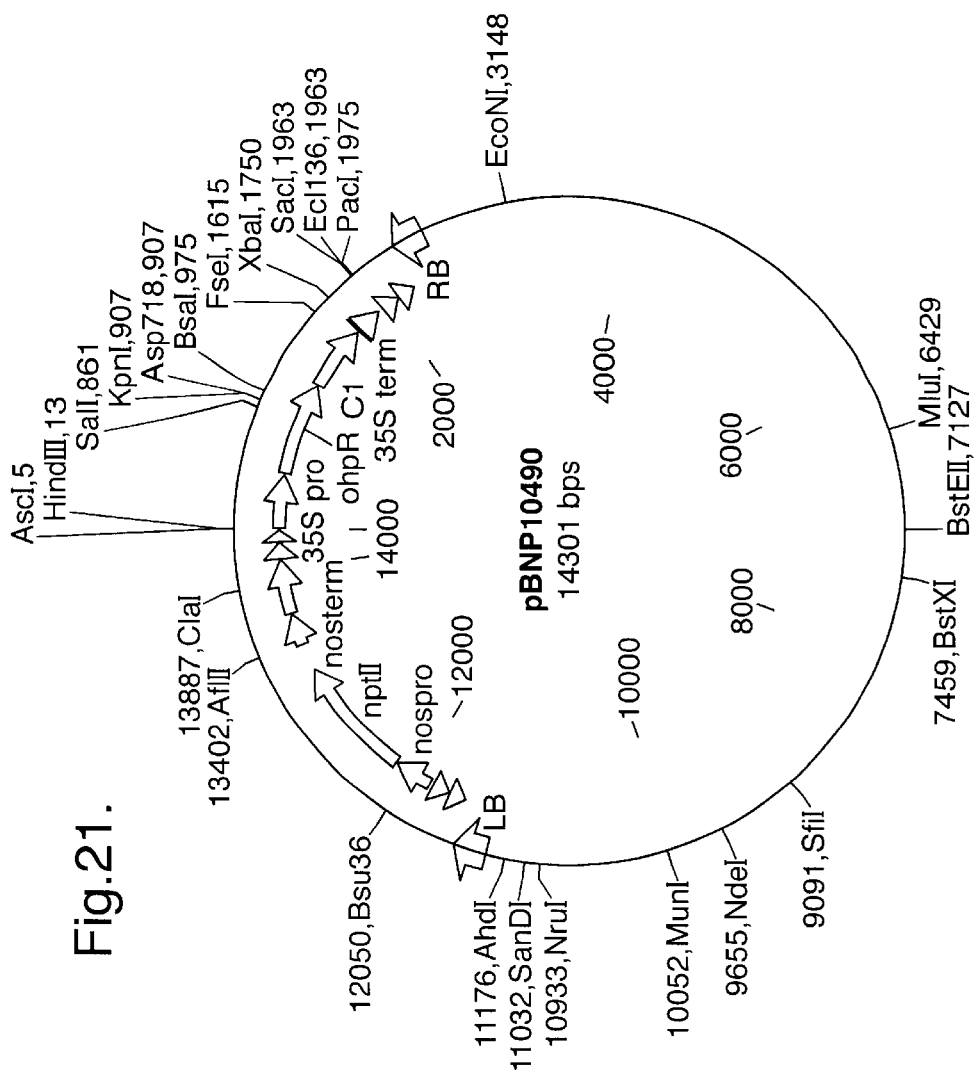
Figure 22:
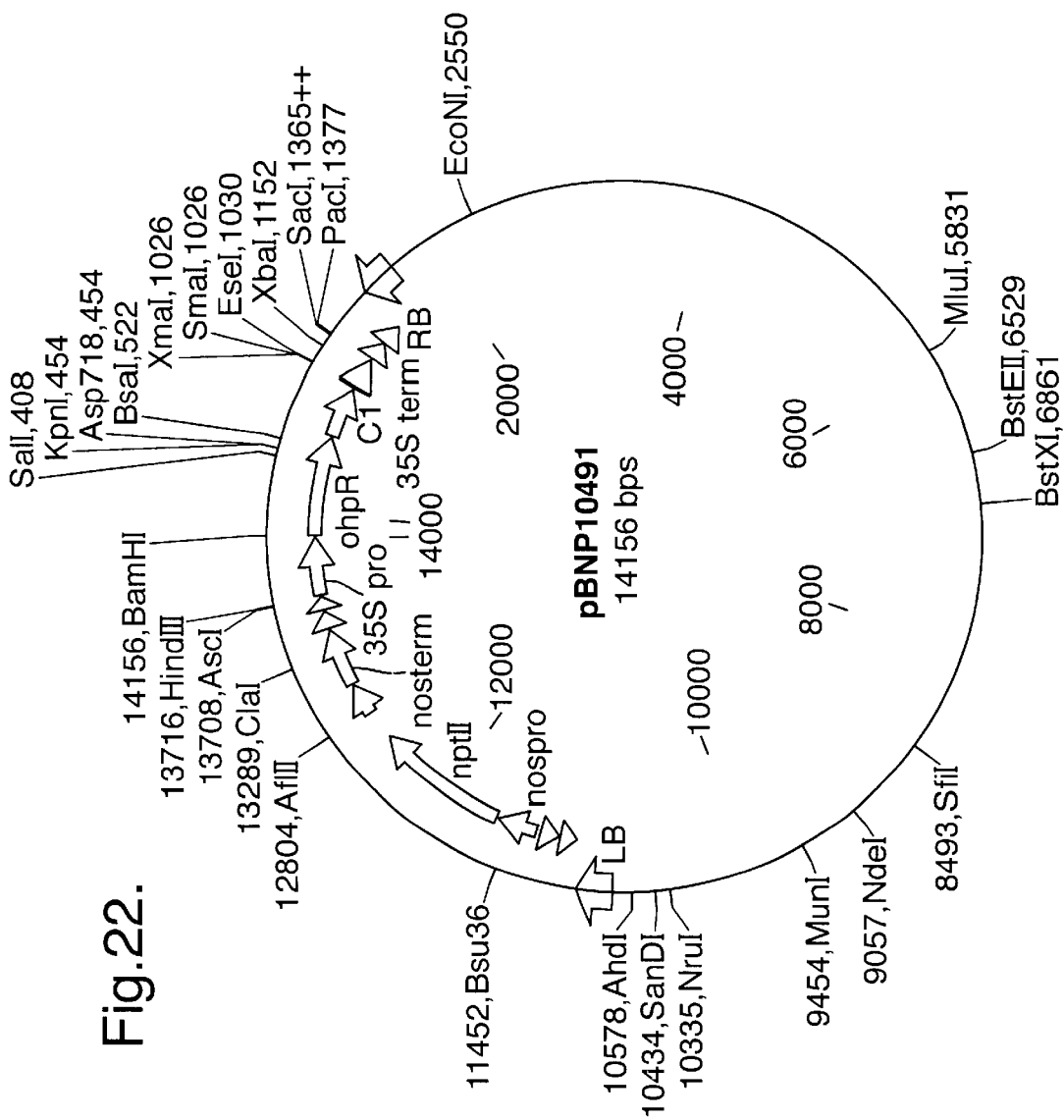
Figure 23:
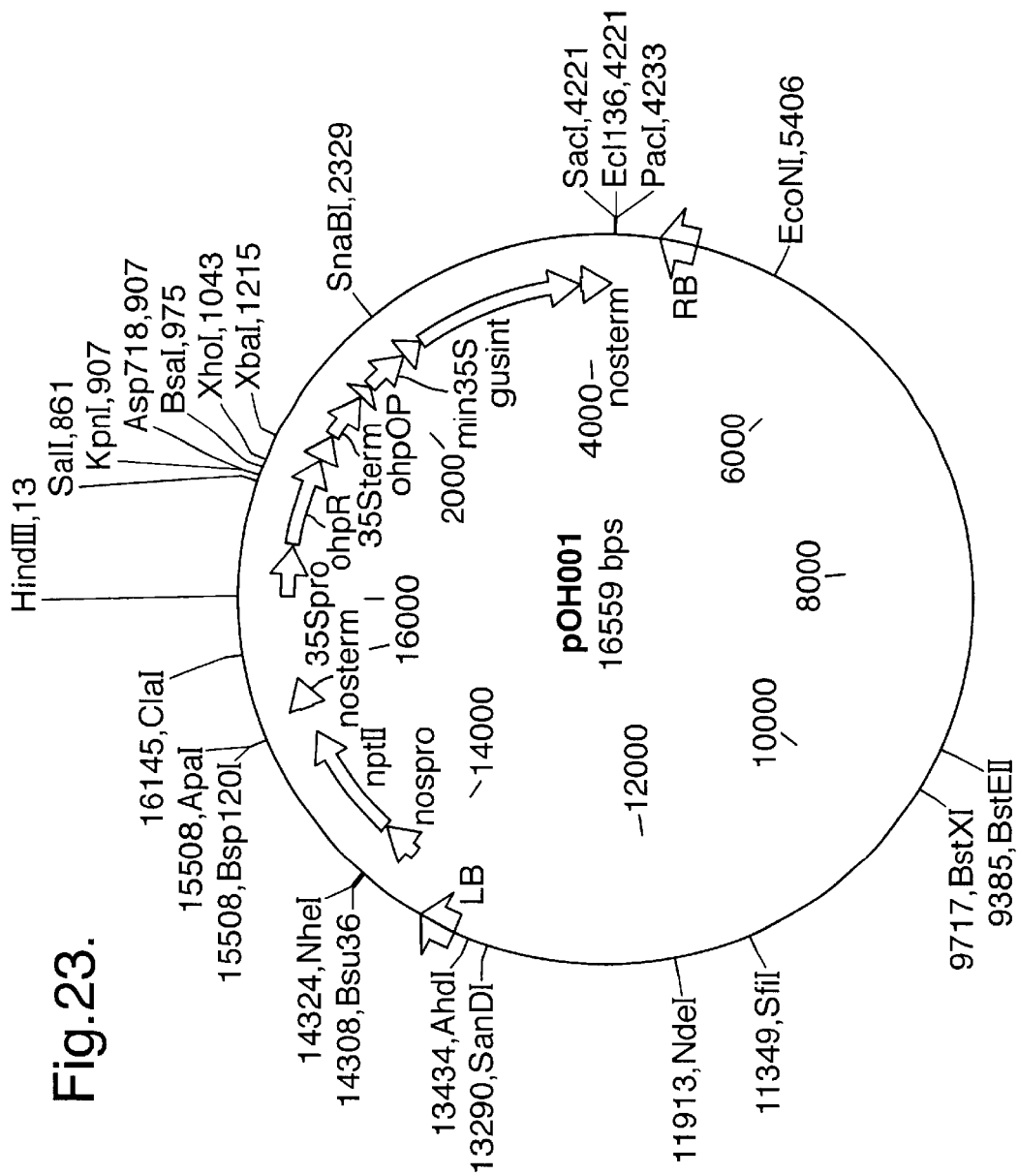
Figure 24:
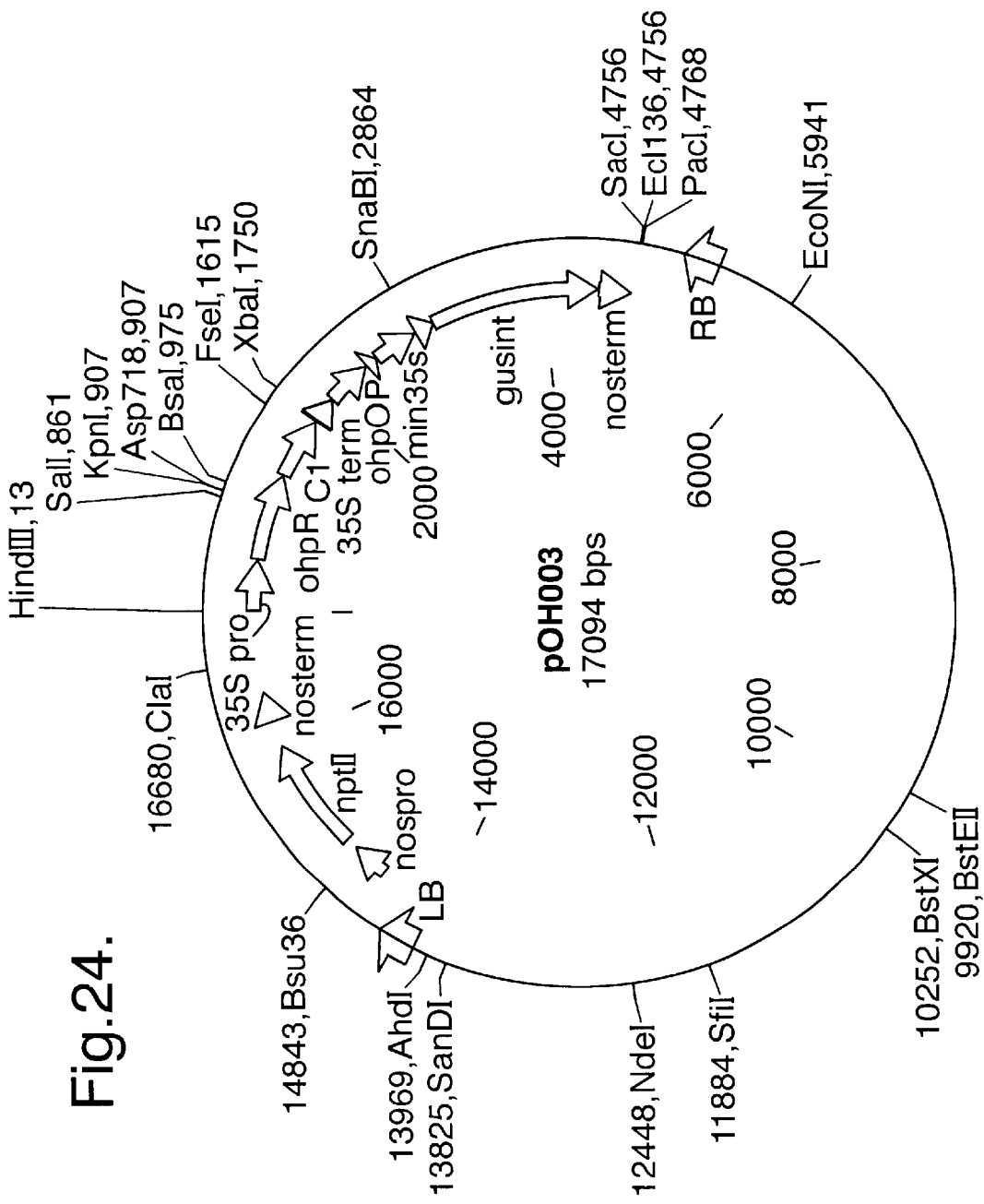
Figure 25:
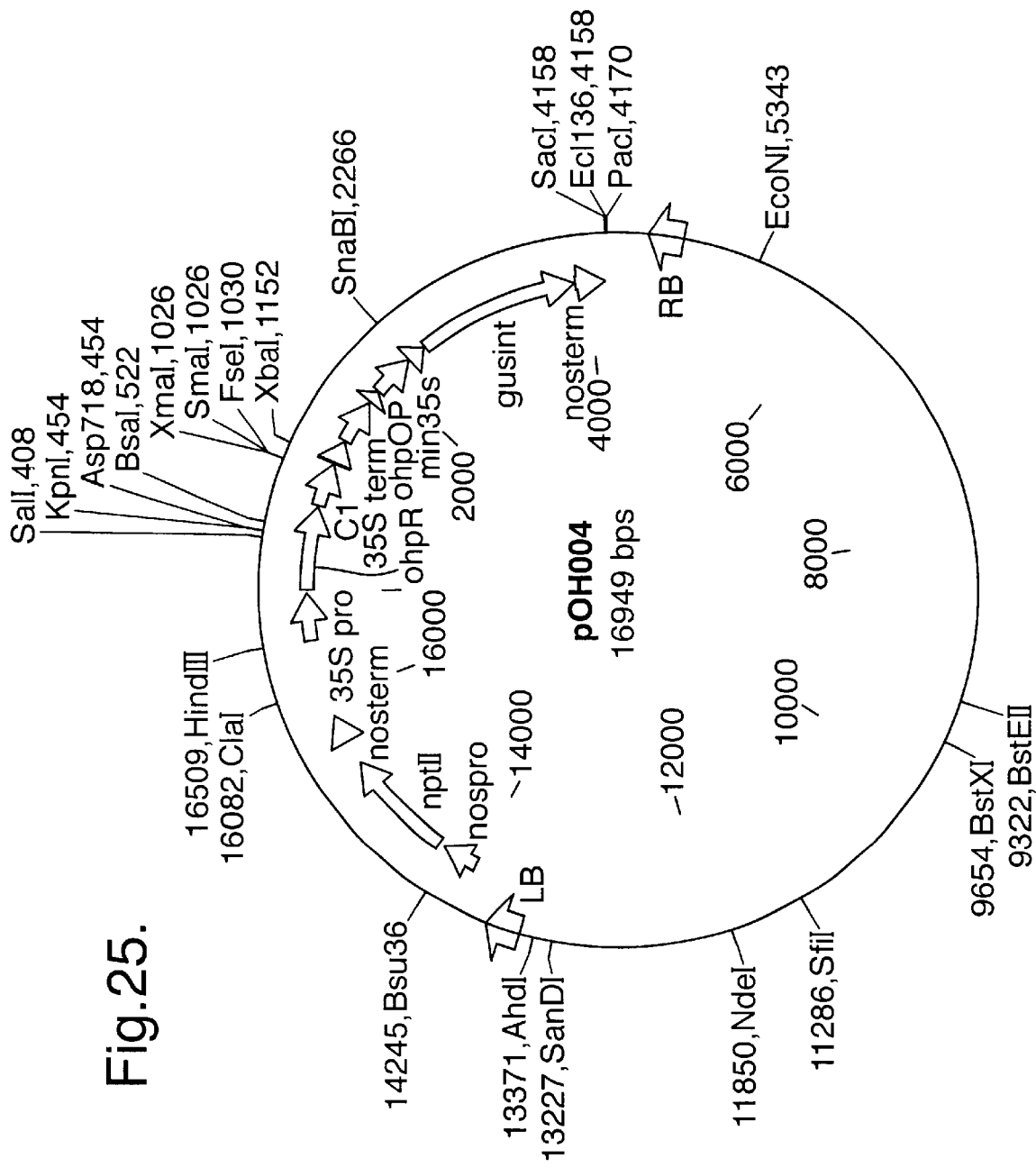
Figure 26:
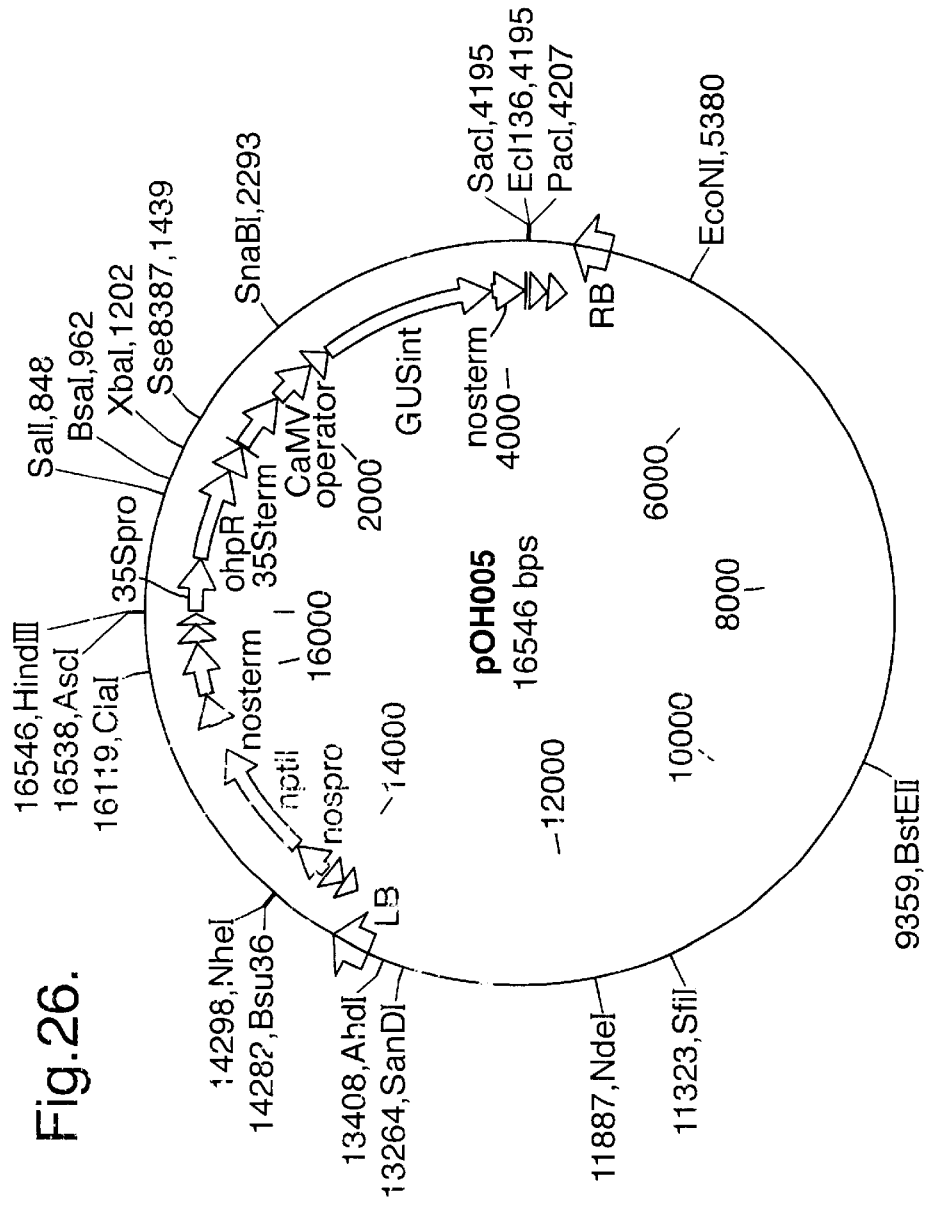
Figure 27:
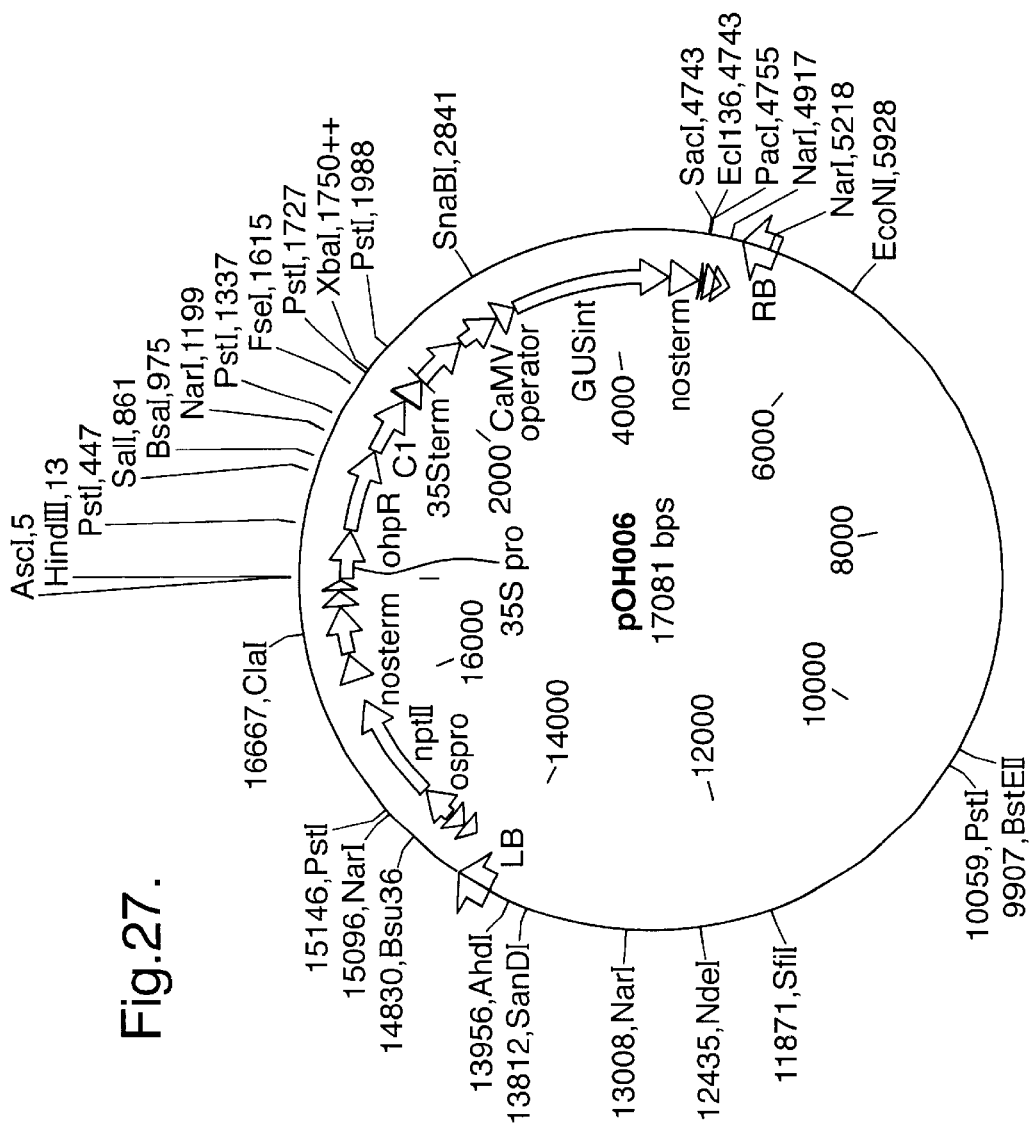
Figure 28:
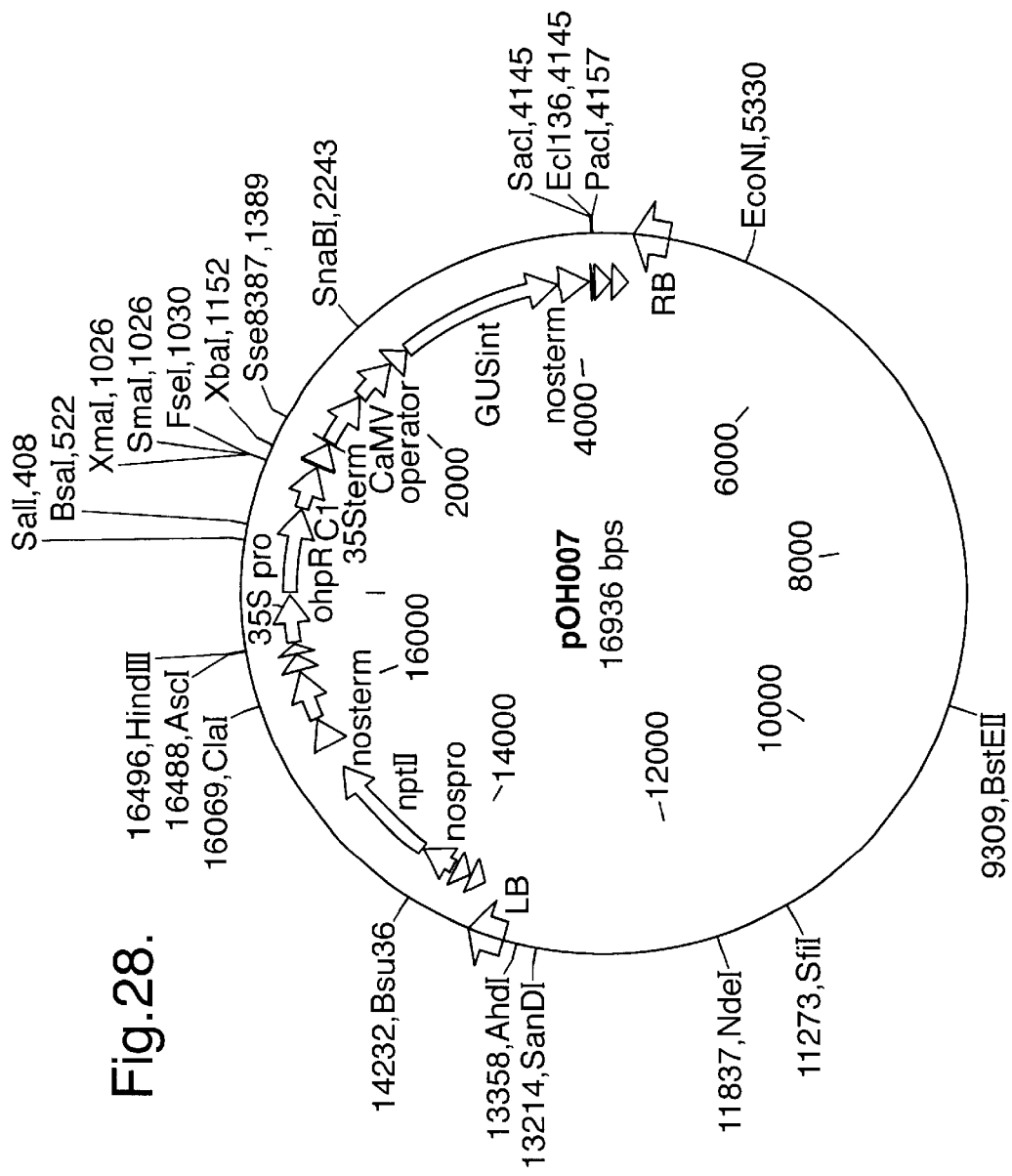
Figure 5:
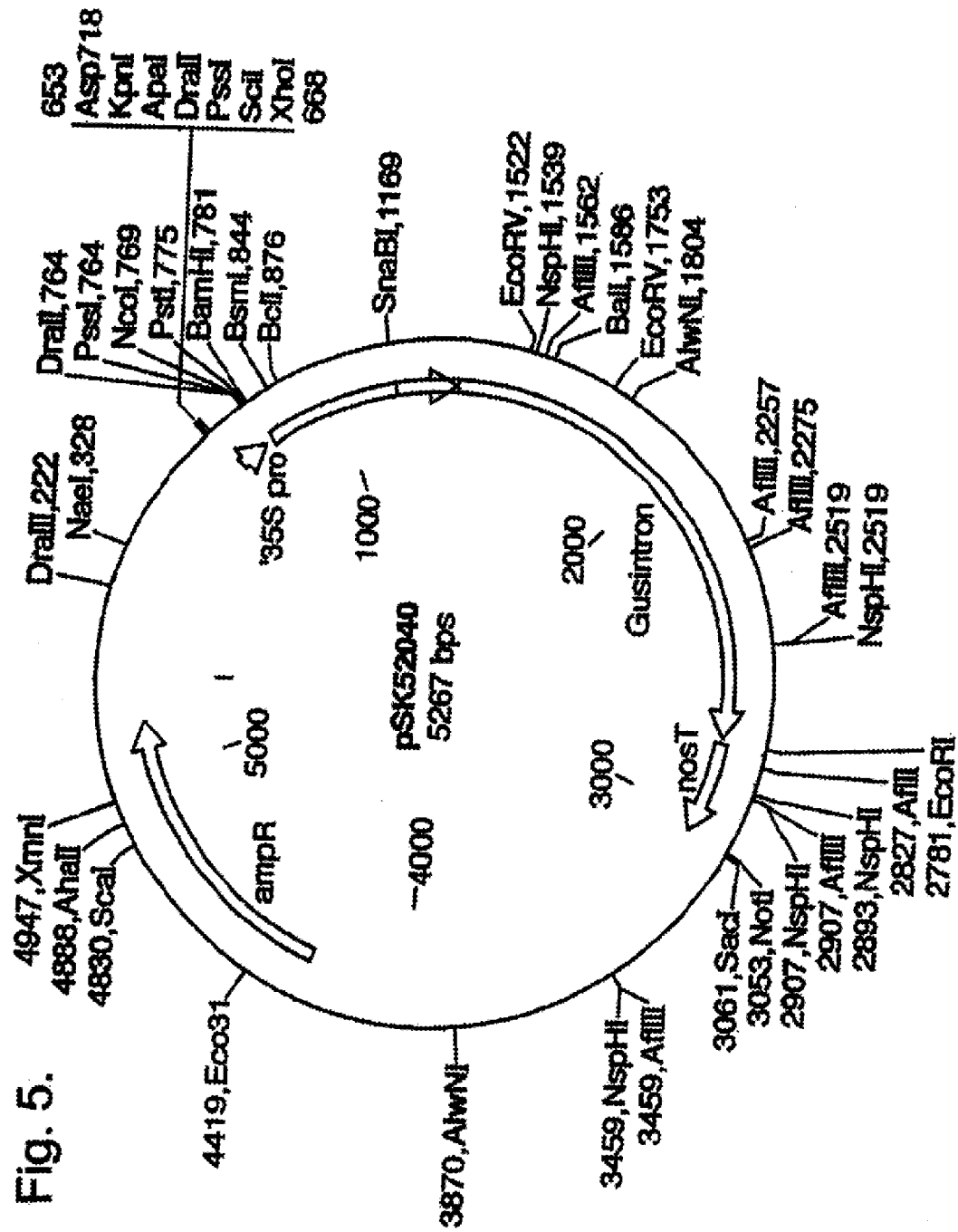
Figure 6:
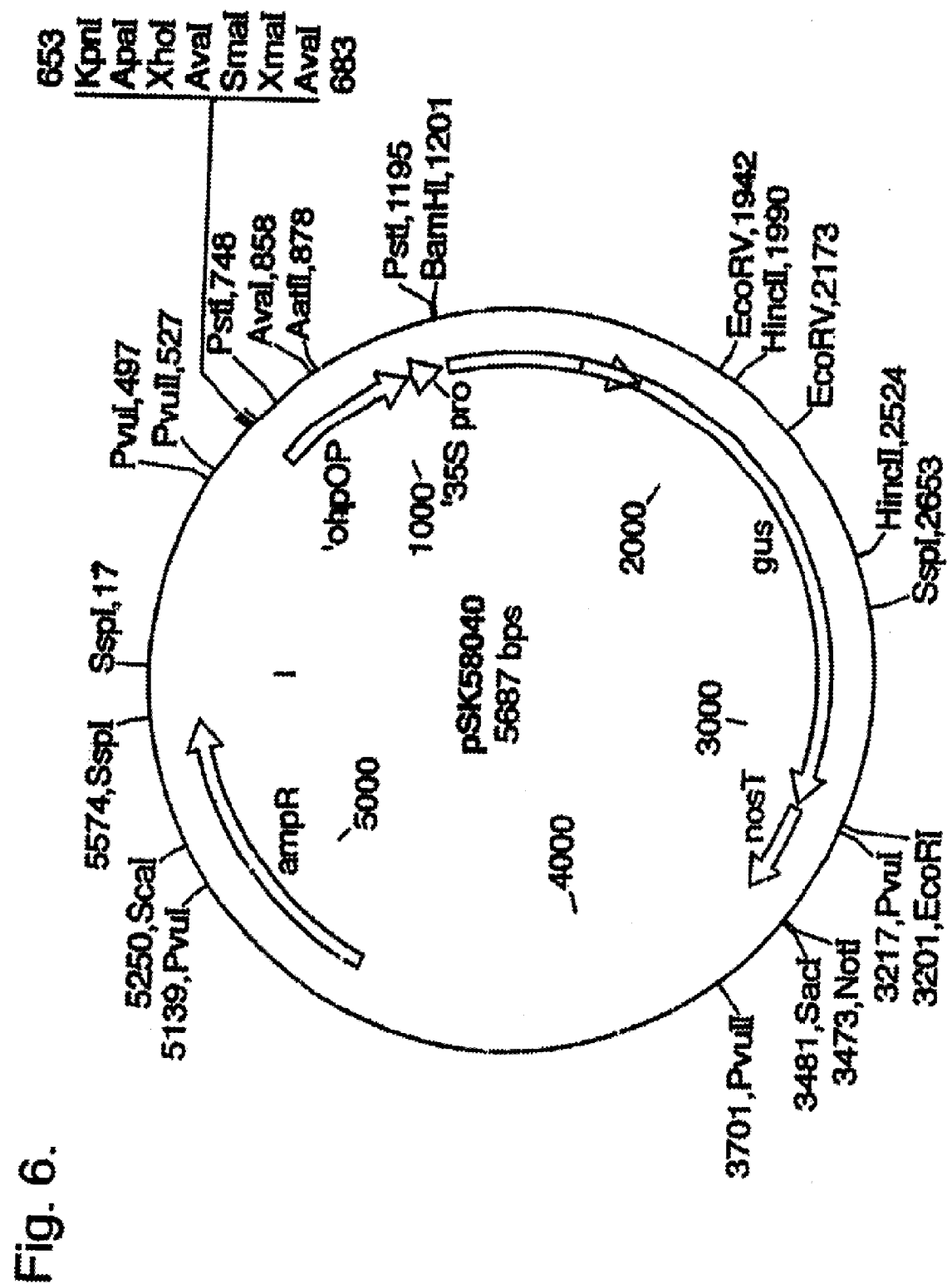
Figure 7:
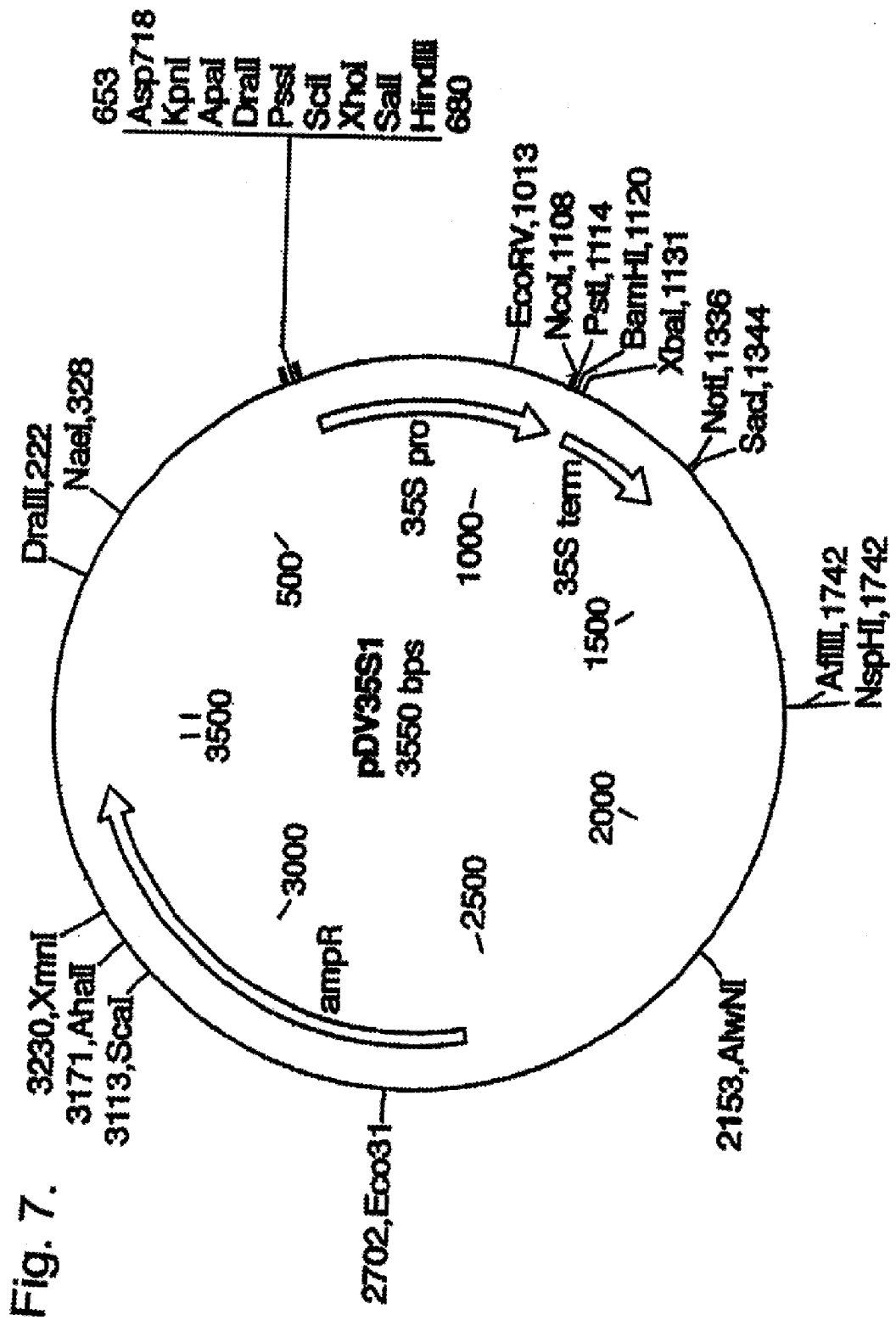

FIG. 12 shows a schematic diagram of plasmid pUCAP (van Engelen et al., 1995),

FIG. 13 shows a schematic diagram of plasmid pDV35S2 as used in the present invention. The plasmid is the pUCAP plasmid with the CaMV 35S promoter/terminator fragment from pDV35S1;

FIG. 14 shows a schematic diagram of plasmid pSK10489 as used in the present invention. The plasmid contains the ohpR sequence inserted into the BamHI and XbaI sites between the CaMV 35S promoter and the CaMV 35S terminator in pDV35S1;

FIG. 15 shows a schematic diagram of plasmid pSK10490 as used in the present invention. The plasmid contains the translational fusion between the ohpR coding sequence (nucleotide 295 to nucleotide 1035 of SEQ ID NO: 1) and part of the C1 cDNA from the NarI at nucleotide 536 to the end of the coding region at nucleotide 839, amino acids 179 to 279 of the C1 protein) from plasmid pSK490 inserted into the BamHI and XbaI sites between the CaMV 35S promoter and the CaMV 35S terminator in pDV35S1;

FIG. 16 shows a schematic diagram of plasmid pSK10491 as used in the present invention. The plasmid contains the translational fusion between the ohpR coding sequence (nucleotide 295 to nucleotide 1035 of SEQ ID NO: 1) and part of the C1 cDNA (from the PstI site at nucleotide 674 to the end of the coding region at nucleotide 539, amino acids 219 to 279 of the C1 protein) from plasmid pSK491 inserted into the BamHI and XbaI sites between the CaMV 35S promoter and the CaMV 35S terminator in pDV35S1;

FIG. 17 shows a schematic diagram of plasmid pBNP as used in the present invention. The plasmid is also known as pBINplus (van Engelen 1995);

FIG. 18 shows a schematic diagram of plasmid pBNP58040 as used in the present invention. The plasmid contains the SmaI/SacI DNA fragment from pSK58040 inserted into the SmaI/SacI sites in pBINplus. This fragment contains the ohp operator from nucleotide 1036 to nucleotide 1449 of SEQ ID NO: 1 upstream of the CaMV 35S-90 bp core promoter, GUS intron (Vancanneyt et al., 1990) and nos terminator;

FIG. 19 shows a schematic diagram of plasmid pBNP60040 as used in the present invention. The plasmid contains the XhoI/SacI fragment from pSK60040 inserted into the XhoI/SacI sites in pBINplus. This fragment contains the chimeric promoter (Seq. ID. No: 13), a GUS intron (Vancanneyt et al., 1990) and a nos terminator;

FIG. 20 shows a schematic diagram of the plasmid pBNP10489 as used in the present invention. The plasmid contains the HindIII/SacI fragment from pSK10489 inserted into the HindIII/SacI sites in pBINplus. This fragment contains the ohpR sequence inserted between the CaMV 35S promoter and the CaMV 35S terminator;

FIG. 21 shows a schematic diagram of the plasmid pBNP10490 as used in the present invention. The plasmid contains the HindIII/SacI fragment from pSK10490 inserted into the HindIII/SacI sites in pBINplus. This fragment contains the translational fusion between the ohpR coding sequence (nucleotide 295 to nucleotide 1035 of SEQ ID NO: 1) and part of the C1 cDNA (from the NarI at 536 bp to the end of the coding region at nucleotide 839, amino acids 179 to 279 of the C1 protein) inserted between the CaMV 35S promoter and the CaMV 35S terminator in pDV35S;

FIG. 22 shows a schematic diagram of the plasmid pBNP10491 as used in the present invention. The plasmid contains the HindIII/SacI fragment from pSK10491 inserted into the HindIII/SacI sites in pBINplus, This fragment contains the translational fusion between the ohpR coding sequence (nucleotide 295 to nucleotide 1035 of SEQ ID NO: 1) and part of the C1 cDNA (from the PstI site at nucleotide 674 to the end of the coding region at nucleotide 839, amino acids 219 to 279 of the C1 protein) inserted between the CaMV 35S promoter and the CaMV 35S terminator in pDV35S;

FIG. 23 shows a schematic diagram of the plasmid pOH001 as used in the present invention. The plasmid is a double construct in pBINplus containing the ohp operator from nucleotide 1036 to nucleotide 1449 of SEQ ID NO: 1 upstream of the CaMV 35S-90 bp core promoter, GUS intron and nos terminator, and also containing the ohpR sequence between the CaMV 35S promoter and the CaMV 35S terminator;

FIG. 24 shows a schematic diagram of the plasmid pOH003 as used in the present invention. The plasmid is a double construct in pBINplus containing the ohp operator from nucleotide 1036 to nucleotide 1449 of SEQ ID NO: 1 inserted upstream of the CaMV 35S-90 bp core promoter, GUS intron and nos terminator, and also containing the translational fusion between the ohpR coding sequence (nucleotide 295 to nucleotide 1035 of SEQ ID NO: 1) and part of the C1 cDNA (from the NarI at nucleotide 536 to the end of the coding region at nucleotide 839, amino acids 179 to 279 of the C1 protein) between the CaMV 35S promoter and the CaMV 35S terminator;

FIG. 25 shows a schematic diagram of the plasmid pOH004 as used in the present invention. The plasmid is a double construct in pBINplus, containing the ohp operator from nucleotide 1036 to nucleotide 1449 of SEQ ID NO: 1 upstream of the CaMV 35S-90 bp core promoter, GUS intron and nos terminator, and also containing the translational fusion between the ohpR coding sequence (nucleotide 295 to nucleotide 1035 of SEQ ID NO: 1) and part of the C1 cDNA (from the PstI site at nucleotide 674 to the end of the coding region at nucleotide 839, amino acids 219 to 279 of the C1 protein) between the CaMV 35S promoter and the CaMV 35S terminator;

FIG. 26 shows a schematic diagram of the plasmid pOH005 as used in the present invention. The plasmid is a double construct in pBINplus, containing the chimeric promoter (Seq. ID. 13), a GUS intron (Vancanneyt et al., 1990) and a nos terminator, and also containing the ohpR sequence between the CaMV 35S promoter and the nos terminator and also containing the ohpR sequence between the CaMV 35S promoter and the CaMV 35S terminator;

FIG. 27 shows a schematic diagram of the plasmid pOH006 as used in the present invention. The plasmid is a double construct in pBINplus, containing the chimaeric promoter (Seq. ID. 13), a GUS intron (Vancanneyt et al., 1990) and a nos terminator, and also containing the translational fusion between the ohpR coding sequence (nucleotide 295 to nucleotide 1035 of SEQ ID NO: 1) and part of the C1 cDNA (from the NarI at nucleotide 536 to the end of the coding region at nucleotide 839, amino acids 179 to 279 of the C1 protein) between the CaMV 35S promoter and the CaMV 35S terminator;

FIG. 28 shows a schematic diagram of the plasmid pOH007 as used in the present invention. The plasmid is a double construct in pBINplus containing the chimeric promoter (Seq. ID. 1), a GUS intron (Vancanneyt et al., 1990) and a nos terminator, and also containing the translational fusion between the ohpR coding sequence (nucleotide 295 to nucleotide 1035 of SEQ ID NO: 1) and part of the C1 cDNA (from the PstI site at nucleotide 674 to the end of the coding region at nucleotide 839, amino acids 219 to 279 of the C1 protein) between the CaMV 35S promoter and the CaMV 35S terminator.

5. DETAILED DESCRIPTION OF THE INVENTION

The present invention provides a method of controlling eukaryotic gene expression comprising introducing into or transforming a eukaryotic cell with (i) an inducible gene expression system, comprising a first nucleotide sequence comprising a first 5' regulatory region operably linked to a nucleic acid sequence which encodes a regulator polypeptide and an untranslated 3' termination sequence, and (ii) a second nucleotide sequence comprising a second 5' regulatory region operably linked to a nucleic acid sequence which is a coding or non-coding sequence (i.e., the target gene or sequence), the expression of the nucleic acid sequence of the second nucleotide sequence being controlled by the regulator polypeptide of the first nucleotide sequence using an inducer. The inducer thereby causes modulation of expression of the nucleic acid sequence of the second nucleotide sequence (the target gene). The nucleotide sequence of the regulator polypeptide and/or the second 5' regulatory region, or parts thereof, of the second nucleotide sequence are preferably isolated from a prokaryote source.

While the first nucleotide sequence of the method and chimeric gene hereof advantageously comprise an untranslated 3' termination sequence, a termination sequence may not be essential to the operation of the inducible expression system.

Advantageously the inducible gene expression system is a chemically inducible gene expression system.

Preferably, one or more of the 5' regulatory regions each comprises a promoter which allows expression in eukaryote cells and/or tissues.

Appropriate promoters are chosen so that expression of the regulator polypeptide may be constitutive, developmentally regulated, tissue-specific, cell-specific or cell compartment-specific. Suitable constitutive promoters include but are not limited to CaMV 35S and CaMV 19S promoters.

Suitable tissue specific promoters include but are not limited to the patatin promoter and the petE promoter.

Suitable cell compartment promoters include but are not limited to promoters of chloroplast genes, such as the gene encoding the large subunit of ribulose biphosphate carboxylase and promoters of mitochondrial genes, such as the 18S-5S rRNA genes. Other suitable promoters will be known to one skilled in the art.

Advantageously, the 5' regulatory regions may also comprise one or more enhancer sequences. The enhancer sequence may be a transcriptional and/or translational enhancer sequence.

Numerous sequences have been found to enhance gene expression in transgenic plants. Suitable translational enhancer sequences include a number of non-translated leader sequences derived from viruses are known to enhance expression. Specifically, leader sequences from Tobacco Mosaic Virus (TMV), Maize Chlorotic Mottle Virus (MCMV) and Alfalfa Mosaic Virus (AMV) have been shown to be effective in enhancing expression (e.g. Gallie et al., 1987, Skuzeski et al., 1990). Other leader sequences known in the art include but are not limited to: Picornavirus leaders, Potyvirus leaders, AMV RNA4 leader (Jobling & Gehrke 1987) or the HSP 70 leader (disclosed in U.S. Pat. No. 5,659,122).

Suitable transcriptional enhancer sequences will be known to those skilled in the art, such as the petE enhancer disclosed in our International Patent Application, Publication No. WO 97/20056.

Various intron sequences have been shown to enhance expression when added to the 5' regulatory region. For example, the introns of the maize Adh1 gene have been found to significantly enhance the expression of the wild-type gene under its cognate promoter when introduced into maize cells (Callis et al., 1987). International Patent Application, Publication No. WO 9319189 discloses the use of the Hsp70 intron from maize to enhance gene expression in transgenic plants.

Advantageously, the regulator polypeptide comprises one or more domains, which domains may be a ligand binding domain, a nucleic acid binding domain, a transactivation domain, a targeting domain, a silencing/repressing domain or a dimerization domain. The regulator sequence may thus comprise a chimeric gene of different sequences.

The ligand binding domain suitably comprises a sequence of amino acids whose structure binds non-covalently a complementary ligand. The ligand may be a chemical ligand. Hence, a ligand binding domain and its ligand form a complementary binding pair. Ligand binding domains for the construction of chimaeric regulator polypeptides may also be obtained from a variety of sources. The complementary ligand may be the inducer, a derivative or a precursor of the inducer.

It is possible to use two or more chemical ligands that may act together as synergists and/or antagonists. The source of chemical ligand will depend on which ligand binding domains are present in the regulator polypeptide. Any chemical compound will suffice as long as it is shown to form a complementary binding pair with the chosen ligand binding domain.

The nucleic acid binding domain comprises a sequence of amino acids which binds non-covalently to a specific nucleotide sequence known as a response element (RE). The response element may be located in the 5' regulatory region of the second nucleotide sequence. The nucleotide sequence and linear orientation determines which nucleic acid binding domain or domains will form a complementary binding pair with the response element. Considerable flexibility can be introduced into the method of controlling gene expression by using these conserved response elements in other ways.

Additional flexibility in controlling gene expression may be obtained by using nucleic acid binding domains and response elements from other nucleic acid binding proteins, which include but are not limited to the LexA, Gal4, LacI, Tet, C1 and Ace1 proteins described above.

A further degree of flexibility in controlling gene expression can be obtained by combining response elements which form complementary binding pairs with nucleic acid binding domains from different types of nucleic acid binding proteins, i.e. overlapping response elements.

The transactivation domain comprises one or more sequences of amino acids acting as subdomains which affect the operation of transcription factors during pre-initiation and assembly at the TATA box. The effect of the transactivation domain is to allow repeated transcription initiation events, leading to greater levels of gene expression. Different transactivation domains are known to have different degrees of effectiveness in their ability to increase transcription initiation. In the present invention, it is desirable to use transactivation domains which have superior transactivating effectiveness in eukaryotic cells in order to create a high level of target gene expression in eukaryotic cells. Transactivation domains which have been shown to be particularly effective include but are not limited to Vp16 (isolated from the herpes simplex virus) and C1 isolated from maize. Other transactivation domains known to those skilled in the art will also be effective.

The silencing/repressing domain comprises one or more sequences of amino acids acting as subdomains which affect the RNA polymerase II basal or regulatory transcription machinery. The effect of the silencing/repressing domain is to stop the progression of transcription. Different silencing/repressing domains are known to have different degrees of effectiveness in their ability to decrease transcription. In the present invention, it is desirable to use silencing/repressing domains which have superior silencing/repressing effectiveness in eukaryotic cells in order to create a high level of target gene repression in eukaryotic cells. Silencing/repression domains which have been shown to be particularly effective include but are not limited to the KRAB domains identified in human, mouse and Xenopus zinc finger proteins (for review see Hanna-Rose & Hansen 1996) and the Oshox1 protein of rice (Meijer et al., 1997). Other silencing/repressing domains known to those skilled in the art will also be effective.

The dimerization domain comprises one or more sequences of amino acids acting as subdomains which affect the protein—protein interaction. Different dimerization domains are known to have different degrees of effectiveness in their ability to form protein—protein interactions. In the present invention, it is desirable to use dimerization domains which have superior dimerization effectiveness in eukaryotic cells in order to create a high level of protein-protein interaction in eukaryotic cells. Dimerization domains which have been shown to be particularly effective include but are not limited to Helix-loop-helix domains of Myc and MycoD and the leucine zipper domains of Myc and GCN4 proteins. Other dimerization domains known to those skilled in the art will also be effective.

The targeting domain may comprise targeting polypeptides to direct the regulator sequence to different parts of eukaryotic cells. Suitable targeting domains include but are not limited to examples such as a plasma membrane targeting sequence (Hedley et al., 1993), golgi , endoplasmatic reticulum (Iturriaga et al., 1989), nuclear targeting signals (Varagona et al., 1992, Raikhel 1992), chloroplast (Rensink et al., 1998), mitochondrial (Boutry et al., 1987) or inner envelope targeting sequences (Knight & Gray 1995).

The nucleotide sequences which encode any of the above domains may advantageously be modified for improved expression in eukaryotes, have altered functionality, or both. Such modifications include, but are not limited to, altering codon usage, insertion of introns or creation of mutations, preferably in the ligand binding domain and/or the nucleotide binding domain. Modified nucleotide sequences of the regulatory sequence are an aspect of the present invention.

Furthermore, ligand-binding, nucleic acid binding, transactivation and targeting domains may be assembled in a chimeric regulator polypeptide in any functional arrangement.

Chimeric regulator polypeptides may also have multiple domains of the same type, for example, more than one transactivation domain or nucleic acid binding domain per regulator polypeptide. Mutant regulator polypeptides may be prepared by methods of mutagenesis known in the art, such as chemical mutagenesis or site-directed mutagenesis. This might result in ligand binding domains with altered ligand binding and/or nucleic acid binding domains with altered recognition sites.

Advantageously the regulatory sequence comprises a ligand binding domain and/or a DNA binding domain.

Preferably, the regulator sequence is the nucleotide sequence from 295–1035 bp of SEQ ID NO: 1. Advantageously the sequence may be isolated from the ohpR sequence in Rhodococcus sp. V49. Subsequences of this sequence having the necessary function may also be used in the invention.

Rhodococcus sp. V49 encodes the OHP catabolic operon, which is presented in SEQ ID NO: 1, which sequence shows the nucleotide sequences among others of the ohpR, the ohpA operator region (1036–1260 bp), ohpA, OhpB, OhpC and OhpD genes, which when expressed allow growth on OHP as sole carbon-energy source. SEQ. ID. Nos. 2 through 7 represent amino acid sequences of the proteins encoded by the OHP catabolic operon, for example, ohpR regulator (SEQ ID NO: 2), ohpA transport (SEQ ID NO: 3), OhpB monoxygenase (SEQ ID NO: 4), OhpD catechol 2,3-dioxygenase (SEQ ID NO: 5), and OhpC hydrolase (SEQ ID NO: 6). Nucleic acid sequences substantially similar to those sequences or nucleic acid sequences encoding proteins with similar functionality may also be suitable for aspects of the present invention.

Gene sequence similarity is established by Southern Blot screening. Such screening is initially carried out under low-stringency conditions, which comprise a temperature of about 37° C. or less, a formamide concentration of less than about 50%, and a moderate to low salt (e.g. Standard Saline Citrate ('SSC')=0.15 M sodium chloride; 0.15 M sodium citrate; pH7) concentration. Alternatively, a temperature of about 50° C. or less and a high salt (e.g. SSPE=0.280 M sodium chloride; 9 mM disodium hydrogen phosphate; 9 mM sodium dihydrogen phosphate; 1 mM sodium EDTA; pH 7.4). Preferably the screening is carried out at about 37° C., a formamide concentration of about 20%, and a salt concentration of about 5×SSPE. These conditions will allow the identification of sequences which have a substantial degree of similarity with the probe sequence, without requiring the perfect homology for the identification of a stable hybrid. The phrase 'substantial similarity' refers to sequences which share at least 50% overall sequence identity. Preferably, hybridization conditions will be selected which allow the identification of sequences having at least 70% sequence identity with the probe, while discriminating against sequences which have a lower level of sequence identity with respect to the probe. After low stringency hybridization has been used to identify several bacterial whose genome or DNA sub-clones exhibit a substantial degree of similarity with the probe sequence, this subset of genomes or sub-clones is then subjected to higher stringency hybridization, so as to identify those of this subset of genomes or sub-clones having a particularly high level of homology with respect to the probe sequences. Medium stringency conditions comprise a temperature of about 39° C. and a medium salt (SSC) concentration. High stringency conditions comprise a temperature of about 42° C. or less, and a low salt (SSC) concentration. Alternatively, they may comprise a temperature of 65° C. or less, and a low salt (SSPE) concentration. Preferred conditions for such screening comprise a temperature of about 42° C., a formamide concentration of about 20%, and a salt concentration of about 2×SSC, or a temperature of about 65° C., and a salt concentration of about 0.2 SSPE.

Suitable untranslated 3' termination sequences such as the CaMV 35S or nos terminator will be known to those skilled in the art.

Preferably, the 5' regulatory region of the second nucleotide sequence may also comprise a core promoter sequence and the response element (RE) or response elements necessary for complementary binding of the regulator polypeptide. By core promoter it is intended that the basal promoter elements are inactive or nearly so without activation. Such a promoter has low background activity in eukaryotes when there is no transactivator present, or when enhancer or response element binding sites are absent. Core promoters that are particularly useful for target genes in plants are the A1 core promoter which is obtained from the A1 gene of maize (Tuerck & Fromm, 1994) or the CaMV35s core promoter.

Alternatively, the 5' regulatory region of the second nucleotide sequence may also comprise a full-length promoter sequence and the response element (RE) or response elements necessary for complementary binding of the regulator polypeptide. Such a promoter has high activity in eukaryotes when there is no transactivator present. Full-length promoters that are particularly useful for target genes in plants are the CaMV 35S promoter, the CERV promoter and the petE promoter.

Preferably, the response element of the 5' regulatory region of the second nucleotide sequence is derived from the nucleotide sequence seen from nucleotide 295 to nucleotide 2805 in SEQ ID NO: 1. Advantageously the sequence is isolated from the ohpA promoter region (nucleotides 1036–1260 of SEQ ID NO: 1) in Rhodococcus sp. V49 (ATCC19070). Subsequences of this sequence having the necessary function and/or multiples of this sequence or subsequences can be used in the present invention in normal or reverse orientation, upstream or downstream of the core promoter, and in any order thereof. Substantially similar sequences to the ohpR-ohpA region in accordance with the hybridization conditions described above are also within the scope of the present invention.

Suitable coding sequences in the second nucleotide sequence include, but are not limited to, sequences which encode proteins involved in carbon metabolism; flowering; fertility and/or sterility, for example, the use of barnase or diptheria toxin A-chain; cell wall metabolism; genes that respond to environmental signals, for example pathogen attack, such as nematode, arachnid or aphid attack; or bacterium, fungus, virus, or insect resistance; or genes that confer resistance to antibiotics, herbicides or other toxic compounds.

The coding sequence may be homologous or heterologous in origin with respect to the eukaryote being transformed.

Sense, co-suppression or anti-sense technology may be used as required to achieve alteration of the eukaryote.

Nucleotide sequences may be introduced into the cell by any method known to one skilled in the art. Transformation techniques such as the use of Agrobacterium, microinjection, microprojectile-bombardment, electroporation and others known to the skilled man are among those methods for which this invention is appropriate.

The expression of the nucleic acid sequence of the second nucleotide sequence (also known herein as the target-gene) may be suitably increased or decreased, whether from a basal or median level respectively, or completely repressed or activated.

Advantageously, an increase in target gene expression levels may be caused by the addition or presence of the inducer. Alternatively, an increase in target gene expression levels may be caused by the withdrawal or absence of the inducer. Similarly, a decrease in target gene expression levels may be caused by the addition or presence of the inducer, or alternatively, a decrease in target gene expression levels may be caused by the withdrawal or absence of the inducer.

Preferably, the inducer which causes modulation of expression of the nucleic acid sequence is a chemical compound, such as OHP, 2-hydroxy cinnamic acid, toluene, bezene, n-hexadecane or a functional equivalent of either. The inducer may also, however, be a protein or nucleic acid sequence, depending on the complementary domain of the regulator sequence. The 5' regulatory region of the second nucleotide sequence may suitably comprise one or more response elements, each being necessary for complementary binding of an appropriate domain or other portion of the regulator sequence.

Advantageously the inducer acts by indirect action. Alternatively, the inducer acts by direct action.

Preferably the eukaryotic cell is a plant cell. The plant cell may be one or more from the group consisting of, for example, crops such as potato, wheat, maize, barley, tomato, rice, canola, sugarbeet or tobacco; trees such as eucalyptus species, populus or malus; or other plants, such as Arabidopsis.

Preferably the gene expression system comprises a single construct containing the first nucleotide sequence and the second nucleotide sequence. In the alternative, the gene expression system may utilise two or more separate constructs, and further each construct may be introduced into separate eukaryotes, which are then transferred into one eukaryote, biologically mated or crossed, for example, to bring the constructs together.

Alternatively, the expression system may comprise one transformation step followed by a further transformation step or steps. Each step may introduce one or more additional constructs, for example, co-transformation or re-transformation.

The present invention also provides a chimeric gene comprising a first nucleotide sequence comprising a first 5' regulatory region operably linked to a nucleic acid sequence which encodes a regulator polypeptide and an untranslated 3' termination sequence, and a second nucleotide sequence comprising a second 5' regulatory region operably linked to a nucleic acid sequence which is a coding or non-coding sequence (i.e., target gene or sequence), the expression of the nucleic acid sequence of the second nucleotide sequence being controlled by the regulator polypeptide of the first nucleotide sequence using an inducer. The inducer thereby causes modulation of expression of the nucleic acid sequence of the second nucleotide sequence (the target gene). The nucleotide sequence of the regulator polypeptide and/or the second 5' regulatory region or parts thereof of the second nucleotide sequence are isolated preferably from a prokaryote source.

Alternatively there may be provided a first chimaeric gene comprising the first nucleotide sequence and a second chimaeric gene comprising the second nucleotide sequence.

Advantageously the chimaeric gene is utilised in a plasmid, vector or other transportable medium suitable for microbiological genetic transformation.

Plant tissue, such as cells, organs, seed and other plant parts transformed using the aspects of the present invention are also aspects of the instant invention.

6. EXAMPLES

In order to transform eukaryotes the preparation of constructs and the use of transformation techniques are required in accordance with the following Examples.

6.1 Materials and Methods

Generally speaking, those skilled in the art are well able to construct vectors and design protocols for recombinant gene expression in common hosts such as *E. coli* and Agrobacterium. Suitable vectors for the construction of gene expression cassettes can be chosen or constructed, containing appropriate regulatory sequences, including promoter sequences, terminator fragments, polyadenylation sequences, enhancer sequences, marker genes and other sequences as appropriate. For further details, see, for example, Molecular Cloning: A Laboratory manual: 2nd edition, Sambrook et al. 1989, Cold Spring Harbor Laboratory Press. Many known techniques and protocols for manipulation of nucleic acid, for example in preparation of nucleic acid constructs, mutagenesis, sequencing and, introduction of DNA into cells, gene expression, and analysis of proteins are described in detail in Current Protocols in Molecular Biology, Second Edition, Ausubel et al., eds, John Wiley and Sons 1992. The disclosures of Sambrook et al., and Ausubel et al., are incorporated herein by reference.

However the present inventors have recognized that certain methods previously employed in the art which were developed for enteric bacteria such as *E. coli* may not be most appropriate for use in plant genetic constructs. Accordingly, advantageous methods have been developed by the inventors which in preferred forms allow the rapid construction of OHP genetic constructs and operably linked inducible 5' regulatory regions and regulator constructs.

The following examples further describe the materials and methods used in carrying out the invention and the subsequent results. They are offered by way of illustration, and their recitation should not be considered as a limitation of the claimed invention.

6.2 Isolation of the ohpR Sequence

Example 1

The coding sequence of the OHP operon OhpR (from nucleotide 295 to nucleotide 1035) was amplified by PCR from construct pJP58 using the primers OHPR3 (SEQ ID NO: 8) and OHPR4 (SEQ ID NO: 9). The construct pJP58 was deposited by Advanced Technologies (Cambridge) Ltd of 210 Cambridge Science Park, Cambridge CB4 0WA, England under the Budapest Treaty on the International Recognition of the Deposit of Micro-organisms for the purposes of Patent Procedure at the National Collection of Industrial and Marine Bacteria (NCIMB), 23 St. Machar Street, Aberdeen, Scotland on Dec. 21st 1998 under accession number NCIMB 40997. It contains a 2 kb BamHI fragment encoding the ohpA-ohpR region (nucleotides 1–1869 of SEQ ID NO: 1) cloned into pUC19 using the unique BamHI site (Veira J. & Messing, J. 1982).

Figure 1:
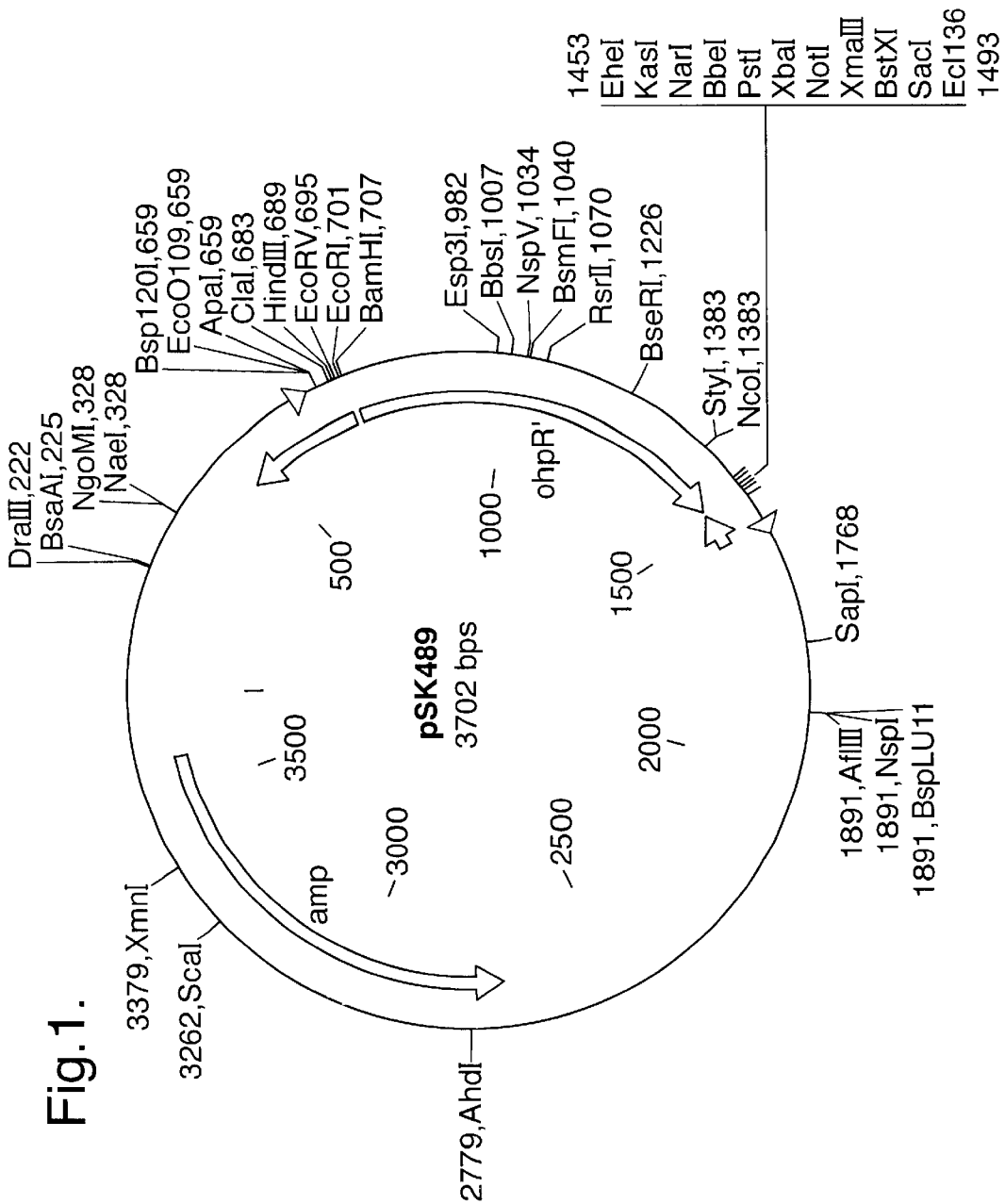
FIG. 1 shows a schematic diagram of the plasmid pSK-489 as used in the present invention. The plasmid contains the nucleotide sequence for ohpR (from nucleotide 295 to nucleotide 1035 of SEQ ID NO: 1) inserted between the EcoRI and NotI sites in pBluescript.

The PCR product was restriction digested with EcoRI and NotI and cloned into pBluescript (Stratagene) also digested with EcoRI and NotI. The resulting plasmid was named pSK489 (FIG. 1) and sequenced.

6.3 Isolation of the Transcriptional Activator Sequence C1

Example 2

Figure 2:
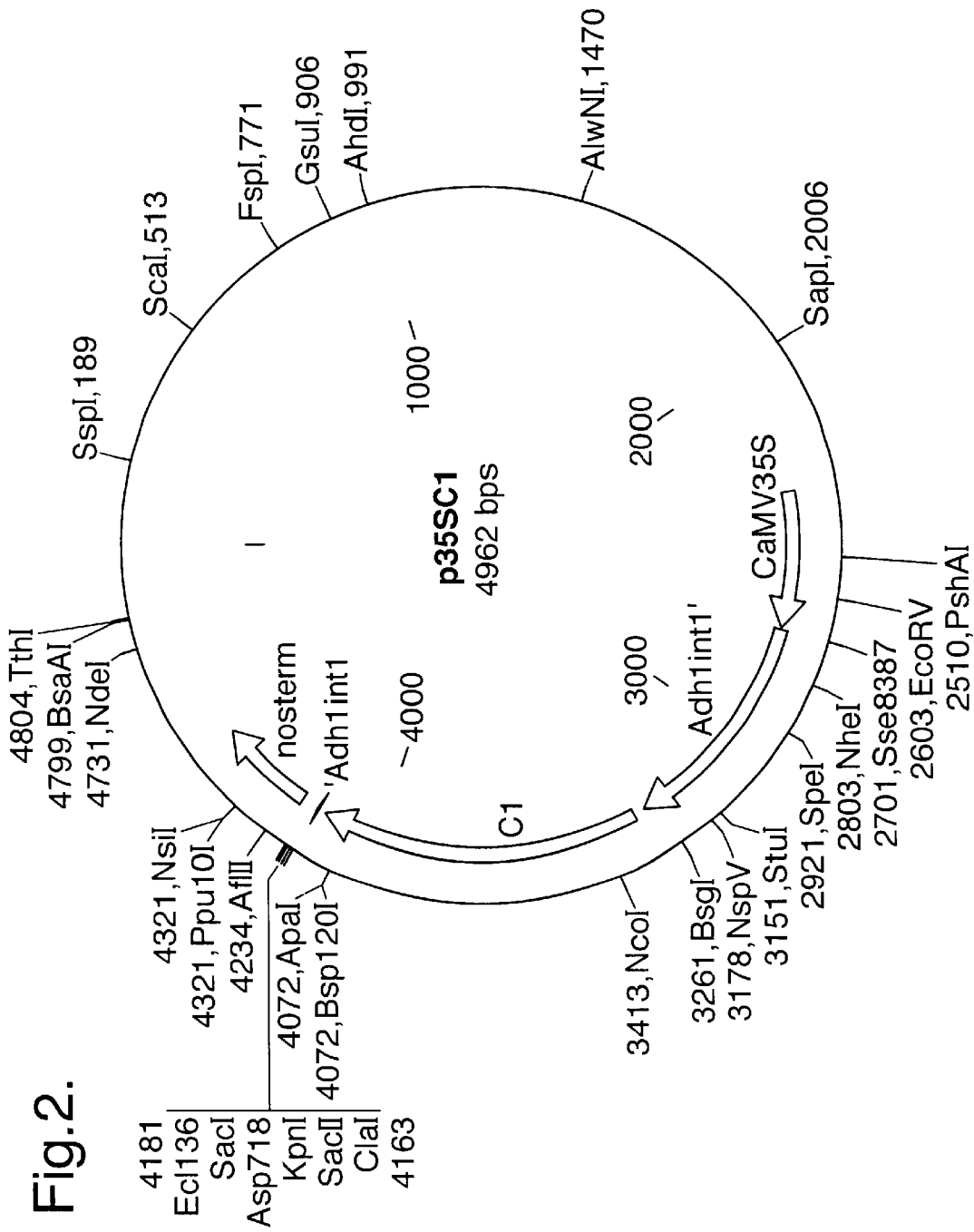
FIG. 2 shows a schematic diagram of the plasmid p35SC1 (Tuerck & Fromm 1994) as used in the present invention. The plasmid contains the C1 cDNA as described in Paz-Ares et al., (1987) inserted as an EcoRI fragment between a CaMV 35S promoter, Adh1 intron 1 and a CaMV 35S terminator.
Figure 3:
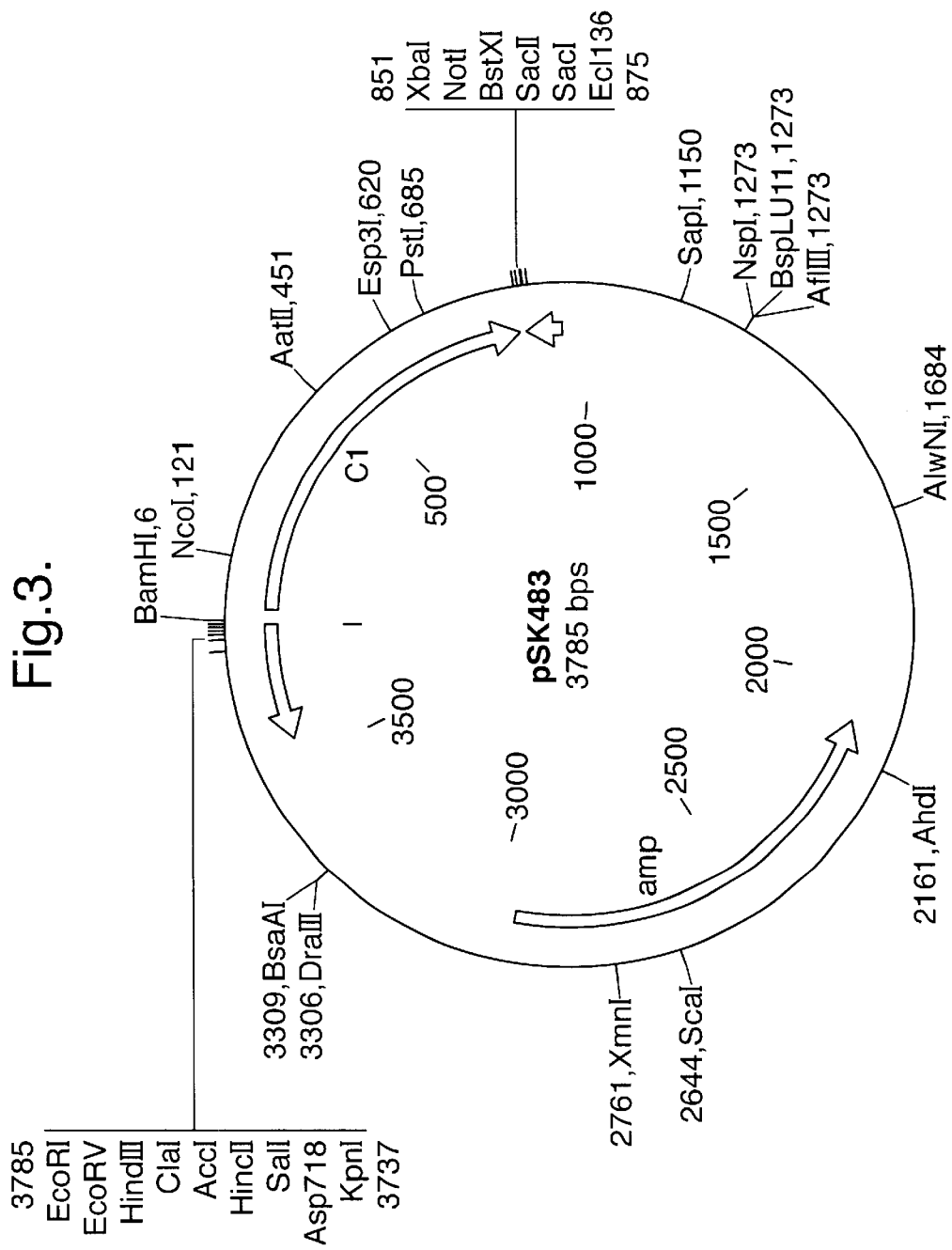
FIG. 3 shows a schematic diagram of the plasmid pSK-483 as used in the present invention. The plasmid contains the C1 coding region as described in Paz-Ares et al., (1987) inserted between the EcoRI and the NotI sites in pBluescript.

The C1 cDNA region was amplified by PCR from plasmid p35SC1 (FIG. 2), as described in Tuerck & Fromm (1994), using the primers C11 (SEQ ID NO: 10) and C12 (SEQ ID NO: 11). The PCR product was digested with EcoRI and NotI and ligated into pBluescript digested with EcoRI and NotI. The resulting plasmid was named pSK483 (FIG. 3) and sequenced.

6.4 Isolation of the Operator Sequence

Example 3

Figure 4:
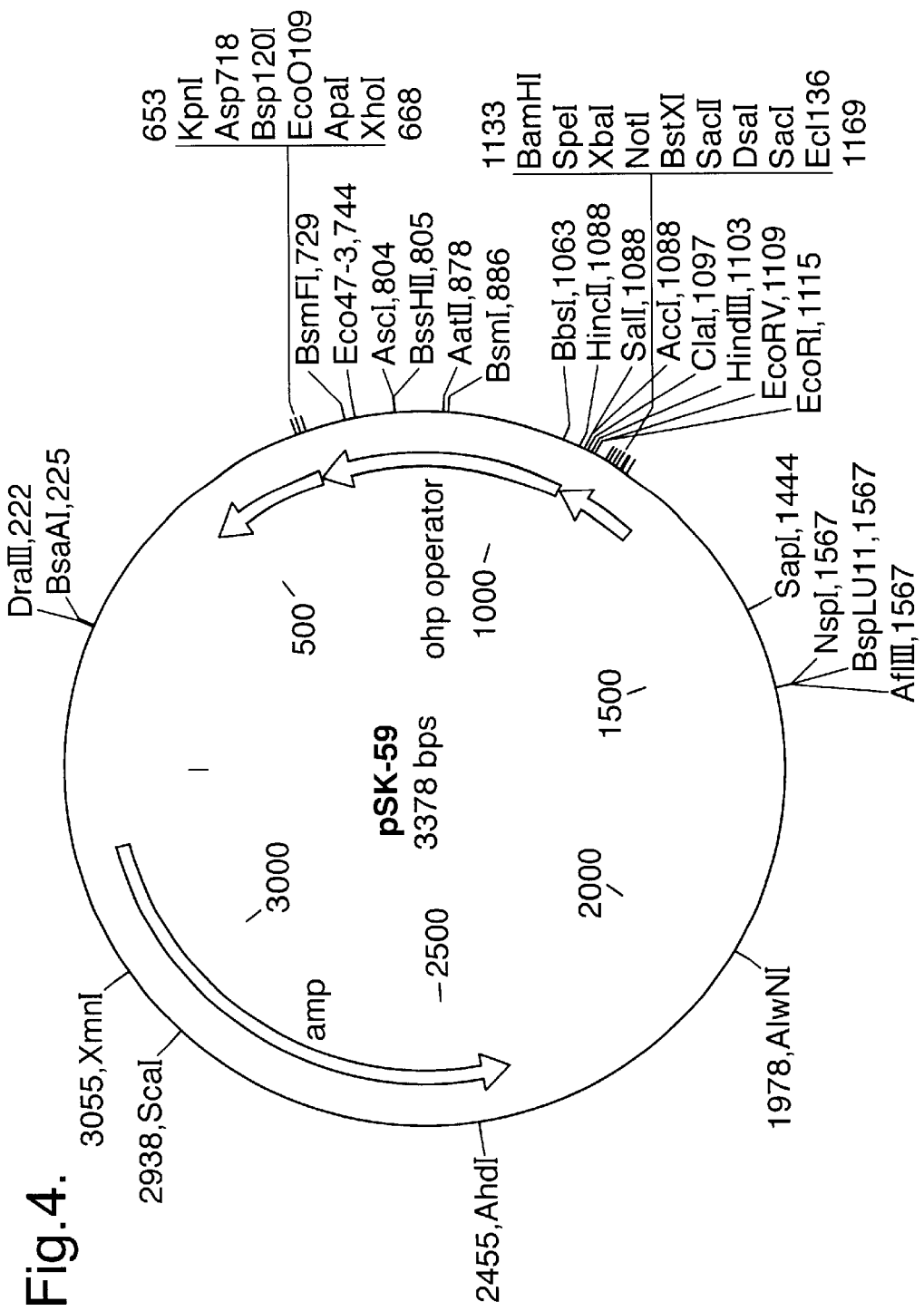
FIG. 4 shows a schematic diagram of the plasmid pSK-59 as used in the present invention. The plasmid contains part of the ohp operator (nucleotide 1036 to nucleotide 1449 of SEQ ID NO: 1) inserted between the XhoI and SalI sites in pBluescript.

Part of the operator region of the OHP operon (from nucleotide 1036 to nucleotide 1449 in SEQ ID NO: 1) was amplified by PCR from construct pJP58 using the oligonucleotide primers op1 (SEQ ID NO: 12) and op2 (SEQ ID NO: 13). The 441 bp PCR product was restriction digested to with XhoI and SalI, gel-purified and ligated into pBluescript digested with XhoI and SalI. The resulting plasmid was named pSK-59 (FIG. 4) and sequenced.

6.5 Construction of the Construct for the Nucleic Acid Sequence in the Second Nucleotide Sequence Example 4

The plasmid pSK-59 (FIG. 4) was digested with Xho1 and Sal1, the 414 bp operator region was gel-purified and ligated with pBS52040 (FIG. 5) which had been digested with XhoI and phosphatased. The resulting plasmid was named pSK58040 (FIG. 6).

6.6 Construction of a Chimeric CaMV35S Promoter-ohp Regulator Construct

Example 5

The three oligonucleotides CaMVop2 (SEQ ID NO: 14), CaMVop3 (SEQ ID NO: 15) and CaMVop4 (SEQ ID NO:16) were annealed in equimolar amounts (500 pmole each primer) and diluted tenfold. 5 µl of this dilution were used as a template for a PCR reaction (50 µl total) catalysed by a proof-reading Taq polymerase to generate double stranded product. The PCR product was resolved on an 8% polyacrylamide gel. The 125 bp PCR product was excised and purified using techniques described in Sambrook et al (1989). 1 µl of the total eluted double stranded DNA solution (50 µl) was used as a template in a PCR reaction (50 µl total) primed by oligonucleotide primers CaMVopF1 (SEQ ID NO: 17) and CaMVopR1 (SEQ ID NO: 18) and catalysed by a proof-reading Taq polymerase. The PCR product from this reaction was digested to completion with EcoRV and BamHI and the 133 bp restriction fragment ligated with plasmid pDV35S1 (FIG. 7) similarly digested to completion with EcoRV and the resulting construct was named pDV60 (FIG. 8). The inserted region was sequenced. Plasmid pDV60 (FIG. 8) was digested with XhoI and BamHI. The 476 bp synthetic promoter restriction fragment (SEQ ID NO: 19) was gel purified as described above and ligated into pSK52040 (FIG. 5) similarly digested with XhoI and BamHI. This plasmid was named pSK60040 (FIG. 9). The chimeric promoter in SEQ ID NO: 18 contains a 36 bp region of the ohp operon (from nucleotide 1225 to nucleotide 1260) inserted into the CaMV 35S promoter at nucleotide 21.

6.7 Construction of Chimeric Regulator Sequences

Example 6

The plasmid pSK483 (FIG. 3) was digested to completion with PstI and XbaI. The 162 bp fragment (the C1 cDNA region from amino acids 219 to 273 of the C1 protein) was gel-purified and ligated with pSK489 (FIG. 1) similarly digested with PstI and XbaI. The resulting plasmid was named pSK491 (FIG. 11). This ligation results in a translation fusion of the OHPR nucleotide sequence and the C1 nucleotide sequence for the transcriptional activation domain from amino acid 219 to 273.

The plasmid pSK483 (FIG. 3) was also digested to completion with NarI and XbaI. The 303 bp fragment of the C1 cDNA region (encoding amino acids 173 to 273 of the C1 protein) was gel-purified and ligated with pSK489 (FIG.

1) similarly digested with NarI and XbaI. The resulting plasmid was named pSK490 (FIG. 10). This ligation results in a translation fusion of the ohpR nucleotide sequence and the C1 nucleotide sequence for the transcriptional activation domain from amino acid 173 to 273.

6.8 Construction of pDV35S2

Example 7 pDV35S1 (FIG. 7) was digested with HindIII and SacI and the 668 bp fragment containing the CaMV 35S promoter/terminator was gel-purified and ligated with pUCAP (FIG. 12) which was digested with HindIII and SacI. The resulting construct was named pDV35S2 (FIG. 13).

6.9 Construction of a Regulator Expression Construct

Example 8

Plasmids pSK489 (FIG. 1), pSK490 (FIG. 10) and pSK491 (FIG. 11) were digested with BamHI and XbaI, the fragments encoding the regulator sequences were gel-purified and ligated with pDV35S1 (FIG. 7), similarly digested with BamHI and XbaI. The resulting plasmids were named pSK10489 (ohpR, FIG. 14), pSK10490 (ohpR-C1 NarI/XbaI fusion, FIG. 15) and pSK10491 (ohpR-C1 PstI/XbaI fusion, FIG. 16) respectively.

6.10 Construction of pBNP58040

Example 9

Plasmid pSK58040 (FIG. 6) was digested to completion with HindIII and SmaI and the 2837 bp fragment containing the CaMV 35S promoter-GUS-nos terminator was gel-purified and ligated into pBINplus (FIG. 17) similarly digested with HindIII and SmaI. The resulting plasmid was named pBNP58040 (FIG. 18).

6.11 Construction of pBNP60040

Example 10

Plasmid pSK60040 (FIG. 9) was digested to completion with HindIII and SacI and the promoter-Gus fragment was gel-purified and ligated with pBINplus (FIG. 17) similarly digested with HindIII and SacI. The resulting plasmid was named pBNP60040 (FIG. 19).

6.12 Construction of Plant Transformation Vectors Carrying the Regulator Genes Example 11

The regulator cassettes were cut out of pSK10489 (FIG. 14), pSK10490 (FIG. 15), and pSK10491 (FIG. 16), respectively. DNA was digested with HindIII and SacI. The restriction fragments containing the CaMV 35S promoter-regulator were gel-purified. The isolated fragments were ligated with pBINplus (FIG. 17) similarly digested with HindIII and SacI. The resulting plasmids were named pBNP10489 (FIG. 20—pBNP containing 10489, ohpR), pBNP10490 (FIG. 21—pBNP containing 10490, ohpR-C1 NarI fusion) and pBNP10491 (FIG. 22—pBNP containing 10491, ohpR-C1 PstI fusion).

6.13 Construction of Double Gene Expression Constructs

Example 12

The CaMV 35S promoter-regulator fragments were cut out of pSK10489 (FIG. 14), pSK10490 (FIG. 15) and pSK10491 (FIG. 16) respectively. DNA was digested with NotI, blunt-ended with Klenow DNA polymerase and then digested with HindIII. The restriction fragments containing the CaMV 35S promoter/regulator were gel-purified. pBNP58040 (FIG. 18) and pBNP60040 (FIG. 19) were digested with HindIII and SmaI. The gel-purified fragments were ligated with either the digested pBNP58040 (FIG. 18) or the digested pBNP60040 (FIG. 19). The resulting plasmids were named pOH001 (FIG. 23—pBNP containing 58040 and 10489), pOH003 (FIG. 24—pBNP containing 58040 and 10490), pOH004 (FIG. 25—pBNP containing 58040 and 10491), pOH005 (FIG. 26—pBNP containing 60040 and 10489), pOH006 (FIG. 27—pBNP containing 60040 and 10490) and pOH007 (FIG. 28—pBNP containing 60040 and 10491).

6.14 Transformation of Agrobacterium

Example 13

The plant transformation vectors (as described in Examples 9–12, Figures, 18–28) were electroporated into *Agrobacterium tumefaciens* cells. Agrobacterium cultures were selected on kanamycin-containing medium (50 $\mu$g/ml). The cultures were grown in liquid medium and then used for the transformation of plant species.

6.15 Transformation or Retransformation of Plants

Example 14

Tobacco and potato plants can be transformed using the method of leaf disk cocultivation as essentially described by Horsch et al., (1985). The binary vectors as described above in Examples 9–12 (FIGS. 18–28) are transferred to *Agrobacterium tumefaciens* LBA4404 using the method of electroporation, and cultures of said Agrobacteria can be used in transformation so that regenerated plants carry the chimeric genes as described in Examples 9–12.

Young leaves were dissected under sterile conditions, from approximately 4 week old Eucalyptus species cultures grown in Magenta boxes (7 cm×7 cm×13 cm) on LS media at 25 C., in a growth room in our tissue culture laboratory and used for Agrobacterium-mediated transformation (Horsch et al. 1985) using the strain EHA105. Inoculated tissue was left to co-cultivate for 4 days on LS media (plus 20-g/l glucose, 0.7% agarose, 0.1 mM Zeatin and 1 $\mu$M NAA) in diffuse light in a growth, conditions as before. Transformants were selected on 50 mg/ml kanamycin and 250 mg/ml claforan.

*Arabidopsis thaliana* was transformed following the protocols from Bechthold et al., (1993) and Clough (1998). Plants were grown in a growth cabinet at 22° C. under 18 h daylight before and after vacuum-infiltration.

Several direct gene transfer procedures have been developed to transform plants and plant tissues without the use of an Agrobacterium intermediate. In the direct transformation of protoplasts the uptake of exogenous genetic material into a protoplast may be enhanced by use of a chemical agent or electric field. The exogenous material may then be integrated into the nuclear genome (Pazkowski et al., 1984, Potrykus et al., 1985). Alternatively, exogenous DNA can be introduced into cells or protoplasts by microinjection. A solution of plasmid DNA is injected directly into the cell with a finely pulled glass needle (Reich et al., 1986). A more recently developed procedure for direct gene transfer involves bombardment of cells by microprojectiles carrying DNA (Klein et al., 1987). In this procedure tungsten or gold particles coated with the exogenous DNA are accelerated towards the target cells, resulting in transient expression and also in stable integration of the DNA into the plant genome.

Following transformation, the transformed cell or plant tissue is selected or screened by conventional techniques. The transformed cell or plant tissue contains the chimeric DNA sequences discussed above and is the regenerated, if desired, by known procedures. The regenerated plants are screened for transformation by standard methods. Progeny of the regenerated plants is continuously screened and selected for the continued presence of the integrated DNA sequence in order to develop improved plant and seed lines. The DNA sequence can be moved into other genetic lines by a variety of techniques, including classical breeding, protoplast fusion, nuclear transfer and chromosome transfer.

The chimeric binary vector plasmids mentioned above can be used to transform a plant already carrying other chimeric genes by the methods described above.

6.16 Transient Expression

Example 15

Transient expression assays of the gene expression cassette was essentially performed as described by Kapila et al., (1997), Rossi et al., (1993), Twell et al., (1989), Goff et al., (1990), Roth et al., (1991) and Tuerck et al., (1994).

Leaf discs of 4–6 weeks old plants were excised and incubated with the Agrobacterium suspension. The discs were incubated for 1–5 days on wet Whatman paper before they were stained for GUS expression before and after induction.

6.17 Induction of Reporter Gene Activity in Transgenic Plants

Example 16

OHP was applied to the plants (or plant cells) as a paint, spray or in the medium in concentrations ranging from 0.01 mM to 100 mM in water or in 10 mM MES, pH5.6. Tissue was harvested prior to inducer application and at appropriate times after the application. The sample tissue was ground in extraction buffer and assayed for GUS reporter gene activity as described by Jefferson (1987). Tissue was also stained for GUS expression as described by Jefferson (1987).

The present invention is not to be limited in scope by the specific embodiments described which are intended as single illustrations of individual aspects of the invention, and functionally equivalent methods and components are within the scope of the invention. Indeed, various modifications of the invention, in addition to those shown and described herein will become apparent to those skilled in the art from the foregoing description and accompanying drawings. Such modifications are intended to fall within the scope of the appended claims.

References

The following references are incorporated into the specification by references in their entireties.

Aoyama, T. & Chua, N.-H. (1997) Plant J. 11: 605–612.
Boutry, M., Nagy, F., Poulsen, C., Aoyagi, K. & Chua, N.-H. (1987) Nature 328:340–342.
Bechthold, N., Ellis, J., Pelletier, G. (1993). Comptes Rendus de l'Academie des Science Serie III Science de la Vie: 316: 1194–1199
Caddick, M. X., Greenland, A. J., Jepson, I., Krause, K.-P., Qu, N., Riddell, K. V., Salter, M. G., Schuch, W., Sonnewald, U. & Tomsett, A. B. (1998) Nature Biotechnol 16: 177–180.
Clough, S. J. & Bent, A. F. (1998). Plant J. 16(6):735–743.
Felenbok, B. (1991) J. Biotechnol. 17: 11–18.
Fillinger, S. & Felenbok, B. (1996) Mol. Microbiol. 20: 475–488.
Frohberg, C., Heins, L. & Gatz, C. (1991) PNAS 88:10470–10474.
Gallie et al. (1987) NAR 15: 8693–8711.
Gatz, C. & Quail, P. H. (1988). PNAS 85 1394–1397.
Gatz, C., Kaiser, A. & Wendenburg, R. (1991) Mol. Gen. Genet. 227: 229–237.
Gatz, C., Frohberg, C. & Wendenburg, R. (1992) Plant J. 2 : 397–404.
Goff, S. A., Klein, T. M., Roth, B. A., Fromm, M. E., Cone, K. C., Radicella, J. P. & Chandler, V. L. et al. (1990). EMBO J 9:2517–2522.
Gossen, M., Freundlieb, S., Bender, G., Mueller, G., Hillen, W. & Bujard, H. (1995) Science 268: 1766–1769.
Hanna-Rose, W., & Hnasen, U. (1996). TIG 12(6):229–234.
Haydon, D. J. & Guest, J. R. (1991). FEMS Microbiol. Letters 79:291–296.
Hedley, P. E., Machray, G. C. Davies, H. V., Burch, L. & Waugh, R. (1993) Plant Mol. Biol. 22:917–922.
Horsch, R. B., Fry, J. E., Hoffmann, N., Eichholtz, D., Rogers, S. G. & Fraley, R. T. (1985). Science 227:1229–1231.
Iturriaga, G., Jefferson, R. A. & Bevan, M. W. (1989) Plant C. 1:381–390.
Jefferson, R. A. (1987) Plant Mol. Biol. Rep. 5:387–405.
Jobling, S. A. & Gehrke, L. (1987). Nature 325:622–625.
Kapila, J., De Rycke, R., Van Montagu, M & Angenon, G. (1997). Plant Science 122:101–108.
Klein, T. M., Wolf, E. D., Wu, R. & Sanford, J. C. (1987). Nature 327:70–73.
Knight, J. S. & Gray, J. C. (1995) Plant C. 7:1421–1432.
Kulmburg, P., Judewicz, N., Mathieu, M., Lenouvel, F., Sequeval, D. & Felenbrok, B. (1992) J. Biol. Chem. 267: 21146–21153.
Lloyd, A. M., Schena, M., Walbot, V. & Davies, R. W. (1994) Science 266: 43–439.
Lüscher, B. & Eisenman, R. N. (1990). Genes & Dev. 4:2025–2035.
McKenzie, M. J., Mett, V. Reynolds, P. H. S. & Jameson, P. E. (1998) Plant Physiol. 116:969–977.
Meijer, A. H., Scarpella, E., vam Dijk, E. L., Qin, L., Taal, A. J. C., Rueb, S., McCouch, S. R., Schilperoort, R. A. & Hoge, J. H. C. (1997). Plant J. 11(2):263–276.
Mett, V. L., Lochhead, L. P. & Reynolds P. H. S. (1993) PNAS 90: 4567–4571.
Paz-Ares, X., Ghosal, D., Wienaud, U., Peterson, P. A. & Saedler, H. (1987). EMBO J. 6(12):3553–3558.
Pazkowski, J., Shilito, R. D., Saul, M. W., Mandak, V., Hohn. T, Hohn, B. & Potrykus, I. (1984). EMBO J. 3:2717–2722.
Picard, D., Salser, S. J. & Yamamoto, K. R. (1988). Cell 54: 1073–1080.
Potrykus, I., Saul, M. W., Petruska, J., Pazkowski, J., & Shilito, R. D. (1985). Mol. Gen. Gen. 199:178–182.
Raikhel, N. V. (1992) Plant Physiol. 100: 1627–1632.
Reich, T. J. et al. (1986) Bio/Technology 4: 1001.
Rensink, W. A., Pilon, M. & Weisbeek, P. (1998) Plant Physiol. 118:691–699.
Roeder, F. T., Schmulling, T. & Gatz, C. (1994). Mol. Gen. Gen. 243:32–38.
Rossi, L., Escudero, J., Hohn, B. & Tinland, B. (1993). Plant Mol. Biol. Rep. 11: 220–229.

Roth, B. A., Goff, S. A., Klein, T. M. & Fromm, M. E. (1991). The Plant Cell 3:317–325.
Salter, M. G., Paine, J. A., Riddell, K. V., Jepson, I., Greenland, A. J., Caddick, M. X. & Tomsett, A. B. (1998) Plant J. 16: 127–132.
Sambrook, J., Fritsch, E. F., Maniatis, T. Molecular Cloning, A laboratory Manual, Second Edition. Cold Spring Harbour Laboratory Press 1989
Schena, M., Lloyd, A. M. & Dacis, R. W. (1991) PNAS 88 10421–10425.
Skuzeski, J. M., Nichols, L. M. & Gestelande, R. F. (1990). Plant Mol. Biol. 15(1):65–79.
Sommer, S., Siebert, M., Bechthold, A. & Heide, L. (1998) Plant Cell Rep. 17: 891–896.
Tuerck & Fromm (1994). Plant Cell 6:1655–1663.
Twell, D., Klein, T. M., Fromm, M. E. & McCormick (1989) Plant Physiol. 91: 1270–1274.
van Engelen, F. A., Molthoff, J. W., Conner, A. J., Nap, J.-P., Pereira, A. & Steikema, W. J. (1995) Transgen. Res 4:288–290.
Varagona, M. J., Schmidt, R. J. & Raikhel, N. V. (1992) Plant C. 4:1213–1227.
Vancanneyt, G., Schmidt, R., O'Connor-Sanchez, Willmitzer, L & Rocha-Sosa (1990). Mo. Gen. Genet. 220:245–250.
Veira J. & Messing J. (1982) Gene 19: 259–268
Weinmann, P., Gossen, M., Hillen, W., Bujard, H. & Gatz, C. (1994) Plant J. 5(4): 559–569.
Wilde, R. J., Shufflebottom, D., Cooke, S., Jasinska, I., Merryweather, A., Beri, R., Brammar, W. J., Bevan, M. & Schuch, W. (1992) EMBO J. 11(4): 1251–1259.

SEQUENCE LISTING

```
<160> NUMBER OF SEQ ID NOS: 19

<210> SEQ ID NO 1
<211> LENGTH: 7600
<212> TYPE: DNA
<213> ORGANISM: Rhodococcus sp.
<220> FEATURE:
<221> NAME/KEY: CDS
<222> LOCATION: (295)..(1035)
<223> OTHER INFORMATION: ohpR regulator
<221> NAME/KEY: CDS
<222> LOCATION: (1261)..(2805)
<223> OTHER INFORMATION: ohpA transport
<221> NAME/KEY: CDS
<222> LOCATION: (2807)..(4720)
<223> OTHER INFORMATION: ohpB monooxygenase
<221> NAME/KEY: CDS
<222> LOCATION: (5721)..(6665)
<223> OTHER INFORMATION: ohpD catechol 2,3-dioxygenase

<400> SEQUENCE: 1
gaattccatg ttcttctcct tgcatgtggc ccgcgttgcc gagggcactg gctcggcctg      60
tcgcccgcag agggcgcatg tccgggtgcc tggatatggc gcgtacggcg tgccctccgg     120
cgttaacccc gaggttggcc acgatgcccc ggccatcagg tctggaatgc tagcgttcca     180
gacgaaggta acccacagtg actcacacca caagtactag aatgcaagct gttgcggtga     240
gcgccgcggc ataaggggga gccatgtccg ggacgccgac ggaaagcctg actcg          295 atg acc acc acc gac acc ggc ccc aag ccg ggc agt gag gcc gcc gcc      343
Met Thr Thr Thr Asp Thr Gly Pro Lys Pro Gly Ser Glu Ala Ala Ala
 1               5                  10                  15 ctg ctc gcc aat gtc cgc acc tcg ggg gcg cgg ctg tcc tcc gcg ttg      391
Leu Leu Ala Asn Val Arg Thr Ser Gly Ala Arg Leu Ser Ser Ala Leu
                20                  25                  30 tac gac att ctg aag aac cgg ctg ctc gaa ggg cgc tat gcg gca ggc      439
Tyr Asp Ile Leu Lys Asn Arg Leu Leu Glu Gly Arg Tyr Ala Ala Gly
            35                  40                  45 gag aag atc gtc gtc gag tcg atc cgg caa gag ttc ggg gtg agc aag      487
Glu Lys Ile Val Val Glu Ser Ile Arg Gln Glu Phe Gly Val Ser Lys
        50                  55                  60 cag ccc gtc atg gac gct ctg cgc cgc ctg tcc agc gac aag ctg gtc      535
Gln Pro Val Met Asp Ala Leu Arg Arg Leu Ser Ser Asp Lys Leu Val
65                  70                  75                  80 cac atc gtt ccc cag gtc ggt tgc gag gtc gtc tcc tac gcc ccg cgc      583
His Ile Val Pro Gln Val Gly Cys Glu Val Val Ser Tyr Ala Pro Arg
                85                  90                  95
```

|  |  |
|---|---|
| gaa gtg gaa gac ttc tac acc ctg ttc ggc ggt ttc gaa ggg acc atc<br>Glu Val Glu Asp Phe Tyr Thr Leu Phe Gly Gly Phe Glu Gly Thr Ile<br>100                                             105                                 110 | 631 |
| gcc gcg gta gcg gcc tcc cgg cgg acc gag gcc cag ttg ctg gag ctg<br>Ala Ala Val Ala Ala Ser Arg Arg Thr Glu Ala Gln Leu Leu Glu Leu<br>115                                          120                              125 | 679 |
| gac ctg atc tcg gcg cgg gtc gac gcc ctg atc acc tcc cac gac ccg<br>Asp Leu Ile Ser Ala Arg Val Asp Ala Leu Ile Thr Ser His Asp Pro<br>130                                        135                               140 | 727 |
| gtg gtc cgc gcc cgc ggg tac cgc gtg cac aac cgg gag ttc cat gcg<br>Val Val Arg Ala Arg Gly Tyr Arg Val His Asn Arg Glu Phe His Ala<br>145                                      150                               155                              160 | 775 |
| gcc atc cac gcg atg gcg cac tcg cgg atc atg gag gag acc agc cag<br>Ala Ile His Ala Met Ala His Ser Arg Ile Met Glu Glu Thr Ser Gln<br>                     165                                   170                              175 | 823 |
| cga atg tgg gat ctg tcg gac ttc ttg atc aac acc acc ggc atc acc<br>Arg Met Trp Asp Leu Ser Asp Phe Leu Ile Asn Thr Thr Gly Ile Thr<br>                  180                                    185                               190 | 871 |
| aac ccg ctc tcg agc gca ctg ccc gac cgg cag cat gac cac cac gaa<br>Asn Pro Leu Ser Ser Ala Leu Pro Asp Arg Gln His Asp His His Glu<br>                     195                                   200                              205 | 919 |
| atc acc gag gcc atc cgc aac cgt gac gca gct gcc gcc cgc gag gcc<br>Ile Thr Glu Ala Ile Arg Asn Arg Asp Ala Ala Ala Ala Arg Glu Ala<br>                     210                                   215                              220 | 967 |
| atg gaa cgc cac atc gtc ggc acc atc gca gta atc cgc gac gaa tcc<br>Met Glu Arg His Ile Val Gly Thr Ile Ala Val Ile Arg Asp Glu Ser<br>225                                      230                               235                              240 | 1015 |
| aac gcc cag ctg ccg agc tag accccgatac ccgggccatc gaccggctcc<br>Asn Ala Gln Leu Pro Ser<br>                  245 | 1066 |
| gctatcgcgc cacctacgcc gaggggggac tctcggccgt agcgctgcag acgatccacc | 1126 |
| ggcaccctcc acgctgaccc ctgtctcgcc ctagagggcc ggcgcgccgt cgatcacctt | 1186 |
| taccctcatc cagagacttg cgtcaccctc tatgcccgag tagcgtctga actagacgtc | 1246 |
| tagcattcta gttga        gtg ctc cct ctc gaa gat tct cca gag<br>                                       Val Leu Pro Leu Glu Asp Ser Pro Glu<br>                                                                        250                              255 | 1288 |
| aac ccc tct cga aca tcc cca gaa gaa agg agc ggc cat gac gac cgc<br>Asn Pro Ser Arg Thr Ser Pro Glu Glu Arg Ser Gly His Asp Asp Arg<br>                     260                                   265                              270 | 1336 |
| ttc gca cgc atc gtc ctt cgg ggc acg agc cca ctt ccg ccc aca gat<br>Phe Ala Arg Ile Val Leu Arg Gly Thr Ser Pro Leu Pro Pro Thr Asp<br>                     275                                   280                              285 | 1384 |
| cgg gga agc ccg acc gtg agc acc aca cct acc tcc ccg acg aag acc<br>Arg Gly Ser Pro Thr Val Ser Thr Thr Pro Thr Ser Pro Thr Lys Thr<br>                     290                                   295                              300 | 1432 |
| tca ccg ctg cgg gta gcg atg gcc agc ttc atc ggt acc acc gtc gag<br>Ser Pro Leu Arg Val Ala Met Ala Ser Phe Ile Gly Thr Thr Val Glu<br>305                                      310                               315 | 1480 |
| tac tac gac ttc ttc atc tac ggc acc gcg gcc gcg ctg gta ttc cct<br>Tyr Tyr Asp Phe Phe Ile Tyr Gly Thr Ala Ala Ala Leu Val Phe Pro<br>320                                      325                                   330                              335 | 1528 |
| gag ttg ttc ttc ccg gat gtc tcg tcc gcg atc gga atc ctg ttg tcg<br>Glu Leu Phe Phe Pro Asp Val Ser Ser Ala Ile Gly Ile Leu Leu Ser<br>                     340                                   345                              350 | 1576 |
| ttc gcg acc ttc agc gtt ggg ttc ctc gcc cgc ccg ctg ggt ggc ata<br>Phe Ala Thr Phe Ser Val Gly Phe Leu Ala Arg Pro Leu Gly Gly Ile<br>                     355                                   360                              365 | 1624 |
| gtg ttc ggg cac ttc ggt gac cgg gtc ggc cgc aag cag atg ctg gtg | 1672 |

-continued

```
            Val Phe Gly His Phe Gly Asp Arg Val Gly Arg Lys Gln Met Leu Val
                        370                 375                 380 atc tcc ctg gtc gga atg ggc tcg gcc acc gta ctg atg gga ttg ttg         1720
Ile Ser Leu Val Gly Met Gly Ser Ala Thr Val Leu Met Gly Leu Leu
385                 390                 395 ccc ggt tac gcc caa atc ggg atc gcc gcc ccc atc ctg ctg acc ctg         1768
Pro Gly Tyr Ala Gln Ile Gly Ile Ala Ala Pro Ile Leu Leu Thr Leu
400                 405                 410                 415 ctg cgc ctg gtg cag ggc ttt gcc gtc ggc ggc gag tgg ggt gga gcc         1816
Leu Arg Leu Val Gln Gly Phe Ala Val Gly Gly Glu Trp Gly Gly Ala
                420                 425                 430 acc ctg atg gcc gtc gag cac gcc ccc acc gcg aag aag ggc ttt ttc         1864
Thr Leu Met Ala Val Glu His Ala Pro Thr Ala Lys Lys Gly Phe Phe
            435                 440                 445 gga tcc ttc tcc cag atg ggg gca ccc gcc ggg acc agc gtc gca acc         1912
Gly Ser Phe Ser Gln Met Gly Ala Pro Ala Gly Thr Ser Val Ala Thr
        450                 455                 460 ctg gcg ttc ttc gcg gtc tcc caa ttg ccc gac gag cag ttc ctg agt         1960
Leu Ala Phe Phe Ala Val Ser Gln Leu Pro Asp Glu Gln Phe Leu Ser
465                 470                 475 tgg ggc tgg cga ctg ccg ttc ctg ttc agc gcg gtg ctg atc gtg atc         2008
Trp Gly Trp Arg Leu Pro Phe Leu Phe Ser Ala Val Leu Ile Val Ile
480                 485                 490                 495 ggg ctg ttc att cgc ctg tcc ctg gcc gaa agc ccc gac ttc gcc gag         2056
Gly Leu Phe Ile Arg Leu Ser Leu Ala Glu Ser Pro Asp Phe Ala Glu
                500                 505                 510 gtg aag gca cag agc gcc gtg gtg cga atg ccg atc gcc gaa gcg ttc         2104
Val Lys Ala Gln Ser Ala Val Val Arg Met Pro Ile Ala Glu Ala Phe
            515                 520                 525 cgc aag cac tgg aag gaa att ctc ctc atc gcg ggc acc tac ctg tcc         2152
Arg Lys His Trp Lys Glu Ile Leu Leu Ile Ala Gly Thr Tyr Leu Ser
        530                 535                 540 caa gga gtg ttc gcc tat atc tgc atg gcc tac ctc gtc tcc tac ggc         2200
Gln Gly Val Phe Ala Tyr Ile Cys Met Ala Tyr Leu Val Ser Tyr Gly
545                 550                 555 acc acc gtc gcg ggg atc agc cgc acc ttc gcc ctg gcc gga gta ttc         2248
Thr Thr Val Ala Gly Ile Ser Arg Thr Phe Ala Leu Ala Gly Val Phe
560                 565                 570                 575 gtc gcc ggc atc gtc gcc gtc ctc ctc tac ctc gtg ttc ggc gct ctg         2296
Val Ala Gly Ile Val Ala Val Leu Leu Tyr Leu Val Phe Gly Ala Leu
                580                 585                 590 tcc gac act ttc ggc cgc aag acc atg tac ctg ctc ggc gcc gcc gcg         2344
Ser Asp Thr Phe Gly Arg Lys Thr Met Tyr Leu Leu Gly Ala Ala Ala
            595                 600                 605 atg ggt gtg gtg atc gcc ccc gcc ttc gca ctg atc aac acc ggc aac         2392
Met Gly Val Val Ile Ala Pro Ala Phe Ala Leu Ile Asn Thr Gly Asn
        610                 615                 620 ccg tgg ctg ttc atg gcc gcg cag gtg ctg gtc ttc gga att gca atg         2440
Pro Trp Leu Phe Met Ala Ala Gln Val Leu Val Phe Gly Ile Ala Met
625                 630                 635 gcc ccc gcc gcc ggc gtg aca ggc tcc ctg ttc acg atg gtc ttc gac         2488
Ala Pro Ala Ala Gly Val Thr Gly Ser Leu Phe Thr Met Val Phe Asp
640                 645                 650                 655 gcg gac gtg cgc tac agc ggt gtc tct atc ggc tac acc atc tcc cag         2536
Ala Asp Val Arg Tyr Ser Gly Val Ser Ile Gly Tyr Thr Ile Ser Gln
                660                 665                 670 gtc gcc ggc tcc gcg ttc gcc ccg acg atc gcg acc gcc ttg tac gcc         2584
Val Ala Gly Ser Ala Phe Ala Pro Thr Ile Ala Thr Ala Leu Tyr Ala
            675                 680                 685
```

```
tcc acc aac acc agc aac tcg atc gtg acc tac ctg ctg atc gtc tcg    2632
Ser Thr Asn Thr Ser Asn Ser Ile Val Thr Tyr Leu Leu Ile Val Ser
            690                 695                 700 gcc atc tcg atc gtc tcg gtg atc ctg ctg ccc ggc ggc tgg ggg cgc    2680
Ala Ile Ser Ile Val Ser Val Ile Leu Leu Pro Gly Gly Trp Gly Arg
        705                 710                 715 aag ggc gct gcg agc cag ctc act cgc gac cag gcc acc tcc aca ccg    2728
Lys Gly Ala Ala Ser Gln Leu Thr Arg Asp Gln Ala Thr Ser Thr Pro
720                 725                 730                 735 aaa atg cct gac acc gaa aca ttt tcg act cgg aca gtt ccg gac acc    2776
Lys Met Pro Asp Thr Glu Thr Phe Ser Thr Arg Thr Val Pro Asp Thr
                740                 745                 750 gca gca tcc ctg cgc gtc ctc gac aag tga a gtg atg aca gac atg agt  2825
Ala Ala Ser Leu Arg Val Leu Asp Lys       Val Met Thr Asp Met Ser
            755                 760                     765 gac cac gac cgc acc tcc tac gac acc gac gtc gtg atc gtc ggc ctc    2873
Asp His Asp Arg Thr Ser Tyr Asp Thr Asp Val Val Ile Val Gly Leu
        770                 775                 780 ggc ccc gcc ggt ggc aca gcg gcg ctt gcc ctg gcc agc tac ggc atc    2921
Gly Pro Ala Gly Gly Thr Ala Ala Leu Ala Leu Ala Ser Tyr Gly Ile
                785                 790                 795 cgc gtt cac gcc gtc tcg atg ttc ccc tgg gtg gcg aac tcg ccg cgc    2969
Arg Val His Ala Val Ser Met Phe Pro Trp Val Ala Asn Ser Pro Arg
800                 805                 810 gcg cac atc acc aac cag cgc gcc gtc gaa gtg ctg cgt gac ctg ggc    3017
Ala His Ile Thr Asn Gln Arg Ala Val Glu Val Leu Arg Asp Leu Gly
815                 820                 825                 830 gtc gaa gac gag gcg cgc aac tac gcc acc ccg tgg gac cag atg ggc    3065
Val Glu Asp Glu Ala Arg Asn Tyr Ala Thr Pro Trp Asp Gln Met Gly
                835                 840                 845 gac acg ctg ttc acc acg agc ctg gcc ggc gag gag atc gtc cgg atg    3113
Asp Thr Leu Phe Thr Thr Ser Leu Ala Gly Glu Glu Ile Val Arg Met
        850                 855                 860 cag acc tgg ggt acg ggc gat atc cgc tac ggg gac tac ctg tcc gga    3161
Gln Thr Trp Gly Thr Gly Asp Ile Arg Tyr Gly Asp Tyr Leu Ser Gly
                865                 870                 875 agc ccc tgc acg atg ctc gac att ccg cag ccc ctg atg gag ccg gtg    3209
Ser Pro Cys Thr Met Leu Asp Ile Pro Gln Pro Leu Met Glu Pro Val
880                 885                 890 ctg atc aag aac gcc gcc gaa cgt ggt gcg gtc atc agc ttc aac acc    3257
Leu Ile Lys Asn Ala Ala Glu Arg Gly Ala Val Ile Ser Phe Asn Thr
895                 900                 905                 910 gaa tac ctc gac cac gcc cag gac gag gac ggg gtg acc gtc cgg ttc    3305
Glu Tyr Leu Asp His Ala Gln Asp Glu Asp Gly Val Thr Val Arg Phe
                915                 920                 925 cgc gac gtc cgc tcg ggc acc gtg ttc acc cag cga gcc cgc ttc ctg    3353
Arg Asp Val Arg Ser Gly Thr Val Phe Thr Gln Arg Ala Arg Phe Leu
        930                 935                 940 ctc ggt ttc gac ggc gca cga tcg aag atc gcc gaa cag atc ggg ctt    3401
Leu Gly Phe Asp Gly Ala Arg Ser Lys Ile Ala Glu Gln Ile Gly Leu
                945                 950                 955 ccg ttc gaa ggt gaa ctc gcc cgc gcc ggt acc gcg tac atc ctg ttc    3449
Pro Phe Glu Gly Glu Leu Ala Arg Ala Gly Thr Ala Tyr Ile Leu Phe
960                 965                 970 aac gcg gac ctg agc aaa tat gtc gct cat cgg ccg agc atc ttg cac    3497
Asn Ala Asp Leu Ser Lys Tyr Val Ala His Arg Pro Ser Ile Leu His
975                 980                 985                 990 tgg atc gtc aac tcg aag gcc ggt ttc ggt gag atc ggc atg ggt ctg    3545
Trp Ile Val Asn Ser Lys Ala Gly Phe Gly Glu Ile Gly Met Gly Leu
                995                 1000                1005
```

```
ctg cgc gcg atc cga ccg tgg gac cag tgg atc gcc ggc tgg ggc ttc        3593
Leu Arg Ala Ile Arg Pro Trp Asp Gln Trp Ile Ala Gly Trp Gly Phe
        1010                1015                1020 gac atg gcg aac ggc gag ccg gat gtc tcc gac gac gtt gtc ctc gaa        3641
Asp Met Ala Asn Gly Glu Pro Asp Val Ser Asp Asp Val Val Leu Glu
    1025                1030                1035 cag atc cgg acc ctc gtc ggc gac ccg cac ctg gac gtc gag atc gtg        3689
Gln Ile Arg Thr Leu Val Gly Asp Pro His Leu Asp Val Glu Ile Val
1040                1045                1050 tcg agg tcc ttc tgg tac gtc aac cgg cag tgg gct gag cac tac cag        3737
Ser Arg Ser Phe Trp Tyr Val Asn Arg Gln Trp Ala Glu His Tyr Gln
        1055                1060                1065                1070 tcc ggt cga gtg ttc tgc ggc ggc gac gcg gtg cac cgg cat ccg ccg        3785
Ser Gly Arg Val Phe Cys Gly Gly Asp Ala Val His Arg His Pro Pro
    1075                1080                1085 agc agc ggg ctg ggc tcg aac acg tcc atg cag gac gcg ttc aac ctg        3833
Ser Ser Gly Leu Gly Ser Asn Thr Ser Met Gln Asp Ala Phe Asn Leu
1090                1095                1100 gca tgg aag atc gcg ttc gtc gtg aag ggg tat gca gga ccg ggt ctg        3881
Ala Trp Lys Ile Ala Phe Val Val Lys Gly Tyr Ala Gly Pro Gly Leu
        1105                1110                1115 ctc gag tcc tac tct cct gag cgt gtt ccg gtc ggc aaa cag atc gtc        3929
Leu Glu Ser Tyr Ser Pro Glu Arg Val Pro Val Gly Lys Gln Ile Val
    1120                1125                1130 gct cgc gcc aac cag tcc cgc aag gac tac gcc ggg ctg cgc gaa tgg        3977
Ala Arg Ala Asn Gln Ser Arg Lys Asp Tyr Ala Gly Leu Arg Glu Trp
1135                1140                1145                1150 ttc gat cac gag agc gac gac ccg gtc gcc gcc ggc ctg gca aag ttg        4025
Phe Asp His Glu Ser Asp Asp Pro Val Ala Ala Gly Leu Ala Lys Leu
        1155                1160                1165 aag gaa ccc tcg tcc gaa ggt gtt gct ctg cgt gag cgg ctg tac gag        4073
Lys Glu Pro Ser Ser Glu Gly Val Ala Leu Arg Glu Arg Leu Tyr Glu
    1170                1175                1180 gcg ctg gag gtg aag aac gcc gaa ttc aac gcc cag ggc gtc gaa ctc        4121
Ala Leu Glu Val Lys Asn Ala Glu Phe Asn Ala Gln Gly Val Glu Leu
1185                1190                1195 aac cag cgc tac acc tcg tcc gcg gtc gtt ccc gac ccc gag gcg ggc        4169
Asn Gln Arg Tyr Thr Ser Ser Ala Val Val Pro Asp Pro Glu Ala Gly
        1200                1205                1210 gag gaa gtg tgg gtg cgc gat cgt gag ctg tac ctg cag gcc acc acc        4217
Glu Glu Val Trp Val Arg Asp Arg Glu Leu Tyr Leu Gln Ala Thr Thr
1215                1220                1225                1230 cgg ccg ggc gcg aag ctg ccg cat gcg tgg ctg gtc ggc gcc gac gga        4265
Arg Pro Gly Ala Lys Leu Pro His Ala Trp Leu Val Gly Ala Asp Gly
        1235                1240                1245 acc cgc atc tcc acc ctc gac gtc acc ggc aag gga atg atg acc ctg        4313
Thr Arg Ile Ser Thr Leu Asp Val Thr Gly Lys Gly Met Met Thr Leu
    1250                1255                1260 ctg acc gga ctc ggc ggc cag gca tgg aag cgt gcc gcc gcc aaa ctc        4361
Leu Thr Gly Leu Gly Gly Gln Ala Trp Lys Arg Ala Ala Ala Lys Leu
1265                1270                1275 gac ctg ccg ttc ctg cgg acc gtc gtt gtc ggc gaa ccc ggc acc atc        4409
Asp Leu Pro Phe Leu Arg Thr Val Val Val Gly Glu Pro Gly Thr Ile
        1280                1285                1290 gac cct tac gga tac tgg cgg cgg gtc cgc gac atc gac gag gcc ggc        4457
Asp Pro Tyr Gly Tyr Trp Arg Arg Val Arg Asp Ile Asp Glu Ala Gly
1295                1300                1305                1310 gcc ctg ctc gtg cgg ccc gac ggc tac gtc gcg tgg cga cac agt gct        4505
Ala Leu Leu Val Arg Pro Asp Gly Tyr Val Ala Trp Arg His Ser Ala
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     |     | 1315 |     |     |     |     | 1320 |     |     |     |     | 1325 |     |      |
| ccg | gtc | tgg | gac | gac | acc | gaa | gcg | ctc | acc | agc | ctc | gag | aac | gct | ctc | 4553 |
| Pro | Val | Trp | Asp | Asp | Thr | Glu | Ala | Leu | Thr | Ser | Leu | Glu | Asn | Ala | Leu |      |
|     |     |     |     | 1330 |     |     |     |     | 1335 |     |     |     |     | 1340 |     |      |
| acc | gcg | gtc | ctc | gac | cac | tcg | gcc | agc | gac | aac | ggg | aac | ccg | agc | ggc | 4601 |
| Thr | Ala | Val | Leu | Asp | His | Ser | Ala | Ser | Asp | Asn | Gly | Asn | Pro | Ser | Gly |      |
|     |     |     |     | 1345 |     |     |     |     | 1350 |     |     |     |     | 1355 |     |      |
| aca | aac | gag | ccg | cag | tac | agc | acc | cgg | gcc | gtg | ccg | atc | gtc | gtt | ccg | 4649 |
| Thr | Asn | Glu | Pro | Gln | Tyr | Ser | Thr | Arg | Ala | Val | Pro | Ile | Val | Val | Pro |      |
|     |     |     |     | 1360 |     |     |     |     | 1365 |     |     |     |     | 1370 |     |      |
| cac | gtt | acc | gcc | gag | gat | gca | gca | cca | gct | tcc | gcc | acc | cgc | acc | acc | 4697 |
| His | Val | Thr | Ala | Glu | Asp | Ala | Ala | Pro | Ala | Ser | Ala | Thr | Arg | Thr | Thr |      |
| 1375 |     |     |     |     | 1380 |     |     |     |     | 1385 |     |     |     |     | 1390 |      |
| aca | gtc | gag | gga | gag | aac | cga | tga | cccgtcctta | | caccagcgtc | | tgggacgacc | | | | 4751 |
| Thr | Val | Glu | Gly | Glu | Asn | Arg |   |   |   |   |   |   |   |   |   |      |
|     |     |     |     | 1395 |     |     |     |     |     |     |     |     |     |     |     |      |

| tgaaccaggt cgagttcagc cagggattca tccaggccgg ccctaccgg acccgatacc | 4811 |
| --- | --- |
| tgcacgccgg cgattcgtcc aagcccacgc tgatcctgct gcacggcatc accggccacg | 4871 |
| ccgaggcgta cgtgcgcaat ctgcgctcgc attccgagca cttcaacgtc tgggcaatcg | 4931 |
| acttcatcgg ccacggctat tcgaccaagc ccgaccaccc gctcgagatc aagcactaca | 4991 |
| tcgaccacgt gctgcagttg ctggacgcca tcggcgtcga aaggcctcg ttttccgggg | 5051 |
| agtctctcgg cggttgggtc accgcccagt tcgcgcacga ccatcccgag aaggtcgacc | 5111 |
| ggatcgtgct caacaccatg gcggcacca tggccaaccc tcaggtgatg aacgtctct | 5171 |
| atacctgtc gatggaagcg gcgaaggacc cgagctggga acgcgtcaaa gcacgcctcg | 5231 |
| aatggctcat ggccgacccg accatggtca ccgacgacct gatccgcacc cgccaggcca | 5291 |
| tcttccagca gccggattgg ctcaaggcct gcgagatgaa catggcactg caggacctcg | 5351 |
| aaacccgcaa gcggaacatg atcaccgacg ccactctcaa cggcatcacg gtgcccgcga | 5411 |
| tggtgctgtg gaccaccaag gacccctccg gtccggtcga cgaagccaag cgcatcgcct | 5471 |
| cccacatccc gggcgccaag ctggccatca tggagaactg tggccactgg ccccagtacg | 5531 |
| aggaccccga gaccttcaac aagctgcatc tggacttcct cctcggtcgc agctgacaca | 5591 |
| gaccccggcc ggtgccgcca acccctgcaa ccgggcggc accggccgga tctcacttac | 5651 |
| ccgacctatt gcgctctcgt ccggaccccc ggagagaaag cgccgaagca gcagcaagga | 5711 |

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
| gaccgccgcg | | | atg | cct | gta | gcg | ctg | tgc | gcg | atg | tcg | cac | tcc | ccc | ctg | 5760 |
|   |   |   | Met | Pro | Val | Ala | Leu | Cys | Ala | Met | Ser | His | Ser | Pro | Leu |      |
|   |   |   |     | 1400 |     |     |     |     | 1405 |     |     |     |     | 1410 |     |      |
| atg | gga | cgc | aac | gac | ccc | gaa | cag | gaa | gtc | atc | gac | gcc | gtc | gac | gcc | 5808 |
| Met | Gly | Arg | Asn | Asp | Pro | Glu | Gln | Glu | Val | Ile | Asp | Ala | Val | Asp | Ala |      |
|     |     |     |     | 1415 |     |     |     |     | 1420 |     |     |     |     | 1425 |     |      |
| gca | ttc | gac | cac | gcg | cgc | cgg | ttc | gtc | gcc | gac | ttc | gcc | ccc | gat | ctc | 5856 |
| Ala | Phe | Asp | His | Ala | Arg | Arg | Phe | Val | Ala | Asp | Phe | Ala | Pro | Asp | Leu |      |
|     |     |     |     | 1430 |     |     |     |     | 1435 |     |     |     |     | 1440 |     |      |
| atc | gtc | atc | ttc | gcc | ccc | gac | cac | tac | aac | ggc | gtc | ttc | tac | gac | ctg | 5904 |
| Ile | Val | Ile | Phe | Ala | Pro | Asp | His | Tyr | Asn | Gly | Val | Phe | Tyr | Asp | Leu |      |
|     |     |     |     | 1445 |     |     |     |     | 1450 |     |     |     |     | 1455 |     |      |
| ctg | ccg | ccg | ttc | tgt | atc | ggt | gcc | gcc | gcg | cag | tcc | gtc | ggc | gac | tac | 5952 |
| Leu | Pro | Pro | Phe | Cys | Ile | Gly | Ala | Ala | Ala | Gln | Ser | Val | Gly | Asp | Tyr |      |
|     |     |     |     | 1460 |     |     |     |     | 1465 |     |     |     |     | 1470 |     |      |
| ggc | acc | gaa | gcc | ggc | cct | ctc | gac | gtc | gac | cgt | gac | gcc | gcc | tac | gca | 6000 |
| Gly | Thr | Glu | Ala | Gly | Pro | Leu | Asp | Val | Asp | Arg | Asp | Ala | Ala | Tyr | Ala |      |
| 1475 |     |     |     |     | 1480 |     |     |     |     | 1485 |     |     |     |     | 1490 |      |
| gtc | gcc | cgc | gac | gtc | ctc | gac | agc | ggc | atc | gac | gtc | gca | ttc | tcc | gaa | 6048 |

-continued

```
                    Val Ala Arg Asp Val Leu Asp Ser Gly Ile Asp Val Ala Phe Ser Glu
                                    1495                1500                1505 cgc atg cac gtc gac cac gga ttc gcc caa gca ctc caa ttg ctg gtc        6096
Arg Met His Val Asp His Gly Phe Ala Gln Ala Leu Gln Leu Leu Val
            1510                1515                1520 gga tcg atc acc gcc gtg ccg acc gtg ccg atc ttc atc aat tcg gtc        6144
Gly Ser Ile Thr Ala Val Pro Thr Val Pro Ile Phe Ile Asn Ser Val
        1525                1530                1535 gcc gaa ccg ctc ggc ccg gtc agc cgg gta cgg ctg ctc ggc gag gcg        6192
Ala Glu Pro Leu Gly Pro Val Ser Arg Val Arg Leu Leu Gly Glu Ala
        1540                1545                1550 gtc ggg cgg gcc gct gcc aag ctg gac aag cgt gtg ctg ttc gtc gga        6240
Val Gly Arg Ala Ala Ala Lys Leu Asp Lys Arg Val Leu Phe Val Gly
1555                1560                1565                1570 tcc ggc ggc ctg tcc cac gac ccg ccg gtc ccg cag ttc gcc acc gcg        6288
Ser Gly Gly Leu Ser His Asp Pro Pro Val Pro Gln Phe Ala Thr Ala
                1575                1580                1585 cca gag gaa gtg cgc gag cgg ttg atc gac ggc cgc aat ccc agt gcc        6336
Pro Glu Glu Val Arg Glu Arg Leu Ile Asp Gly Arg Asn Pro Ser Ala
            1590                1595                1600 gcc gaa cgt gat gcc cgc gaa cag cgc gtc atc acc gcc ggg cgg gac        6384
Ala Glu Arg Asp Ala Arg Glu Gln Arg Val Ile Thr Ala Gly Arg Asp
        1605                1610                1615 ttc gcc gcc ggc acc gcc gcc atc cag cca ctg aac ccc gaa tgg gac        6432
Phe Ala Ala Gly Thr Ala Ala Ile Gln Pro Leu Asn Pro Glu Trp Asp
        1620                1625                1630 cgg cac ctg ctc gac gtc ctc gcc tcc ggc gac ctc gag cag atc gac        6480
Arg His Leu Leu Asp Val Leu Ala Ser Gly Asp Leu Glu Gln Ile Asp
1635                1640                1645                1650 gcg tgg acc aac gac tgg ttc gtc gaa cag gcc gga cac tcc tcc cac        6528
Ala Trp Thr Asn Asp Trp Phe Val Glu Gln Ala Gly His Ser Ser His
                1655                1660                1665 gaa gtg cgc acc tgg atc gcc gcg tac gcg gca atg agc gcc gcc ggg        6576
Glu Val Arg Thr Trp Ile Ala Ala Tyr Ala Ala Met Ser Ala Ala Gly
            1670                1675                1680 aag tac cgc gtc acc tcg acc ttc tac cgc gaa atc cac gag tgg ata        6624
Lys Tyr Arg Val Thr Ser Thr Phe Tyr Arg Glu Ile His Glu Trp Ile
        1685                1690                1695 gca gga ttc ggg att act acc gcc gtc gcc gtc gac gaa tag                6666
Ala Gly Phe Gly Ile Thr Thr Ala Val Ala Val Asp Glu
        1700                1705                1710 accccgccgc tcccgccccg cagtcccaac gaagggtggc cccggatgac ctccgtccgc      6726
ccgtgctcgc cgtcggtgaa cgcgggctgg tcggtgggca ggaagacctc atcgccgaca      6786
tcgccctcga cctcgcagct cgtcagtagg aatgcgcacg gccgacgag tcgcgctggt       6846 caccggggcc agccgcggca tcgggcggc catcgcagat gcggtggccg cctccggtgc       6906
cgccgtaatc gtccactacg gatccgatcg gacggccgcc gctgcggtgt cgacggcatc     6966
acggctgccg ggggcctcgc ggctgcggtc caggccgacc tgtcccgacc cgaggggcct     7026 gaaagagctga tgcggagtt cgactccgcg ctcgacggtc tcgggctcga ccgagggctc    7086
gacatcctcg tcaacaacgc cggaatcagt cggcgcggag cgctcgagcg cgtcactgtc     7146
gaggatttcg accgtctggt cgcactcaac cagcgcgccc cgttcttcgt gactcggcat     7206
gccctgcccc ggatgcacga cggcggtcgc atcgtcaaca tttcctccgg atccgcccgc    7266
tacgccagac ccgacgtcat cagctacgcc atgaccaagg gggcgatcga ggtgctcacc     7326
cgcgccctcg ccgtagacgt cggcgaacga ggcatcaccg ccaacgccgt ggcgccggcc     7386
```

-continued

```
gcgctcgata ccgacatgaa cgcgcactgg cttcgcggtg acgaccatgc ccgcaccacc    7446
gccgcgtcca ccactgcact gcgaaaactc gccaccgcgg aggacatcgc cgcgatcgtg    7506
gccttcctcg tcagcgccgc cgccggtgcg atcaccgggc aggtcatcga cgccaccaac    7566
ggcaaccggc tctaaccaga acttaccegg tccc                                 7600
```

<210> SEQ ID NO 2
<211> LENGTH: 246
<212> TYPE: PRT
<213> ORGANISM: Rhodococcus sp.

<400> SEQUENCE: 2

```
Met Thr Thr Thr Asp Thr Gly Pro Lys Pro Gly Ser Glu Ala Ala Ala
  1               5                  10                  15

Leu Leu Ala Asn Val Arg Thr Ser Gly Ala Arg Leu Ser Ser Ala Leu
             20                  25                  30

Tyr Asp Ile Leu Lys Asn Arg Leu Leu Glu Gly Arg Tyr Ala Ala Gly
         35                  40                  45

Glu Lys Ile Val Val Glu Ser Ile Arg Gln Glu Phe Gly Val Ser Lys
     50                  55                  60

Gln Pro Val Met Asp Ala Leu Arg Arg Leu Ser Ser Asp Lys Leu Val
 65                  70                  75                  80

His Ile Val Pro Gln Val Gly Cys Glu Val Val Ser Tyr Ala Pro Arg
                 85                  90                  95

Glu Val Glu Asp Phe Tyr Thr Leu Phe Gly Gly Phe Glu Gly Thr Ile
            100                 105                 110

Ala Ala Val Ala Ala Ser Arg Arg Thr Glu Ala Gln Leu Leu Glu Leu
        115                 120                 125

Asp Leu Ile Ser Ala Arg Val Asp Ala Leu Ile Thr Ser His Asp Pro
    130                 135                 140

Val Val Arg Ala Arg Gly Tyr Arg Val His Asn Arg Glu Phe His Ala
145                 150                 155                 160

Ala Ile His Ala Met Ala His Ser Arg Ile Met Glu Glu Thr Ser Gln
                165                 170                 175

Arg Met Trp Asp Leu Ser Asp Phe Leu Ile Asn Thr Thr Gly Ile Thr
            180                 185                 190

Asn Pro Leu Ser Ser Ala Leu Pro Asp Arg Gln His Asp His His Glu
        195                 200                 205

Ile Thr Glu Ala Ile Arg Asn Arg Asp Ala Ala Ala Arg Glu Ala
    210                 215                 220

Met Glu Arg His Ile Val Gly Thr Ile Ala Val Ile Arg Asp Glu Ser
225                 230                 235                 240

Asn Ala Gln Leu Pro Ser
                245
```

<210> SEQ ID NO 3
<211> LENGTH: 514
<212> TYPE: PRT
<213> ORGANISM: Rhodococcus sp.

<400> SEQUENCE: 3

```
Val Leu Pro Leu Glu Asp Ser Pro Glu Asn Pro Ser Arg Thr Ser Pro
  1               5                  10                  15

Glu Glu Arg Ser Gly His Asp Asp Arg Phe Ala Arg Ile Val Leu Arg
             20                  25                  30

Gly Thr Ser Pro Leu Pro Pro Thr Asp Arg Gly Ser Pro Thr Val Ser
```

```
                35                  40                  45
Thr Thr Pro Thr Ser Pro Thr Lys Thr Ser Pro Leu Arg Val Ala Met
         50                  55                  60

Ala Ser Phe Ile Gly Thr Thr Val Glu Tyr Tyr Asp Phe Phe Ile Tyr
65                  70                  75                  80

Gly Thr Ala Ala Ala Leu Val Phe Pro Glu Leu Phe Phe Pro Asp Val
                 85                  90                  95

Ser Ser Ala Ile Gly Ile Leu Leu Ser Phe Ala Thr Phe Ser Val Gly
                100                 105                 110

Phe Leu Ala Arg Pro Leu Gly Gly Ile Val Phe Gly His Phe Gly Asp
             115                 120                 125

Arg Val Gly Arg Lys Gln Met Leu Val Ile Ser Leu Val Gly Met Gly
         130                 135                 140

Ser Ala Thr Val Leu Met Gly Leu Leu Pro Gly Tyr Ala Gln Ile Gly
145                 150                 155                 160

Ile Ala Ala Pro Ile Leu Leu Thr Leu Leu Arg Leu Val Gln Gly Phe
                165                 170                 175

Ala Val Gly Gly Glu Trp Gly Gly Ala Thr Leu Met Ala Val Glu His
             180                 185                 190

Ala Pro Thr Ala Lys Lys Gly Phe Phe Gly Ser Phe Ser Gln Met Gly
         195                 200                 205

Ala Pro Ala Gly Thr Ser Val Ala Thr Leu Ala Phe Phe Ala Val Ser
     210                 215                 220

Gln Leu Pro Asp Glu Gln Phe Leu Ser Trp Gly Trp Arg Leu Pro Phe
225                 230                 235                 240

Leu Phe Ser Ala Val Leu Ile Val Ile Gly Leu Phe Ile Arg Leu Ser
                245                 250                 255

Leu Ala Glu Ser Pro Asp Phe Ala Glu Val Lys Ala Gln Ser Ala Val
             260                 265                 270

Val Arg Met Pro Ile Ala Glu Ala Phe Arg Lys His Trp Lys Glu Ile
         275                 280                 285

Leu Leu Ile Ala Gly Thr Tyr Leu Ser Gln Gly Val Phe Ala Tyr Ile
     290                 295                 300

Cys Met Ala Tyr Leu Val Ser Tyr Gly Thr Thr Val Ala Gly Ile Ser
305                 310                 315                 320

Arg Thr Phe Ala Leu Ala Gly Val Phe Val Ala Gly Ile Val Ala Val
                325                 330                 335

Leu Leu Tyr Leu Val Phe Gly Ala Leu Ser Asp Thr Phe Gly Arg Lys
             340                 345                 350

Thr Met Tyr Leu Leu Gly Ala Ala Met Gly Val Val Ile Ala Pro
         355                 360                 365

Ala Phe Ala Leu Ile Asn Thr Gly Asn Pro Trp Leu Phe Met Ala Ala
     370                 375                 380

Gln Val Leu Val Phe Gly Ile Ala Met Ala Pro Ala Ala Gly Val Thr
385                 390                 395                 400

Gly Ser Leu Phe Thr Met Val Phe Asp Ala Asp Val Arg Tyr Ser Gly
                405                 410                 415

Val Ser Ile Gly Tyr Thr Ile Ser Gln Val Ala Gly Ser Ala Phe Ala
             420                 425                 430

Pro Thr Ile Ala Thr Ala Leu Tyr Ala Ser Thr Asn Thr Ser Asn Ser
         435                 440                 445

Ile Val Thr Tyr Leu Leu Ile Val Ser Ala Ile Ser Ile Val Ser Val
     450                 455                 460
```

```
Ile Leu Leu Pro Gly Gly Trp Gly Arg Lys Gly Ala Ala Ser Gln Leu
465                 470                 475                 480

Thr Arg Asp Gln Ala Thr Ser Thr Pro Lys Met Pro Asp Thr Glu Thr
                485                 490                 495

Phe Ser Thr Arg Thr Val Pro Asp Thr Ala Ala Ser Leu Arg Val Leu
            500                 505                 510

Asp Lys

<210> SEQ ID NO 4
<211> LENGTH: 637
<212> TYPE: PRT
<213> ORGANISM: Rhodococcus sp.

<400> SEQUENCE: 4

Val Met Thr Asp Met Ser Asp His Asp Arg Thr Ser Tyr Asp Thr Asp
1               5                   10                  15

Val Val Ile Val Gly Leu Gly Pro Ala Gly Gly Thr Ala Ala Leu Ala
                20                  25                  30

Leu Ala Ser Tyr Gly Ile Arg Val His Ala Val Ser Met Phe Pro Trp
            35                  40                  45

Val Ala Asn Ser Pro Arg Ala His Ile Thr Asn Gln Arg Ala Val Glu
        50                  55                  60

Val Leu Arg Asp Leu Gly Val Glu Asp Glu Ala Arg Asn Tyr Ala Thr
65                  70                  75                  80

Pro Trp Asp Gln Met Gly Asp Thr Leu Phe Thr Thr Ser Leu Ala Gly
                85                  90                  95

Glu Glu Ile Val Arg Met Gln Thr Trp Gly Thr Gly Asp Ile Arg Tyr
                100                 105                 110

Gly Asp Tyr Leu Ser Gly Ser Pro Cys Thr Met Leu Asp Ile Pro Gln
            115                 120                 125

Pro Leu Met Glu Pro Val Leu Ile Lys Asn Ala Ala Glu Arg Gly Ala
        130                 135                 140

Val Ile Ser Phe Asn Thr Glu Tyr Leu Asp His Ala Gln Asp Glu Asp
145                 150                 155                 160

Gly Val Thr Val Arg Phe Arg Asp Val Arg Ser Gly Thr Val Phe Thr
                165                 170                 175

Gln Arg Ala Arg Phe Leu Leu Gly Phe Asp Gly Ala Arg Ser Lys Ile
            180                 185                 190

Ala Glu Gln Ile Gly Leu Pro Phe Glu Gly Glu Leu Ala Arg Ala Gly
        195                 200                 205

Thr Ala Tyr Ile Leu Phe Asn Ala Asp Leu Ser Lys Tyr Val Ala His
        210                 215                 220

Arg Pro Ser Ile Leu His Trp Ile Val Asn Ser Lys Ala Gly Phe Gly
225                 230                 235                 240

Glu Ile Gly Met Gly Leu Leu Arg Ala Ile Arg Pro Trp Asp Gln Trp
                245                 250                 255

Ile Ala Gly Trp Gly Phe Asp Met Ala Asn Gly Glu Pro Asp Val Ser
            260                 265                 270

Asp Asp Val Val Leu Glu Gln Ile Arg Thr Leu Val Gly Asp Pro His
        275                 280                 285

Leu Asp Val Glu Ile Val Ser Arg Ser Phe Trp Tyr Val Asn Arg Gln
        290                 295                 300

Trp Ala Glu His Tyr Gln Ser Gly Arg Val Phe Cys Gly Gly Asp Ala
305                 310                 315                 320
```

```
Val His Arg His Pro Pro Ser Ser Gly Leu Gly Ser Asn Thr Ser Met
                325                 330                 335

Gln Asp Ala Phe Asn Leu Ala Trp Lys Ile Ala Phe Val Val Lys Gly
            340                 345                 350

Tyr Ala Gly Pro Gly Leu Leu Glu Ser Tyr Ser Pro Glu Arg Val Pro
        355                 360                 365

Val Gly Lys Gln Ile Val Ala Arg Ala Asn Gln Ser Arg Lys Asp Tyr
    370                 375                 380

Ala Gly Leu Arg Glu Trp Phe Asp His Glu Ser Asp Pro Val Ala
385                 390                 395                 400

Ala Gly Leu Ala Lys Leu Lys Glu Pro Ser Ser Glu Gly Val Ala Leu
                405                 410                 415

Arg Glu Arg Leu Tyr Glu Ala Leu Glu Val Lys Asn Ala Glu Phe Asn
            420                 425                 430

Ala Gln Gly Val Glu Leu Asn Gln Arg Tyr Thr Ser Ser Ala Val Val
        435                 440                 445

Pro Asp Pro Glu Ala Gly Glu Glu Val Trp Val Arg Asp Arg Glu Leu
    450                 455                 460

Tyr Leu Gln Ala Thr Thr Arg Pro Gly Ala Lys Leu Pro His Ala Trp
465                 470                 475                 480

Leu Val Gly Ala Asp Gly Thr Arg Ile Ser Thr Leu Asp Val Thr Gly
                485                 490                 495

Lys Gly Met Met Thr Leu Leu Thr Gly Leu Gly Gln Ala Trp Lys
            500                 505                 510

Arg Ala Ala Ala Lys Leu Asp Leu Pro Phe Leu Arg Thr Val Val Val
        515                 520                 525

Gly Glu Pro Gly Thr Ile Asp Pro Tyr Gly Tyr Trp Arg Arg Val Arg
    530                 535                 540

Asp Ile Asp Glu Ala Gly Ala Leu Leu Val Arg Pro Asp Gly Tyr Val
545                 550                 555                 560

Ala Trp Arg His Ser Ala Pro Val Trp Asp Asp Thr Glu Ala Leu Thr
                565                 570                 575

Ser Leu Glu Asn Ala Leu Thr Ala Val Leu Asp His Ser Ala Ser Asp
            580                 585                 590

Asn Gly Asn Pro Ser Gly Thr Asn Glu Pro Gln Tyr Ser Thr Arg Ala
        595                 600                 605

Val Pro Ile Val Val Pro His Val Thr Ala Glu Asp Ala Ala Pro Ala
    610                 615                 620

Ser Ala Thr Arg Thr Thr Thr Val Glu Gly Glu Asn Arg
625                 630                 635

<210> SEQ ID NO 5
<211> LENGTH: 314
<212> TYPE: PRT
<213> ORGANISM: Rhodococcus sp.

<400> SEQUENCE: 5

Met Pro Val Ala Leu Cys Ala Met Ser His Ser Pro Leu Met Gly Arg
1               5                   10                  15

Asn Asp Pro Glu Gln Glu Val Ile Asp Ala Val Asp Ala Ala Phe Asp
            20                  25                  30

His Ala Arg Arg Phe Val Ala Asp Phe Ala Pro Asp Leu Ile Val Ile
        35                  40                  45

Phe Ala Pro Asp His Tyr Asn Gly Val Phe Tyr Asp Leu Leu Pro Pro
```

```
            50                  55                  60
Phe Cys Ile Gly Ala Ala Gln Ser Val Gly Asp Tyr Gly Thr Glu
 65                  70                  75                  80

Ala Gly Pro Leu Asp Val Asp Arg Asp Ala Ala Tyr Ala Val Ala Arg
                 85                  90                  95

Asp Val Leu Asp Ser Gly Ile Asp Val Ala Phe Ser Glu Arg Met His
                100                 105                 110

Val Asp His Gly Phe Ala Gln Ala Leu Gln Leu Leu Val Gly Ser Ile
            115                 120                 125

Thr Ala Val Pro Thr Val Pro Ile Phe Ile Asn Ser Val Ala Glu Pro
130                 135                 140

Leu Gly Pro Val Ser Arg Val Arg Leu Leu Gly Glu Ala Val Gly Arg
145                 150                 155                 160

Ala Ala Ala Lys Leu Asp Lys Arg Val Leu Phe Val Gly Ser Gly Gly
                165                 170                 175

Leu Ser His Asp Pro Pro Val Pro Gln Phe Ala Thr Ala Pro Glu Glu
                180                 185                 190

Val Arg Glu Arg Leu Ile Asp Gly Arg Asn Pro Ser Ala Ala Glu Arg
            195                 200                 205

Asp Ala Arg Glu Gln Arg Val Ile Thr Ala Gly Arg Asp Phe Ala Ala
210                 215                 220

Gly Thr Ala Ala Ile Gln Pro Leu Asn Pro Glu Trp Asp Arg His Leu
225                 230                 235                 240

Leu Asp Val Leu Ala Ser Gly Asp Leu Glu Gln Ile Asp Ala Trp Thr
                245                 250                 255

Asn Asp Trp Phe Val Glu Gln Ala Gly His Ser Ser His Glu Val Arg
                260                 265                 270

Thr Trp Ile Ala Ala Tyr Ala Ala Met Ser Ala Ala Gly Lys Tyr Arg
            275                 280                 285

Val Thr Ser Thr Phe Tyr Arg Glu Ile His Glu Trp Ile Ala Gly Phe
        290                 295                 300

Gly Ile Thr Thr Ala Val Ala Val Asp Glu
305                 310

<210> SEQ ID NO 6
<211> LENGTH: 289
<212> TYPE: PRT
<213> ORGANISM: Rhodococcus sp.

<400> SEQUENCE: 6

Met Thr Arg Pro Tyr Thr Ser Val Trp Asp Asp Leu Asn Gln Val Glu
  1               5                  10                  15

Phe Ser Gln Gly Phe Ile Gln Ala Gly Pro Tyr Arg Thr Arg Tyr Leu
                 20                  25                  30

His Ala Gly Asp Ser Ser Lys Pro Thr Leu Ile Leu Leu His Gly Ile
             35                  40                  45

Thr Gly His Ala Glu Ala Tyr Val Arg Asn Leu Arg Ser His Ser Glu
         50                  55                  60

His Phe Asn Val Trp Ala Ile Asp Phe Ile Gly His Gly Tyr Ser Thr
 65                  70                  75                  80

Lys Pro Asp His Pro Leu Glu Ile Lys His Tyr Ile Asp His Val Leu
                 85                  90                  95

Gln Leu Leu Asp Ala Ile Gly Val Glu Lys Ala Ser Phe Ser Gly Glu
                100                 105                 110
```

```
Ser Leu Gly Gly Trp Val Thr Ala Gln Phe Ala His Asp His Pro Glu
            115                 120                 125
Lys Val Asp Arg Ile Val Leu Asn Thr Met Gly Gly Thr Met Ala Asn
130                 135                 140
Pro Gln Val Met Glu Arg Leu Tyr Thr Leu Ser Met Glu Ala Ala Lys
145                 150                 155                 160
Asp Pro Ser Trp Glu Arg Val Lys Ala Arg Leu Glu Trp Leu Met Ala
                165                 170                 175
Asp Pro Thr Met Val Thr Asp Asp Leu Ile Arg Thr Arg Gln Ala Ile
            180                 185                 190
Phe Gln Gln Pro Asp Trp Leu Lys Ala Cys Glu Met Asn Met Ala Leu
        195                 200                 205
Gln Asp Leu Glu Thr Arg Lys Arg Asn Met Ile Thr Asp Ala Thr Leu
    210                 215                 220
Asn Gly Ile Thr Val Pro Ala Met Val Leu Trp Thr Thr Lys Asp Pro
225                 230                 235                 240
Ser Gly Pro Val Asp Glu Ala Lys Arg Ile Ala Ser His Ile Pro Gly
                245                 250                 255
Ala Lys Leu Ala Ile Met Glu Asn Cys Gly His Trp Pro Gln Tyr Glu
            260                 265                 270
Asp Pro Glu Thr Phe Asn Lys Leu His Leu Asp Phe Leu Leu Gly Arg
        275                 280                 285
Ser

<210> SEQ ID NO 7
<211> LENGTH:
<212> TYPE:
<213> ORGANISM:

<400> SEQUENCE: 7

000

<210> SEQ ID NO 8
<211> LENGTH: 27
<212> TYPE: DNA
<213> ORGANISM: Artificial Sequence
<220> FEATURE:
<223> OTHER INFORMATION: Description of Artificial
      Sequence:OHPR3

<400> SEQUENCE: 8
atcgaattcg gatccatgac caccacc                                         27

<210> SEQ ID NO 9
<211> LENGTH: 44
<212> TYPE: DNA
<213> ORGANISM: Artificial Sequence
<220> FEATURE:
<223> OTHER INFORMATION: Description of Artificial
      Sequence:OHPR4

<400> SEQUENCE: 9
atcgcggccg ctctagacta actgcagggc gccaagctcg gcag                      44

<210> SEQ ID NO 10
<211> LENGTH: 24
<212> TYPE: DNA
<213> ORGANISM: Artificial Sequence
<220> FEATURE:
<223> OTHER INFORMATION: Description of Artificial
      Sequence:C11
```

```
<400> SEQUENCE: 10
atcgaattcg gatccacgag agag                                           24

<210> SEQ ID NO 11
<211> LENGTH: 29
<212> TYPE: DNA
<213> ORGANISM: Artificial Sequence
<220> FEATURE:
<223> OTHER INFORMATION: Description of Artificial
      Sequence:C12

<400> SEQUENCE: 11
atccggccgc gctctagagt acgcaagct                                      29

<210> SEQ ID NO 12
<211> LENGTH: 20
<212> TYPE: DNA
<213> ORGANISM: Artificial Sequence
<220> FEATURE:
<223> OTHER INFORMATION: Description of Artificial
      Sequence:op1

<400> SEQUENCE: 12
atcctcgaga ccccgatacc                                                20

<210> SEQ ID NO 13
<211> LENGTH: 17
<212> TYPE: DNA
<213> ORGANISM: Artificial Sequence
<220> FEATURE:
<223> OTHER INFORMATION: Description of Artificial
      Sequence:op2

<400> SEQUENCE: 13
atcgtcgacc gctaccc                                                   17

<210> SEQ ID NO 14
<211> LENGTH: 50
<212> TYPE: DNA
<213> ORGANISM: Artificial Sequence
<220> FEATURE:
<223> OTHER INFORMATION: Description of Artificial
      Sequence:CaMVop2

<400> SEQUENCE: 14
tccactgacg taagggatga cgcacaatcc cactatcctt cgcaagaccc               50

<210> SEQ ID NO 15
<211> LENGTH: 50
<212> TYPE: DNA
<213> ORGANISM: Artificial Sequence
<220> FEATURE:
<223> OTHER INFORMATION: Description of Artificial
      Sequence:CaMVop3

<400> SEQUENCE: 15
atgctagacg tctagttcag acgctactta tatagaggaa gggtcttgcg               50

<210> SEQ ID NO 16
<211> LENGTH: 45
<212> TYPE: DNA
<213> ORGANISM: Artificial Sequence
<220> FEATURE:
<223> OTHER INFORMATION: Description of Artificial
      Sequence:CaMVop4
```

```
<400> SEQUENCE: 16
cgtctagcat tctagttgag gaagttcatt tcatttggag aggac            45

<210> SEQ ID NO 17
<211> LENGTH: 23
<212> TYPE: DNA
<213> ORGANISM: Artificial Sequence
<220> FEATURE:
<223> OTHER INFORMATION: Description of Artificial
      Sequence:CaMVopF1

<400> SEQUENCE: 17
atcgatatct ccactgacgt aag                                    23

<210> SEQ ID NO 18
<211> LENGTH: 24
<212> TYPE: DNA
<213> ORGANISM: Artificial Sequence
<220> FEATURE:
<223> OTHER INFORMATION: Description of Artificial
      Sequence:CaMVopR1

<400> SEQUENCE: 18
gatggatccg tcctctccaa atga                                   24

<210> SEQ ID NO 19
<211> LENGTH: 470
<212> TYPE: DNA
<213> ORGANISM: Artificial Sequence
<220> FEATURE:
<223> OTHER INFORMATION: Description of Artificial Sequence:chimaeric
      promoter

<400> SEQUENCE: 19
catgcctgca ggtcaacatg gtggagcacg acactctcgt ctactccaag aatatcaaag    60
atacagtctc agaagaccag agggctattg agactttca acaaagggta atatcgggaa    120
acctcctcgg attccattgc ccagctatct gtcacttcat cgaaaggaca gtagaaaagg    180
aagatggctt ctacaaatgc catcattgcg ataaaggaaa ggctatcgtt caagaatgcc    240
tctaccgaca gtggtcccaa agatgtaccc ccacccacga ggaacatcgt ggaaaaagaa    300
gacgttccaa ccacgtcttc aaagcaagtg gattgatgtg atatctccac tgacgtaagg    360
gatgacgcac aatcccacta tccttcgcaa gacccttcct ctatataagt agcgtctgaa    420
ctagacgtct agcattctag ttgaggaagt tcatttcatt tggagaggac               470
```

What is claimed is:

1. A system for modulating expression of a target nucleic acid sequence comprising:
   (a) a first nucleic acid sequence operably linked to and regulates the expression of a second nucleic acid sequence, said second nucleic acid sequence encoding a regulator polypeptide; and
   (b) a third nucleic acid sequence operably linked to and regulates the expression of a target nucleic acid sequence, whereby said regulator polypeptide binds to said third nucleic acid sequence and modulates the expression of said target nucleic acid sequence, and wherein said regulator polypeptide comprises (i) the amino acid sequence of SEQ ID NO: 2; or (ii) an amino acid sequence encoded by a nucleotide sequence that hybridizes to the complement of the nucleotide sequence from 295 to 1035 of SEQ ID NO: 1 under hybridization conditions comprising incubating at 37° C. in 1×SSC and 50% formamide, and/or, wherein said third nucleic acid sequence (i) comprises the nucleotide sequence from 1225 to 1260 of SEQ ID NO:1; or (ii) hybridizes to the complement of the nucleotide sequence from 1225 to 1260 of SEQ ID NO:1 under hybridizing conditions comprising incubating at 37° C. in 1×SSC and 50% formamide.

2. The system according to claim 1, wherein said first and/or third nucleic acid comprises a promoter which regulates expression in eukaryotic cells and/or tissues.

3. The system according to claim 1, wherein said first nucleic acid comprises a promoter selected from the group consisting of constitutive, developmentally regulated, tissue-specific, cell-specific, and cell compartment-specific promoter.

4. The system according to claim 3, wherein said constitutive promoter is cauliflower mosaic virus 35S promoter or cauliflower mosaic virus 19S promoter.

5. The system according to claim 3, wherein said tissue-specific promoter is a patatin promoter or a petE promoter.

6. The system according to claim 3, wherein said cell compartment-specific promoter is a chloroplast gene promoter or a mitochondrial gene promoter.

7. The system according to claim 6, wherein said chloroplast gene promoter is from a gene encoding a large subunit of ribulose biphosphate carboxylase.

8. The system according to claim 6, wherein said mitochondrial gene promoter is from a 18S-5S rRNA gene.

9. The system according to claims 1, 2, 3, 4, 5, 6, 7, or 8, wherein said first and/or third nucleic acid sequence comprises one or more enhancer sequences.

10. The system according to claim 9, wherein said enhancer sequence is an intron, or said enhancer sequence is a transcriptional enhancer sequence and/or a translation enhancer sequence.

11. The system according to claim 10, wherein said enhancer sequence is a non-translated leader sequence.

12. The system according to claim 11, wherein said non-translated leader sequence is a viral non-translated leader sequence.

13. The system according to claim 12, wherein said viral non-translated leader sequence is from a virus selected from the group consisting of Tobacco Mosaic Virus (TMV), Maize Chlorotic Mottle Virus (MCMV), Alfalfa Mosaic Virus (AMV), Picornavirus, Potyvirus, and AMV RNA4.

14. The system according to claim 11, wherein said enhancer sequence is a Heat Shock Protein 70 leader sequence.

15. The system according to claim 10, wherein said enhancer sequence is a transcriptional enhancer sequence.

16. The system according to claim 15, wherein said enhancer sequence is a petE enhancer sequence.

17. The system according to claim 10, wherein said enhancer sequence is an intron of the maize Adh1 gene or the Heat Shock Protein 70 intron from maize.

18. The system according claim 1, wherein said regulator polypeptide comprises one or more domains selected from the group consisting of a ligand binding domain, a nucleic acid binding domain, a transactivation domain, a silencing/repressing domain, a dimerization domain, and a targeting domain.

19. The system according to claim 18, wherein said ligand binding domain binds non-covalently to a ligand.

20. The system according to claim 19, wherein said ligand is an inducer, or a precursor of an inducer.

21. The system according to claim 18, wherein said nucleic acid binding domain comprises a sequence of amino acids which binds non-covalently to a response element.

22. The system according to claim 21, wherein said third nucleic acid sequence comprises said response element.

23. The system according to claim 21, wherein said response element is a combination of two or more response elements and responsive to one or more nucleic acid binding proteins.

24. The system according to claim 22, wherein said response element responds to a protein selected from the group consisting of LexA, Ga14, LacI, Tet, C1, and Ace1.

25. The system according to claim 18, wherein said transactivation domain is selected from the group consisting of herpes simplex virus Vp16 domain, maize C1 domain, rice Oshox1 silencing domain, rice Oshox1 repressing domain, and Kruppel Associated Box domain.

26. The system according to claim 18, wherein said targeting domain is selected from the group consisting of a plasma membrane targeting sequence, a golgi targeting sequence, an endoplasmatic reticulum targeting sequence, a nuclear targeting signal, a chloroplast targeting sequence, a mitochondrial targeting sequence, and an inner envelope targeting sequence.

27. The system according to any one of claims 18–26, wherein said second nucleic acid sequence which encodes said domain is modified for expression in eukaryotes.

28. The system according to claim 18, wherein said regulator polypeptide comprises a fusion protein.

29. The system according to claim 18, wherein said regulator polypeptide comprises a ligand binding domain and/or a DNA binding domain.

30. The system according to claim 1, wherein said third nucleic acid sequence comprises a promoter, and a response element that binds said regulator polypeptide.

31. A plasmid deposited under NCIMB Accession No. 40997.

32. The system according to claim 1, wherein the expression of said target nucleic acid sequence is increased by the binding of an inducer to said regulator polypeptide.

33. The system according to claim 32, wherein the inducer is 3-(2-hydroxyphenyl)propionic acid orthohydroxyphenylpropionic acid.

34. The system according to claim 32, wherein said regulator polypeptide is OhpR protein.

35. The system according to claim 32, wherein said third nucleotide sequence comprises a cauliflower mosaic virus 35S promoter.

* * * * *

UNITED STATES PATENT AND TRADEMARK OFFICE
CERTIFICATE OF CORRECTION

| | |
|---|---|
| PATENT NO. | : 6,660,524 B1 |
| APPLICATION NO. | : 09/469211 |
| DATED | : December 9, 2003 |
| INVENTOR(S) | : Türck et al. |

It is certified that error appears in the above-identified patent and that said Letters Patent is hereby corrected as shown below:

On the title page, insert (30) Foreign Priority Data --United Kingdom 9828660.2, filed December 24, 1998--

Column 1, line 7, after "exclusively" insert --involving--

Figure 5:
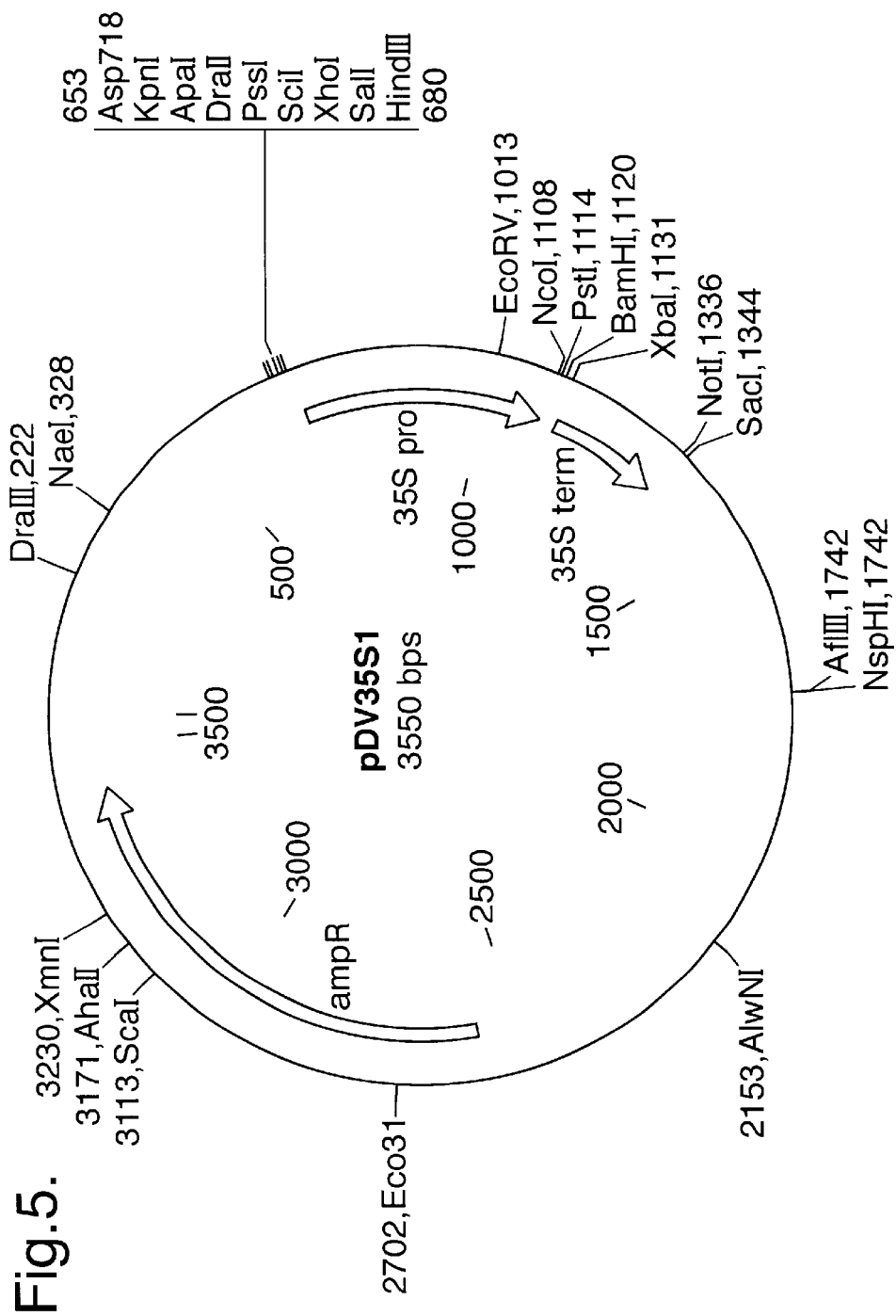
FIG. 5 shows a schematic diagram of the plasmid pSK52040 as used in the present invention. The plasmid contains the CaMV 35S promoter, a GUS intron (Vancanneyt et al., 1990) and a CaMV 35S terminator in pBluescript.

In the Figures, Sheet 5 of 28, change "Fig. 5" to --Fig. 7--
    As shown in attached In the Figures, Sheet 6 of 28, change "Fig. 6" to --Fig. 5--
    As shown in attached In the Figures, Sheet 7 of 28, change "Fig. 7" to --Fig. 6--
    As shown in attached Column 7, line 35, change "No: 13)" to --No: 19)--;

Column 8, line 33, change "No: 13)" to --No: 19)--;

Column 8, line 41, change "No: 13)" to --No: 19)--;

Column 8, line 52, change "Seq. ID. 1)" to --Seq. ID. 19)--;

Column 13, line 66, change "bezene" to --benzene--;

Column 16, line 14, change "pBS52040" to --pSK52040--;

Column 16, line 47, change "SEQ ID NO: 18" to --SEQ ID NO: 19--;

Column 19, line 7, change "the" to --then--;

Column 19, line 24, change "was" to --were--;

Sequence Listing, Columns 21 and 22, after line 15, replace Sequence Listing with corrected Sequence Listing provided herein;
    As shown in the attached sheets Claim 2, Column 50, line 61, after "acid" insert --sequence--;

Claim 3, Column 50, line 64, after "acid" insert --sequence--;

UNITED STATES PATENT AND TRADEMARK OFFICE
CERTIFICATE OF CORRECTION

| | |
|---|---|
| PATENT NO. | : 6,660,524 B1 |
| APPLICATION NO. | : 09/469211 |
| DATED | : December 9, 2003 |
| INVENTOR(S) | : Türck et al. |

It is certified that error appears in the above-identified patent and that said Letters Patent is hereby corrected as shown below:

Claim 36, Column 52, line 49, insert as new Claim 36 --36. The system according to claim 30, wherein said promoter is selected from the group consisting of the A1 core promoter obtained from the A1 gene of maize, the cauliflower mosaic virus 35S core promoter, the cauliflower mosaic virus 35S full-length promoter, and the Carnation etched ring virus promoter.--.

Signed and Sealed this

Twenty-second Day of January, 2008

JON W. DUDAS
*Director of the United States Patent and Trademark Office*

SEQUENCE LISTING

<110> TURCK, JUTTA
      ARCHER, JOHN

<120> CONTROL OF GENE EXPRESSION IN EUKARYOTES

<130> 13101/48201

<140> 09/469,211
<141> 1999-12-22

<150> 9828660.2
<151> 1998-12-24

<160> 19

<170> PatentIn version 3.3

<210> 1
<211> 7599
<212> DNA
<213> Rhodococcus sp.

<220>
<221> CDS
<222> (295)..(1035)

<220>
<221> CDS
<222> (1261)..(2805)

<220>
<221> CDS
<222> (2807)..(4720)

<220>
<221> CDS
<222> (5721)..(6665)

<400> 1

```
gaattccatg ttcttctcct tgcatgtggc ccgcgttgcc gagggcactg ctcggcctgt    60
cgcccgcaga gggcgcatgt ccgggtgcct ggatatggcg cgtacggcgt gccctccggc   120
gttaaccccg aggttggcca cgatgccccg gccatcaggt ctggaatgct agcgttccag   180
acgaaggtaa cccacagtga ctcacaccac aagtactaga atgcaagctg ttgcggtgag   240
cgccgcggca taaggggag ccatgtccgg gacgccgacg gaaagcctga ctcg atg      297
                                                             Met
                                                               1 acc acc acc gac acc ggc ccc aag ccg ggc agt gag gcc gcc gcc ctg    345
Thr Thr Thr Asp Thr Gly Pro Lys Pro Gly Ser Glu Ala Ala Ala Leu
          5                  10                  15
```

```
ctc gcc aat gtc cgc acc tcg ggg gcg cgg ctg tcc tcc gcg ttg tac      393
Leu Ala Asn Val Arg Thr Ser Gly Ala Arg Leu Ser Ser Ala Leu Tyr
        20              25              30 gac att ctg aag aac cgg ctg ctc gaa ggg cgc tat gcg gca ggc gag      441
Asp Ile Leu Lys Asn Arg Leu Leu Glu Gly Arg Tyr Ala Ala Gly Glu
    35              40              45 aag atc gtc gtc gag tcg atc cgg caa gag ttc ggg gtg agc aag cag      489
Lys Ile Val Val Glu Ser Ile Arg Gln Glu Phe Gly Val Ser Lys Gln
50              55              60              65 ccc gtc atg gac gct ctg cgc cgc ctg tcc agc gac aag ctg gtc cac      537
Pro Val Met Asp Ala Leu Arg Arg Leu Ser Ser Asp Lys Leu Val His
            70              75              80 atc gtt ccc cag gtc ggt tgc gag gtc gtc tcc tac gcc ccg cgc gaa      585
Ile Val Pro Gln Val Gly Cys Glu Val Val Ser Tyr Ala Pro Arg Glu
        85              90              95 gtg gaa gac ttc tac acc ctg ttc ggc ggt ttc gaa ggg acc atc gcc      633
Val Glu Asp Phe Tyr Thr Leu Phe Gly Gly Phe Glu Gly Thr Ile Ala
    100             105             110 gcg gta gcg gcc tcc cgg cgg acc gag gcc cag ttg ctg gag ctg gac      681
Ala Val Ala Ala Ser Arg Arg Thr Glu Ala Gln Leu Leu Glu Leu Asp
115             120             125 ctg atc tcg gcg cgg gtc gac gcc ctg atc acc tcc cac gac ccg gtg      729
Leu Ile Ser Ala Arg Val Asp Ala Leu Ile Thr Ser His Asp Pro Val
130             135             140             145 gtc cgc gcc cgc ggg tac cgc gtg cac aac cgg gag ttc cat gcg gcc      777
Val Arg Ala Arg Gly Tyr Arg Val His Asn Arg Glu Phe His Ala Ala
            150             155             160 atc cac gcg atg gcg cac tcg cgg atc atg gag gag acc agc cag cga      825
Ile His Ala Met Ala His Ser Arg Ile Met Glu Glu Thr Ser Gln Arg
        165             170             175 atg tgg gat ctg tcg gac ttc ttg atc aac acc acc ggc atc acc aac      873
Met Trp Asp Leu Ser Asp Phe Leu Ile Asn Thr Thr Gly Ile Thr Asn
    180             185             190 ccg ctc tcg agc gca ctg ccc gac cgg cag cat gac cac cac gaa atc      921
Pro Leu Ser Ser Ala Leu Pro Asp Arg Gln His Asp His His Glu Ile
        195             200             205 acc gag gcc atc cgc aac cgt gac gca gct gcc gcc cgc gag gcc atg      969
Thr Glu Ala Ile Arg Asn Arg Asp Ala Ala Ala Ala Arg Glu Ala Met
210             215             220             225 gaa cgc cac atc gtc ggc acc atc gca gta atc cgc gac gaa tcc aac     1017
Glu Arg His Ile Val Gly Thr Ile Ala Val Ile Arg Asp Glu Ser Asn
            230             235             240
```

```
gcc cag ctg ccg agc tag accccgatac ccgggccatc gaccggctcc         1065
Ala Gln Leu Pro Ser
        245 gctatcgcgc cacctacgcc gagggggac tctcggccgt agcgctgcag acgatccacc  1125 ggcaccctcc acgctgaccc ctgtctcgcc ctagagggcc ggcgcgccgt cgatcacctt  1185 taccctcatc cagagacttg cgtcaccctc tatgcccgag tagcgtctga actagacgtc  1245 tagcattcta gttga gtg ctc cct ctc gaa gat tct cca gag aac ccc tct   1296
              Val Leu Pro Leu Glu Asp Ser Pro Glu Asn Pro Ser
                            250                 255 cga aca tcc cca gaa gaa agg agc ggc cat gac gac cgc ttc gca cgc   1344
Arg Thr Ser Pro Glu Glu Arg Ser Gly His Asp Asp Arg Phe Ala Arg
    260                 265                 270 atc gtc ctt cgg ggc acg agc cca ctt ccg ccc aca gat cgg gga agc   1392
Ile Val Leu Arg Gly Thr Ser Pro Leu Pro Pro Thr Asp Arg Gly Ser
275                 280                 285                 290 ccg acc gtg agc acc aca cct acc tcc ccg acg aag acc tca ccg ctg   1440
Pro Thr Val Ser Thr Thr Pro Thr Ser Pro Thr Lys Thr Ser Pro Leu
                295                 300                 305 cgg gta gcg atg gcc agc ttc atc ggt acc acc gtc gag tac tac gac   1488
Arg Val Ala Met Ala Ser Phe Ile Gly Thr Thr Val Glu Tyr Tyr Asp
        310                 315                 320 ttc ttc atc tac ggc acc gcg gcc gcg ctg gta ttc cct gag ttg ttc   1536
Phe Phe Ile Tyr Gly Thr Ala Ala Ala Leu Val Phe Pro Glu Leu Phe
            325                 330                 335 ttc ccg gat gtc tcg tcc gcg atc gga atc ctg ttg tcg ttc gcg acc   1584
Phe Pro Asp Val Ser Ser Ala Ile Gly Ile Leu Leu Ser Phe Ala Thr
        340                 345                 350 ttc agc gtt ggg ttc ctc gcc cgc ccg ctg ggt ggc ata gtg ttc ggg   1632
Phe Ser Val Gly Phe Leu Ala Arg Pro Leu Gly Gly Ile Val Phe Gly
355                 360                 365                 370 cac ttc ggt gac cgg gtc ggc cgc aag cag atg ctg gtg atc tcc ctg   1680
His Phe Gly Asp Arg Val Gly Arg Lys Gln Met Leu Val Ile Ser Leu
                375                 380                 385 gtc gga atg ggc tcg gcc acc gta ctg atg gga ttg ttg ccc ggt tac   1728
Val Gly Met Gly Ser Ala Thr Val Leu Met Gly Leu Leu Pro Gly Tyr
        390                 395                 400 gcc caa atc ggg atc gcc gcc ccc atc ctg ctg acc ctg ctg cgc ctg   1776
Ala Gln Ile Gly Ile Ala Ala Pro Ile Leu Leu Thr Leu Leu Arg Leu
            405                 410                 415 gtg cag ggc ttt gcc gtc ggc ggc gag tgg ggt gga gcc acc ctg atg   1824
Val Gln Gly Phe Ala Val Gly Gly Glu Trp Gly Gly Ala Thr Leu Met
        420                 425                 430
```

```
gcc gtc gag cac gcc ccc acc gcg aag aag ggc ttt ttc gga tcc ttc    1872
Ala Val Glu His Ala Pro Thr Ala Lys Lys Gly Phe Phe Gly Ser Phe
435                 440                 445                 450 tcc cag atg ggg gca ccc gcc ggg acc agc gtc gca acc ctg gcg ttc    1920
Ser Gln Met Gly Ala Pro Ala Gly Thr Ser Val Ala Thr Leu Ala Phe
                455                 460                 465 ttc gcg gtc tcc caa ttg ccc gac gag cag ttc ctg agt tgg ggc tgg    1968
Phe Ala Val Ser Gln Leu Pro Asp Glu Gln Phe Leu Ser Trp Gly Trp
                470                 475                 480 cga ctg ccg ttc ctg ttc agc gcg gtg ctg atc gtg atc ggg ctg ttc    2016
Arg Leu Pro Phe Leu Phe Ser Ala Val Leu Ile Val Ile Gly Leu Phe
            485                 490                 495 att cgc ctg tcc ctg gcc gaa agc ccc gac ttc gcc gag gtg aag gca    2064
Ile Arg Leu Ser Leu Ala Glu Ser Pro Asp Phe Ala Glu Val Lys Ala
        500                 505                 510 cag agc gcc gtg gtg cga atg ccg atc gcc gaa gcg ttc cgc aag cac    2112
Gln Ser Ala Val Val Arg Met Pro Ile Ala Glu Ala Phe Arg Lys His
515                 520                 525                 530 tgg aag gaa att ctc ctc atc gcg ggc acc tac ctg tcc caa gga gtg    2160
Trp Lys Glu Ile Leu Leu Ile Ala Gly Thr Tyr Leu Ser Gln Gly Val
                535                 540                 545 ttc gcc tat atc tgc atg gcc tac ctc gtc tcc tac ggc acc acc gtc    2208
Phe Ala Tyr Ile Cys Met Ala Tyr Leu Val Ser Tyr Gly Thr Thr Val
                550                 555                 560 gcg ggg atc agc cgc acc ttc gcc ctg gcc gga gta ttc gtc gcc ggc    2256
Ala Gly Ile Ser Arg Thr Phe Ala Leu Ala Gly Val Phe Val Ala Gly
            565                 570                 575 atc gtc gcc gtc ctc ctc tac ctc gtg ttc ggc gct ctg tcc gac act    2304
Ile Val Ala Val Leu Leu Tyr Leu Val Phe Gly Ala Leu Ser Asp Thr
        580                 585                 590 ttc ggc cgc aag acc atg tac ctg ctc ggc gcc gcc gcg atg ggt gtg    2352
Phe Gly Arg Lys Thr Met Tyr Leu Leu Gly Ala Ala Ala Met Gly Val
595                 600                 605                 610 gtg atc gcc ccc gcc ttc gca ctg atc aac acc ggc aac ccg tgg ctg    2400
Val Ile Ala Pro Ala Phe Ala Leu Ile Asn Thr Gly Asn Pro Trp Leu
                615                 620                 625 ttc atg gcc gcg cag gtg ctg gtc ttc gga att gca atg gcc ccc gcc    2448
Phe Met Ala Ala Gln Val Leu Val Phe Gly Ile Ala Met Ala Pro Ala
                630                 635                 640 gcc ggc gtg aca ggc tcc ctg ttc acg atg gtc ttc gac gcg gac gtg    2496
Ala Gly Val Thr Gly Ser Leu Phe Thr Met Val Phe Asp Ala Asp Val
            645                 650                 655
```

```
cgc tac agc ggt gtc tct atc ggc tac acc atc tcc cag gtc gcc ggc    2544
Arg Tyr Ser Gly Val Ser Ile Gly Tyr Thr Ile Ser Gln Val Ala Gly
    660             665             670 tcc gcg ttc gcc ccg acg atc gcg acc gcc ttg tac gcc tcc acc aac    2592
Ser Ala Phe Ala Pro Thr Ile Ala Thr Ala Leu Tyr Ala Ser Thr Asn
675             680              685             690 acc agc aac tcg atc gtg acc tac ctg ctg atc gtc tcg gcc atc tcg    2640
Thr Ser Asn Ser Ile Val Thr Tyr Leu Leu Ile Val Ser Ala Ile Ser
                695             700             705 atc gtc tcg gtg atc ctg ctg ccc ggc ggc tgg ggg cgc aag ggc gct    2688
Ile Val Ser Val Ile Leu Leu Pro Gly Gly Trp Gly Arg Lys Gly Ala
            710             715             720 gcg agc cag ctc act cgc gac cag gcc acc tcc aca ccg aaa atg cct    2736
Ala Ser Gln Leu Thr Arg Asp Gln Ala Thr Ser Thr Pro Lys Met Pro
        725             730             735 gac acc gaa aca ttt tcg act cgg aca gtt ccg gac acc gca gca tcc    2784
Asp Thr Glu Thr Phe Ser Thr Arg Thr Val Pro Asp Thr Ala Ala Ser
    740             745             750 ctg cgc gtc ctc gac aag tga a gtg atg aca gac atg agt gac cac gac    2833
Leu Arg Val Leu Asp Lys       Val Met Thr Asp Met Ser Asp His Asp
755             760                       765 cgc acc tcc tac gac acc gac gtc gtg atc gtc ggc ctc ggc ccc gcc    2881
Arg Thr Ser Tyr Asp Thr Asp Val Val Ile Val Gly Leu Gly Pro Ala
770             775             780             785 ggt ggc aca gcg gcg ctt gcc ctg gcc agc tac ggc atc cgc gtt cac    2929
Gly Gly Thr Ala Ala Leu Ala Leu Ala Ser Tyr Gly Ile Arg Val His
                790             795             800 gcc gtc tcg atg ttc ccc tgg gtg gcg aac tcg ccg cgc gcg cac atc    2977
Ala Val Ser Met Phe Pro Trp Val Ala Asn Ser Pro Arg Ala His Ile
            805             810             815 acc aac cag cgc gcc gtc gaa gtg ctg cgt gac ctg ggc gtc gaa gac    3025
Thr Asn Gln Arg Ala Val Glu Val Leu Arg Asp Leu Gly Val Glu Asp
        820             825             830 gag gcg cgc aac tac gcc acc ccg tgg gac cag atg ggc gac acg ctg    3073
Glu Ala Arg Asn Tyr Ala Thr Pro Trp Asp Gln Met Gly Asp Thr Leu
    835             840             845 ttc acc acg agc ctg gcc ggc gag gag atc gtc cgg atg cag acc tgg    3121
Phe Thr Thr Ser Leu Ala Gly Glu Glu Ile Val Arg Met Gln Thr Trp
850             855             860             865 ggt acg ggc gat atc cgc tac ggg gac tac ctg tcc gga agc ccc tgc    3169
Gly Thr Gly Asp Ile Arg Tyr Gly Asp Tyr Leu Ser Gly Ser Pro Cys
                870             875             880
```

```
acg atg ctc gac att ccg cag ccc ctg atg gag ccg gtc ctg atc aag     3217
Thr Met Leu Asp Ile Pro Gln Pro Leu Met Glu Pro Val Leu Ile Lys
        885             890             895 aac gcc gcc gaa cgt ggt gcg gtc atc agc ttc aac acc gaa tac ctc     3265
Asn Ala Ala Glu Arg Gly Ala Val Ile Ser Phe Asn Thr Glu Tyr Leu
        900             905             910 gac cac gcc cag gac gag gac ggg gtg acc gtc cgg ttc cgc gac gtc     3313
Asp His Ala Gln Asp Glu Asp Gly Val Thr Val Arg Phe Arg Asp Val
        915             920             925 cgc tcg ggc acc gtg ttc acc cag cga gcc cgc ttc ctc ctc ggt ttc     3361
Arg Ser Gly Thr Val Phe Thr Gln Arg Ala Arg Phe Leu Leu Gly Phe
930             935             940             945 gac ggc gca cga tcg aag atc gcc gaa cag atc ggg ctt ccg ttc gaa     3409
Asp Gly Ala Arg Ser Lys Ile Ala Glu Gln Ile Gly Leu Pro Phe Glu
            950             955             960 ggt gaa ctc gcc cgc gcc ggt acc gcg tac atc ctg ttc aac gcg gac     3457
Gly Glu Leu Ala Arg Ala Gly Thr Ala Tyr Ile Leu Phe Asn Ala Asp
            965             970             975 ctg agc aaa tat gtc gct cat cgg ccg agc atc ttg cac tgg atc gtc     3505
Leu Ser Lys Tyr Val Ala His Arg Pro Ser Ile Leu His Trp Ile Val
        980             985             990 aac tcg aag gcc ggt ttc ggt  gag atc ggc atg ggt  ctg ctg cgc gcg  3553
Asn Ser Lys Ala Gly Phe Gly  Glu Ile Gly Met Gly  Leu Leu Arg Ala
        995             1000            1005 atc  cga ccg tgg gac cag  tgg atc gcc ggc tgg  ggc ttc gac atg      3598
Ile  Arg Pro Trp Asp Gln  Trp Ile Ala Gly Trp  Gly Phe Asp Met
1010            1015            1020 gcg  aac ggc gag ccg gat  gtc tcc gac gac gtt  gtc ctc gaa cag      3643
Ala  Asn Gly Glu Pro Asp  Val Ser Asp Asp Val  Val Leu Glu Gln
1025            1030            1035 atc  cgg acc ctc gtc ggc  gac ccg cac ctg gac  gtc gag atc gtg      3688
Ile  Arg Thr Leu Val Gly  Asp Pro His Leu Asp  Val Glu Ile Val
1040            1045            1050 tcg  agg tcc ttc tgg tac  gtc aac cgg cag tgg  gct gag cac tac      3733
Ser  Arg Ser Phe Trp Tyr  Val Asn Arg Gln Trp  Ala Glu His Tyr
1055            1060            1065 cag  tcc ggt cga gtg ttc  tgc ggc ggc gac gcg  gtg cac cgg cat      3778
Gln  Ser Gly Arg Val Phe  Cys Gly Gly Asp Ala  Val His Arg His
1070            1075            1080 ccg  ccg agc agc ggg ctg  ggc tcg aac acg tcc  atg cag gac gcg      3823
Pro  Pro Ser Ser Gly Leu  Gly Ser Asn Thr Ser  Met Gln Asp Ala
1085            1090            1095
```

```
ttc aac ctg gca tgg aag atc gcg ttc gtc gtg aag ggg tat gca      3868
Phe Asn Leu Ala Trp Lys Ile Ala Phe Val Val Lys Gly Tyr Ala
1100                1105                1110 gga ccg ggt ctg ctc gag tcc tac tct cct gag cgt gtt ccg gtc      3913
Gly Pro Gly Leu Leu Glu Ser Tyr Ser Pro Glu Arg Val Pro Val
1115                1120                1125 ggc aaa cag atc gtc gct cgc gcc aac cag tcc cgc aag gac tac      3958
Gly Lys Gln Ile Val Ala Arg Ala Asn Gln Ser Arg Lys Asp Tyr
1130                1135                1140 gcc ggg ctg cgc gaa tgg ttc gat cac gag agc gac gac ccg gtc      4003
Ala Gly Leu Arg Glu Trp Phe Asp His Glu Ser Asp Asp Pro Val
1145                1150                1155 gcc gcc ggc ctg gca aag ttg aag gaa ccc tcg tcc gaa ggt gtt      4048
Ala Ala Gly Leu Ala Lys Leu Lys Glu Pro Ser Ser Glu Gly Val
1160                1165                1170 gct ctg cgt gag cgg ctg tac gag gcg ctg gag gtg aag aac gcc      4093
Ala Leu Arg Glu Arg Leu Tyr Glu Ala Leu Glu Val Lys Asn Ala
1175                1180                1185 gaa ttc aac gcc cag ggc gtc gaa ctc aac cag cgc tac acc tcg      4138
Glu Phe Asn Ala Gln Gly Val Glu Leu Asn Gln Arg Tyr Thr Ser
1190                1195                1200 tcc gcg gtc gtt ccc gac ccc gag gcg ggc gag gaa gtg tgg gtg      4183
Ser Ala Val Val Pro Asp Pro Glu Ala Gly Glu Glu Val Trp Val
1205                1210                1215 cgc gat cgt gag ctg tac ctg cag gcc acc acc cgg ccg ggc gcg      4228
Arg Asp Arg Glu Leu Tyr Leu Gln Ala Thr Thr Arg Pro Gly Ala
1220                1225                1230 aag ctg ccg cat gcg tgg ctg gtc ggc gcc gac gga acc cgc atc      4273
Lys Leu Pro His Ala Trp Leu Val Gly Ala Asp Gly Thr Arg Ile
1235                1240                1245 tcc acc ctc gac gtc acc ggc aag gga atg atg acc ctg ctg acc      4318
Ser Thr Leu Asp Val Thr Gly Lys Gly Met Met Thr Leu Leu Thr
1250                1255                1260 gga ctc ggc ggc cag gca tgg aag cgt gcc gcc gcc aaa ctc gac      4363
Gly Leu Gly Gly Gln Ala Trp Lys Arg Ala Ala Ala Lys Leu Asp
1265                1270                1275 ctg ccg ttc ctg cgg acc gtc gtt gtc ggc gaa ccc ggc acc atc      4408
Leu Pro Phe Leu Arg Thr Val Val Val Gly Glu Pro Gly Thr Ile
1280                1285                1290 gac cct tac gga tac tgg cgg cgg gtc cgc gac atc gac gag gcc      4453
Asp Pro Tyr Gly Tyr Trp Arg Arg Val Arg Asp Ile Asp Glu Ala
1295                1300                1305
```

```
ggc gcc ctg ctc gtg cgg  ccc gac ggc tac gtc  gcg tgg cga cac         4498
Gly Ala Leu Leu Val Arg  Pro Asp Gly Tyr Val  Ala Trp Arg His
1310                1315                 1320 agt gct ccg gtc tgg gac  gac acc gaa gcg ctc  acc agc ctc gag         4543
Ser Ala Pro Val Trp Asp  Asp Thr Glu Ala Leu  Thr Ser Leu Glu
1325                1330                 1335 aac gct ctc acc gcg gtc  ctc gac cac tcg gcc  agc gac aac ggg         4588
Asn Ala Leu Thr Ala Val  Leu Asp His Ser Ala  Ser Asp Asn Gly
1340                1345                 1350 aac ccg agc ggc aca aac  gag ccg cag tac agc  acc cgg gcc gtg         4633
Asn Pro Ser Gly Thr Asn  Glu Pro Gln Tyr Ser  Thr Arg Ala Val
1355                1360                 1365 ccg atc gtc gtt ccg cac  gtt acc gcc gag gat  gca gca cca gct         4678
Pro Ile Val Val Pro His  Val Thr Ala Glu Asp  Ala Ala Pro Ala
1370                1375                 1380 tcc gcc acc cgc acc acc  aca gtc gag gga gag  aac cga tga             4720
Ser Ala Thr Arg Thr Thr  Thr Val Glu Gly Glu  Asn Arg
1385                1390                 1395 cccgtcctta caccagcgtc tgggacgacc tgaaccaggt cgagttcagc caggggattca    4780
tccaggccgg ccctaccgg accgatacc tgcacgccgg cgactcgtcc aagcccacgc       4840
tgatcctgct gcacggcatc accggccacg ccgaggcgta cgtgcgcaat ctgcgctcgc     4900
attccgagca cttcaacgtc tgggcaatcg acttcatcgg ccacggctat tcgaccaagc     4960
ccgaccaccc gctcgagatc aagcactaca tcgaccacgt gctgcagttg ctggacgcca    5020
tcggcgtcga gaaggcctcg ttttccgggg agtctctcgg cggttgggtc accgcccagt    5080
tcgcgcacga ccatcccgag aaggtcgacc ggatcgtgct caacaccatg ggcggcacca    5140
tggccaaccc tcaggtgatg gaacgtctct atacctgtc gatggaagcg gcgaaggacc     5200
cgagctggga acgcgtcaaa gcacgcctcg aatggctcat ggccgacccg accatggtca    5260
ccgacgacct gatccgcacc cgccaggcca tcttccagca gccggattgg ctcaaggcct    5320
gcgagatgaa catggcactg caggacctcg aaacccgcaa gcggaacatg atcaccgacg    5380
ccactctcaa cggcatcacg gtgcccgcga tggtgctgtg gaccaccaag gaccctccg     5440
gtccggtcga cgaagccaag cgcatcgcct cccacatccc gggcgccaag ctggccatca    5500
tggagaactg tggccactgg ccccagtacg aggaccccga gaccttcaac aagctgcatc    5560
tggacttcct cctcggtcgc agctgacaca gaccccggcc ggtgccgcca accctgcaa    5620
cccgggcggc accggccgga tctcacttac ccgacctatt gcgctctcgt ccggaccccc    5680
```

```
ggagagaaag cgccgaagca gcagcaagga gaccgccgcg atg cct gta  gcg ctg      5735
                                            Met Pro Val  Ala Leu
                                                    1400 tgc gcg atg tcg cac tcc ccc ctg atg gga cgc aac gac ccc gaa           5780
Cys Ala Met Ser His Ser Pro Leu Met Gly Arg Asn Asp Pro Glu
        1405                1410                1415 cag gaa gtc atc gac gcc gtc gac gcc gca ttc gac cac gcg cgc           5825
Gln Glu Val Ile Asp Ala Val Asp Ala Ala Phe Asp His Ala Arg
        1420                1425                1430 cgg ttc gtc gcc gac ttc gcc ccc gat ctc atc gtc atc ttc gcc           5870
Arg Phe Val Ala Asp Phe Ala Pro Asp Leu Ile Val Ile Phe Ala
        1435                1440                1445 ccc gac cac tac aac ggc gtc ttc tac gac ctg ctg ccg ccg ttc           5915
Pro Asp His Tyr Asn Gly Val Phe Tyr Asp Leu Leu Pro Pro Phe
        1450                1455                1460 tgt atc ggt gcc gcc gcg cag tcc gtc ggc gac tac ggc acc gaa           5960
Cys Ile Gly Ala Ala Ala Gln Ser Val Gly Asp Tyr Gly Thr Glu
        1465                1470                1475 gcc ggc cct ctc gac gtc gac cgt gac gcc gcc tac gca gtc gcc           6005
Ala Gly Pro Leu Asp Val Asp Arg Asp Ala Ala Tyr Ala Val Ala
        1480                1485                1490 cgc gac gtc ctc gac agc ggc atc gac gtc gca ttc tcc gaa cgc           6050
Arg Asp Val Leu Asp Ser Gly Ile Asp Val Ala Phe Ser Glu Arg
        1495                1500                1505 atg cac gtc gac cac gga ttc gcc caa gca ctc caa ttg ctg gtc           6095
Met His Val Asp His Gly Phe Ala Gln Ala Leu Gln Leu Leu Val
        1510                1515                1520 gga tcg atc acc gcc gtg ccg acc gtg ccg atc ttc atc aat tcg           6140
Gly Ser Ile Thr Ala Val Pro Thr Val Pro Ile Phe Ile Asn Ser
        1525                1530                1535 gtc gcc gaa ccg ctc ggc ccg gtc agc cgg gta cgg ctg ctc ggc           6185
Val Ala Glu Pro Leu Gly Pro Val Ser Arg Val Arg Leu Leu Gly
        1540                1545                1550 gag gcg gtc ggg cgg gcc gct gcc aag ctg gac aag cgt gtg ctg           6230
Glu Ala Val Gly Arg Ala Ala Ala Lys Leu Asp Lys Arg Val Leu
        1555                1560                1565 ttc gtc gga tcc ggc ggc ctg tcc cac gac ccg ccg gtc ccg cag           6275
Phe Val Gly Ser Gly Gly Leu Ser His Asp Pro Pro Val Pro Gln
        1570                1575                1580 ttc gcc acc gcg cca gag gaa gtg cgc gag cgg ttg atc gac ggc           6320
Phe Ala Thr Ala Pro Glu Glu Val Arg Glu Arg Leu Ile Asp Gly
        1585                1590                1595
```

```
cgc aat ccc agt gcc gcc gaa cgt gat gcc cgc gaa cag cgc gtc      6365
Arg Asn Pro Ser Ala Ala Glu Arg Asp Ala Arg Glu Gln Arg Val
        1600            1605                1610 atc acc gcc ggg cgg gac ttc gcc gcc ggc acc gcc gcc atc cag      6410
Ile Thr Ala Gly Arg Asp Phe Ala Ala Gly Thr Ala Ala Ile Gln
        1615            1620                1625 cca ctg aac ccc gaa tgg gac cgg cac ctg ctc gac gtc ctc gcc      6455
Pro Leu Asn Pro Glu Trp Asp Arg His Leu Leu Asp Val Leu Ala
        1630            1635                1640 tcc ggc gac ctc gag cag atc gac gcg tgg acc aac gac tgg ttc      6500
Ser Gly Asp Leu Glu Gln Ile Asp Ala Trp Thr Asn Asp Trp Phe
        1645            1650                1655 gtc gaa cag gcc gga cac tcc tcc cac gaa gtg cgc acc tgg atc      6545
Val Glu Gln Ala Gly His Ser Ser His Glu Val Arg Thr Trp Ile
        1660            1665                1670 gcc gcg tac gcg gca atg agc gcc gcc ggg aag tac cgc gtc acc      6590
Ala Ala Tyr Ala Ala Met Ser Ala Ala Gly Lys Tyr Arg Val Thr
        1675            1680                1685 tcg acc ttc tac cgc gaa atc cac gag tgg ata gca gga ttc ggg      6635
Ser Thr Phe Tyr Arg Glu Ile His Glu Trp Ile Ala Gly Phe Gly
        1690            1695                1700 att act acc gcc gtc gcc gtc gac gaa tag accccgccgc tcccgcccg     6685
Ile Thr Thr Ala Val Ala Val Asp Glu
        1705            1710 cagtcccaac gaagggtggc cccggatgac ctccgtccgc cgtgctcgc cgtcggtgaa   6745
cgcgggctgg tcggtgggca ggaagacctc atcgccgaca tcgccctcga cctcgcagct   6805
cgtcagtagg aatgcgcacg ggccgacgag tgcgctggt caccggggcc agccgcggca    6865
tcggggcggc catcgcagat gcggtggccg cctccggtgc cgccgtaatc gtccactacg   6925
gatccgatcg gacggccgcc gctgcggtgt cgacggcatc acggctgccg ggggcctcgc   6985
ggctgcggtc caggccgacc tgtcccgacc cgaggggcct gaagagctga tgcgggagtt   7045
cgactccgcg ctcgacggtc tcgggctcga ccgagggctc gacatcctcg tcaacaacgc   7105
cggaatcagt cggcgcggag cgctcgagcg cgtcactgtc gaggatttcg accgtctggt   7165
cgcactcaac cagcgcgccc cgttcttcgt gactcggcat gccctgcccc ggatgcacga   7225
cggcggtcgc atcgtcaaca tttcctccgg atccgcccgc tacgccagac ccgacgtcat   7285
cagctacgcc atgaccaagg gggcgatcga ggtgctcacc cgcgccctcg ccgtagacgt   7345
cggcgaacga ggcatcaccg ccaacgccgt ggcgccggcc gcgctcgata ccgacatgaa   7405
cgcgcactgg cttcgcggtg acgaccatgc ccgcaccacc gccgcgtcca ccactgcact   7465
```

```
gcgaaaactc gccaccgcgg aggacatcgc cgcgatcgtg gccttcctcg tcagcgccgc    7525
cgccggtgcg atcaccgggc aggtcatcga cgccaccaac ggcaaccggc tctaaccaga    7585
acttacccgg tccc                                                      7599
```

<210> 2
<211> 246
<212> PRT
<213> Rhodococcus sp.

<400> 2

```
Met Thr Thr Thr Asp Thr Gly Pro Lys Pro Gly Ser Glu Ala Ala Ala
1               5                   10                  15

Leu Leu Ala Asn Val Arg Thr Ser Gly Ala Arg Leu Ser Ser Ala Leu
            20                  25                  30

Tyr Asp Ile Leu Lys Asn Arg Leu Glu Gly Arg Tyr Ala Ala Gly
        35                  40                  45

Glu Lys Ile Val Val Glu Ser Ile Arg Gln Glu Phe Gly Val Ser Lys
    50                  55                  60

Gln Pro Val Met Asp Ala Leu Arg Arg Leu Ser Ser Asp Lys Leu Val
65                  70                  75                  80

His Ile Val Pro Gln Val Gly Cys Glu Val Val Ser Tyr Ala Pro Arg
                85                  90                  95

Glu Val Glu Asp Phe Tyr Thr Leu Phe Gly Gly Phe Glu Gly Thr Ile
            100                 105                 110

Ala Ala Val Ala Ala Ser Arg Arg Thr Glu Ala Gln Leu Leu Glu Leu
        115                 120                 125

Asp Leu Ile Ser Ala Arg Val Asp Ala Leu Ile Thr Ser His Asp Pro
    130                 135                 140

Val Val Arg Ala Arg Gly Tyr Arg Val His Asn Arg Glu Phe His Ala
145                 150                 155                 160

Ala Ile His Ala Met Ala His Ser Arg Ile Met Glu Glu Thr Ser Gln
                165                 170                 175

Arg Met Trp Asp Leu Ser Asp Phe Leu Ile Asn Thr Thr Gly Ile Thr
            180                 185                 190

Asn Pro Leu Ser Ser Ala Leu Pro Asp Arg Gln His Asp His His Glu
        195                 200                 205

Ile Thr Glu Ala Ile Arg Asn Arg Asp Ala Ala Ala Arg Glu Ala
    210                 215                 220

Met Glu Arg His Ile Val Gly Thr Ile Ala Val Ile Arg Asp Glu Ser
225                 230                 235                 240
```

Asn Ala Gln Leu Pro Ser
                245

<210> 3
<211> 514
<212> PRT
<213> Rhodococcus sp.

<400> 3
Val Leu Pro Leu Glu Asp Ser Pro Glu Asn Pro Ser Arg Thr Ser Pro
1               5                   10                  15

Glu Glu Arg Ser Gly His Asp Asp Arg Phe Ala Arg Ile Val Leu Arg
            20                  25                  30

Gly Thr Ser Pro Leu Pro Pro Thr Asp Arg Gly Ser Pro Thr Val Ser
        35                  40                  45

Thr Thr Pro Thr Ser Pro Thr Lys Thr Ser Pro Leu Arg Val Ala Met
    50                  55                  60

Ala Ser Phe Ile Gly Thr Thr Val Glu Tyr Tyr Asp Phe Phe Ile Tyr
65                  70                  75                  80

Gly Thr Ala Ala Ala Leu Val Phe Pro Glu Leu Phe Phe Pro Asp Val
                85                  90                  95

Ser Ser Ala Ile Gly Ile Leu Leu Ser Phe Ala Thr Phe Ser Val Gly
                100                 105                 110

Phe Leu Ala Arg Pro Leu Gly Gly Ile Val Phe Gly His Phe Gly Asp
            115                 120                 125

Arg Val Gly Arg Lys Gln Met Leu Val Ile Ser Leu Val Gly Met Gly
        130                 135                 140

Ser Ala Thr Val Leu Met Gly Leu Leu Pro Gly Tyr Ala Gln Ile Gly
145                 150                 155                 160

Ile Ala Ala Pro Ile Leu Leu Thr Leu Leu Arg Leu Val Gln Gly Phe
                165                 170                 175

Ala Val Gly Gly Glu Trp Gly Gly Ala Thr Leu Met Ala Val Glu His
            180                 185                 190

Ala Pro Thr Ala Lys Lys Gly Phe Phe Gly Ser Phe Ser Gln Met Gly
        195                 200                 205

Ala Pro Ala Gly Thr Ser Val Ala Thr Leu Ala Phe Phe Ala Val Ser
    210                 215                 220

Gln Leu Pro Asp Glu Gln Phe Leu Ser Trp Gly Trp Arg Leu Pro Phe
225                 230                 235                 240

Leu Phe Ser Ala Val Leu Ile Val Ile Gly Leu Phe Ile Arg Leu Ser
                245                 250                 255

```
Leu Ala Glu Ser Pro Asp Phe Ala Glu Val Lys Ala Gln Ser Ala Val
            260                 265                 270

Val Arg Met Pro Ile Ala Glu Ala Phe Arg Lys His Trp Lys Glu Ile
            275                 280                 285

Leu Leu Ile Ala Gly Thr Tyr Leu Ser Gln Gly Val Phe Ala Tyr Ile
            290                 295                 300

Cys Met Ala Tyr Leu Val Ser Tyr Gly Thr Thr Val Ala Gly Ile Ser
305                 310                 315                 320

Arg Thr Phe Ala Leu Ala Gly Val Phe Ala Gly Ile Val Ala Val
                325                 330                 335

Leu Leu Tyr Leu Val Phe Gly Ala Leu Ser Asp Thr Phe Gly Arg Lys
            340                 345                 350

Thr Met Tyr Leu Leu Gly Ala Ala Met Gly Val Val Ile Ala Pro
            355                 360                 365

Ala Phe Ala Leu Ile Asn Thr Gly Asn Pro Trp Leu Phe Met Ala Ala
            370                 375                 380

Gln Val Leu Val Phe Gly Ile Ala Met Ala Pro Ala Ala Gly Val Thr
385                 390                 395                 400

Gly Ser Leu Phe Thr Met Val Phe Asp Ala Asp Val Arg Tyr Ser Gly
                405                 410                 415

Val Ser Ile Gly Tyr Thr Ile Ser Gln Val Ala Gly Ser Ala Phe Ala
            420                 425                 430

Pro Thr Ile Ala Thr Ala Leu Tyr Ala Ser Thr Asn Thr Ser Asn Ser
            435                 440                 445

Ile Val Thr Tyr Leu Leu Ile Val Ser Ala Ile Ser Ile Val Ser Val
            450                 455                 460

Ile Leu Leu Pro Gly Gly Trp Gly Arg Lys Gly Ala Ala Ser Gln Leu
465                 470                 475                 480

Thr Arg Asp Gln Ala Thr Ser Thr Pro Lys Met Pro Asp Thr Glu Thr
            485                 490                 495

Phe Ser Thr Arg Thr Val Pro Asp Thr Ala Ala Ser Leu Arg Val Leu
            500                 505                 510

Asp Lys

<210> 4
<211> 637
<212> PRT
<213> Rhodococcus sp.
```

<400> 4

| | | | | | | | | | | | | | | |
|---|---|---|---|---|---|---|---|---|---|---|---|---|---|---|
|Val|Met|Thr|Asp|Met|Ser|Asp|His|Asp|Arg|Thr|Ser|Tyr|Asp|Thr|Asp|
|1| | | |5| | | |10| | | | |15| | |

Val Val Ile Val Gly Leu Gly Pro Ala Gly Thr Ala Ala Leu Ala
            20                 25                 30

Leu Ala Ser Tyr Gly Ile Arg Val His Ala Val Ser Met Phe Pro Trp
        35                 40                 45

Val Ala Asn Ser Pro Arg Ala His Ile Thr Asn Gln Arg Ala Val Glu
    50                 55                 60

Val Leu Arg Asp Leu Gly Val Glu Asp Glu Ala Arg Asn Tyr Ala Thr
65               70                 75               80

Pro Trp Asp Gln Met Gly Asp Thr Leu Phe Thr Thr Ser Leu Ala Gly
            85                 90               95

Glu Glu Ile Val Arg Met Gln Thr Trp Gly Thr Gly Asp Ile Arg Tyr
           100               105            110

Gly Asp Tyr Leu Ser Gly Ser Pro Cys Thr Met Leu Asp Ile Pro Gln
        115               120              125

Pro Leu Met Glu Pro Val Leu Ile Lys Asn Ala Ala Glu Arg Gly Ala
    130               135              140

Val Ile Ser Phe Asn Thr Glu Tyr Leu Asp His Ala Gln Asp Glu Asp
145              150               155            160

Gly Val Thr Val Arg Phe Arg Asp Val Arg Ser Gly Thr Val Phe Thr
           165               170            175

Gln Arg Ala Arg Phe Leu Leu Gly Phe Asp Gly Ala Arg Ser Lys Ile
        180               185             190

Ala Glu Gln Ile Gly Leu Pro Phe Glu Gly Glu Leu Ala Arg Ala Gly
    195               200              205

Thr Ala Tyr Ile Leu Phe Asn Ala Asp Leu Ser Lys Tyr Val Ala His
    210               215            220

Arg Pro Ser Ile Leu His Trp Ile Val Asn Ser Lys Ala Gly Phe Gly
225               230              235            240

Glu Ile Gly Met Gly Leu Leu Arg Ala Ile Arg Pro Trp Asp Gln Trp
           245              250             255

Ile Ala Gly Trp Gly Phe Asp Met Ala Asn Gly Glu Pro Asp Val Ser
        260             265            270

Asp Asp Val Val Leu Glu Gln Ile Arg Thr Leu Val Gly Asp Pro His
    275               280             285

Leu Asp Val Glu Ile Val Ser Arg Ser Phe Trp Tyr Val Asn Arg Gln
290              295             300

15

Trp Ala Glu His Tyr Gln Ser Gly Arg Val Phe Cys Gly Gly Asp Ala
305                 310                 315                 320

Val His Arg His Pro Pro Ser Ser Gly Leu Gly Ser Asn Thr Ser Met
            325                 330                 335

Gln Asp Ala Phe Asn Leu Ala Trp Lys Ile Ala Phe Val Val Lys Gly
            340                 345                 350

Tyr Ala Gly Pro Gly Leu Leu Glu Ser Tyr Ser Pro Glu Arg Val Pro
        355                 360                 365

Val Gly Lys Gln Ile Val Ala Arg Ala Asn Gln Ser Arg Lys Asp Tyr
    370                 375                 380

Ala Gly Leu Arg Glu Trp Phe Asp His Glu Ser Asp Pro Val Ala
385                 390                 395                 400

Ala Gly Leu Ala Lys Leu Lys Glu Pro Ser Ser Glu Gly Val Ala Leu
                405                 410                 415

Arg Glu Arg Leu Tyr Glu Ala Leu Glu Val Lys Asn Ala Glu Phe Asn
            420                 425                 430

Ala Gln Gly Val Glu Leu Asn Gln Arg Tyr Thr Ser Ser Ala Val Val
        435                 440                 445

Pro Asp Pro Glu Ala Gly Glu Val Trp Val Arg Asp Arg Glu Leu
    450                 455                 460

Tyr Leu Gln Ala Thr Thr Arg Pro Gly Ala Lys Leu Pro His Ala Trp
465                 470                 475                 480

Leu Val Gly Ala Asp Gly Thr Arg Ile Ser Thr Leu Asp Val Thr Gly
                485                 490                 495

Lys Gly Met Met Thr Leu Leu Thr Gly Leu Gly Gly Gln Ala Trp Lys
            500                 505                 510

Arg Ala Ala Ala Lys Leu Asp Leu Pro Phe Leu Arg Thr Val Val Val
        515                 520                 525

Gly Glu Pro Gly Thr Ile Asp Pro Tyr Gly Tyr Trp Arg Arg Val Arg
    530                 535                 540

Asp Ile Asp Glu Ala Gly Ala Leu Leu Val Arg Pro Asp Gly Tyr Val
545                 550                 555                 560

Ala Trp Arg His Ser Ala Pro Val Trp Asp Asp Thr Glu Ala Leu Thr
                565                 570                 575

Ser Leu Glu Asn Ala Leu Thr Ala Val Leu Asp His Ser Ala Ser Asp
            580                 585                 590

Asn Gly Asn Pro Ser Gly Thr Asn Glu Pro Gln Tyr Ser Thr Arg Ala
        595                 600                 605

```
Val Pro Ile Val Val Pro His Val Thr Ala Glu Asp Ala Ala Pro Ala
    610             615                 620
Ser Ala Thr Arg Thr Thr Thr Val Glu Gly Glu Asn Arg
625             630                 635
```

<210> 5
<211> 314
<212> PRT
<213> Rhodococcus sp.

<400> 5

```
Met Pro Val Ala Leu Cys Ala Met Ser His Ser Pro Leu Met Gly Arg
1               5                   10                  15
Asn Asp Pro Glu Gln Glu Val Ile Asp Ala Val Asp Ala Ala Phe Asp
                20                  25                  30
His Ala Arg Arg Phe Val Ala Asp Phe Ala Pro Asp Leu Ile Val Ile
            35                  40                  45
Phe Ala Pro Asp His Tyr Asn Gly Val Phe Tyr Asp Leu Leu Pro Pro
        50                  55                  60
Phe Cys Ile Gly Ala Ala Ala Gln Ser Val Gly Asp Tyr Gly Thr Glu
65                  70                  75                  80
Ala Gly Pro Leu Asp Val Asp Arg Asp Ala Ala Tyr Ala Val Ala Arg
                85                  90                  95
Asp Val Leu Asp Ser Gly Ile Asp Val Ala Phe Ser Glu Arg Met His
                100                 105                 110
Val Asp His Gly Phe Ala Gln Ala Leu Gln Leu Leu Val Gly Ser Ile
            115                 120                 125
Thr Ala Val Pro Thr Val Pro Ile Phe Ile Asn Ser Val Ala Glu Pro
130                 135                 140
Leu Gly Pro Val Ser Arg Val Arg Leu Leu Gly Glu Ala Val Gly Arg
145                 150                 155                 160
Ala Ala Ala Lys Leu Asp Lys Arg Val Leu Phe Val Gly Ser Gly Gly
                165                 170                 175
Leu Ser His Asp Pro Pro Val Pro Gln Phe Ala Thr Ala Pro Glu Glu
            180                 185                 190
Val Arg Glu Arg Leu Ile Asp Gly Arg Asn Pro Ser Ala Ala Glu Arg
        195                 200                 205
Asp Ala Arg Glu Gln Arg Val Ile Thr Ala Gly Arg Asp Phe Ala Ala
    210                 215                 220
Gly Thr Ala Ala Ile Gln Pro Leu Asn Pro Glu Trp Asp Arg His Leu
225                 230                 235                 240
```

```
Leu Asp Val Leu Ala Ser Gly Asp Leu Glu Gln Ile Asp Ala Trp Thr
            245                 250                 255

Asn Asp Trp Phe Val Glu Gln Ala Gly His Ser Ser His Glu Val Arg
            260                 265                 270

Thr Trp Ile Ala Ala Tyr Ala Ala Met Ser Ala Ala Gly Lys Tyr Arg
            275                 280                 285

Val Thr Ser Thr Phe Tyr Arg Glu Ile His Glu Trp Ile Ala Gly Phe
            290                 295                 300

Gly Ile Thr Thr Ala Val Ala Val Asp Glu
305                 310
```

<210> 6
<211> 870
<212> DNA
<213> Rhodococcus sp.

<220>
<221> CDS
<222> (1)..(867)

```
<400> 6
atg acc cgt cct tac acc agc gtc tgg gac gac ctg aac cag gtc gag     48
Met Thr Arg Pro Tyr Thr Ser Val Trp Asp Asp Leu Asn Gln Val Glu
  1               5                  10                  15 ttc agc cag gga ttc atc cag gcc ggc ccc tac cgg acc cga tac ctg     96
Phe Ser Gln Gly Phe Ile Gln Ala Gly Pro Tyr Arg Thr Arg Tyr Leu
                 20                  25                  30 cac gcc ggc gat tcg tcc aag ccc acg ctg atc ctg ctg cac ggc atc    144
His Ala Gly Asp Ser Ser Lys Pro Thr Leu Ile Leu Leu His Gly Ile
             35                  40                  45 acc ggc cac gcc gag gcg tac gtg cgc aat ctg cgc tcg cat tcc gag    192
Thr Gly His Ala Glu Ala Tyr Val Arg Asn Leu Arg Ser His Ser Glu
 50                  55                  60 cac ttc aac gtc tgg gca atc gac ttc atc ggc cac ggc tat tcg acc    240
His Phe Asn Val Trp Ala Ile Asp Phe Ile Gly His Gly Tyr Ser Thr
 65                  70                  75                  80 aag ccc gac cac ccg ctc gag atc aag cac tac atc gac cag gtg ctg    288
Lys Pro Asp His Pro Leu Glu Ile Lys His Tyr Ile Asp Gln Val Leu
                 85                  90                  95 cag ttg ctg gac gcc atc ggc gtc gag aag gcc tcg ttt tcc ggg gag    336
Gln Leu Leu Asp Ala Ile Gly Val Glu Lys Ala Ser Phe Ser Gly Glu
            100                 105                 110
```

```
tct ctc ggc ggt tgg gtc acc gcc cag ttc gcg cac gac cat ccc gag       384
Ser Leu Gly Gly Trp Val Thr Ala Gln Phe Ala His Asp His Pro Glu
        115                 120                 125 aag gtc gac cgg atc gtg ctc aac acc atg ggc ggc acc atg gcc aac       432
Lys Val Asp Arg Ile Val Leu Asn Thr Met Gly Gly Thr Met Ala Asn
130                 135                 140 cct cag gtg atg gaa cgt ctc tat acc ctg tcg atg gaa gcg gcg aag       480
Pro Gln Val Met Glu Arg Leu Tyr Thr Leu Ser Met Glu Ala Ala Lys
145                 150                 155                 160 gac ccg agc tgg gaa cgc gtc aaa gca cgc ctc gaa tgg ctc atg gcc       528
Asp Pro Ser Trp Glu Arg Val Lys Ala Arg Leu Glu Trp Leu Met Ala
                165                 170                 175 gac ccg acc atg gtc acc gac gac ctg atc cgc acc cgc cag gcc atc       576
Asp Pro Thr Met Val Thr Asp Asp Leu Ile Arg Thr Arg Gln Ala Ile
                180                 185                 190 ttc cag cag ccg gat tgg ctc aag gcc tgc gag atg aac atg gca ctg       624
Phe Gln Gln Pro Asp Trp Leu Lys Ala Cys Glu Met Asn Met Ala Leu
        195                 200                 205 cag gac ctc gaa acc cgc aag cgg aac atg atc acc gac gcc act ctc       672
Gln Asp Leu Glu Thr Arg Lys Arg Asn Met Ile Thr Asp Ala Thr Leu
210                 215                 220 aac ggc atc acg gtg ccc gcg atg gtg ctg tgg acc acc aag gac ccc       720
Asn Gly Ile Thr Val Pro Ala Met Val Leu Trp Thr Thr Lys Asp Pro
225                 230                 235                 240 tcc ggt ccg gtc gac gaa gcc aag cgc atc gcc tcc cac atc ccg ggc       768
Ser Gly Pro Val Asp Glu Ala Lys Arg Ile Ala Ser His Ile Pro Gly
                245                 250                 255 gcc aag ctg gcc atc atg gag aac tgt ggc cac tgg ccc cag tac gag       816
Ala Lys Leu Ala Ile Met Glu Asn Cys Gly His Trp Pro Gln Tyr Glu
                260                 265                 270 gac ccc gag acc ttc aac aag ctg cat ctg gac ttc ctc ctc ggt cgc       864
Asp Pro Glu Thr Phe Asn Lys Leu His Leu Asp Phe Leu Leu Gly Arg
        275                 280                 285 agc tga                                                                870
Ser

<210> 7
<211> 289
<212> PRT
<213> Rhodococcus sp.

<400> 7
Met Thr Arg Pro Tyr Thr Ser Val Trp Asp Asp Leu Asn Gln Val Glu
  1               5                  10                  15
```

19

Phe Ser Gln Gly Phe Ile Gln Ala Gly Pro Tyr Arg Thr Arg Tyr Leu
        20                      25                      30

His Ala Gly Asp Ser Ser Lys Pro Thr Leu Ile Leu Leu His Gly Ile
        35                      40                      45

Thr Gly His Ala Glu Ala Tyr Val Arg Asn Leu Arg Ser His Ser Glu
        50                      55                      60

His Phe Asn Val Trp Ala Ile Asp Phe Ile Gly His Gly Tyr Ser Thr
65                      70                      75                      80

Lys Pro Asp His Pro Leu Glu Ile Lys His Tyr Ile Asp Gln Val Leu
                85                      90                      95

Gln Leu Leu Asp Ala Ile Gly Val Glu Lys Ala Ser Phe Ser Gly Glu
            100                     105                     110

Ser Leu Gly Gly Trp Val Thr Ala Gln Phe Ala His Asp His Pro Glu
        115                     120                     125

Lys Val Asp Arg Ile Val Leu Asn Thr Met Gly Gly Thr Met Ala Asn
130                     135                     140

Pro Gln Val Met Glu Arg Leu Tyr Thr Leu Ser Met Glu Ala Ala Lys
145                     150                     155                     160

Asp Pro Ser Trp Glu Arg Val Lys Ala Arg Leu Glu Trp Leu Met Ala
            165                     170                     175

Asp Pro Thr Met Val Thr Asp Asp Leu Ile Arg Thr Arg Gln Ala Ile
            180                     185                     190

Phe Gln Gln Pro Asp Trp Leu Lys Ala Cys Glu Met Asn Met Ala Leu
        195                     200                     205

Gln Asp Leu Glu Thr Arg Lys Arg Asn Met Ile Thr Asp Ala Thr Leu
        210                     215                     220

Asn Gly Ile Thr Val Pro Ala Met Val Leu Trp Thr Thr Lys Asp Pro
225                     230                     235                     240

Ser Gly Pro Val Asp Glu Ala Lys Arg Ile Ala Ser His Ile Pro Gly
            245                     250                     255

Ala Lys Leu Ala Ile Met Glu Asn Cys Gly His Trp Pro Gln Tyr Glu
            260                     265                     270

Asp Pro Glu Thr Phe Asn Lys Leu His Leu Asp Phe Leu Leu Gly Arg
        275                     280                     285

Ser

<210> 8
<211> 27
<212> DNA
<213> Artificial Sequence

<220>
<223> Description of Artificial Sequence: Synthetic olig OHPR3

<400> 8
atcgaattcg gatccatgac caccacc                                27

<210> 9
<211> 44
<212> DNA
<213> Artificial Sequence

<220>
<223> Description of Artificial Sequence: Synthetic olig OHPR4

<400> 9
atcgcggccg ctctagacta actgcagggc gccaagctcg gcag             44

<210> 10
<211> 24
<212> DNA
<213> Artificial Sequence

<220>
<223> Description of Artificial Sequence: Synthetic olig C11

<400> 10
atcgaattcg gatccacgag agag                                   24

<210> 11
<211> 29
<212> DNA
<213> Artificial Sequence

<220>
<223> Description of Artificial Sequence: Synthetic olig C12

<400> 11
atccggccgc gctctagagt acgcaagct                              29

<210> 12
<211> 20
<212> DNA
<213> Artificial Sequence

<220>
<223> Description of Artificial Sequence: Synthetic olig op1

21

<400> 12
atcctcgaga ccccgatacc                                                    20

<210> 13
<211> 17
<212> DNA
<213> Artificial Sequence

<220>
<223> Description of Artificial Sequence: Synthetic olig op2

<400> 13
atcgtcgacc gctaccc                                                       17

<210> 14
<211> 50
<212> DNA
<213> Artificial Sequence

<220>
<223> Description of Artificial Sequence: Synthetic olig CaMVop2

<400> 14
tccactgacg taagggatga cgcacaatcc cactatcctt cgcaagaccc                    50

<210> 15
<211> 50
<212> DNA
<213> Artificial Sequence

<220>
<223> Description of Artificial Sequence: Synthetic olig CaMVop3

<400> 15
atgctagacg tctagttcag acgctactta tatagaggaa gggtcttgcg                    50

<210> 16
<211> 45
<212> DNA
<213> Artificial Sequence

<220>
<223> Description of Artificial Sequence: Synthetic olig CaMVop4

<400> 16
cgtctagcat tctagttgag gaagttcatt tcatttggag aggac                         45

<210> 17
<211> 23
<212> DNA
<213> Artificial Sequence

<220>
<223> Description of Artificial Sequence: Synthetic olig CaMVopF1

<400> 17
atcgatatct ccactgacgt aag                                                    23

<210> 18
<211> 24
<212> DNA
<213> Artificial Sequence

<220>
<223> Description of Artificial Sequence: Synthetic olig CaMVopR1

<400> 18
gatggatccg tcctctccaa atga                                                   24

<210> 19
<211> 470
<212> DNA
<213> Artificial Sequence

<220>
<223> Description of Artificial Sequence: Synthetic Promoter

<400> 19
catgcctgca ggtcaacatg gtggagcacg acactctcgt ctactccaag aatatcaaag      60
atacagtctc agaagaccag agggctattg acttttca acaaagggta atatcgggaa       120
acctcctcgg attccattgc ccagctatct gtcacttcat cgaaaggaca gtagaaaagg     180
aagatggctt ctacaaatgc catcattgcg ataaaggaaa ggctatcgtt caagaatgcc     240
tctaccgaca gtggtcccaa agatgtaccc ccacccacga ggaacatcgt ggaaaaagaa     300
gacgttccaa ccacgtcttc aaagcaagtg gattgatgtg atatctccac tgacgtaagg     360
gatgacgcac aatcccacta tccttcgcaa gacccttcct ctatataagt agcgtctgaa     420
ctagacgtct agcattctag ttgaggaagt tcatttcatt tggagaggac                470